(12) United States Patent
Pensaert et al.

(10) Patent No.: US 7,851,607 B2
(45) Date of Patent: *Dec. 14, 2010

(54) NUCLEIC ACID ENCODING POLYPEPTIDE INVOLVED IN CELLULAR ENTRANCE OF THE PRRS VIRUS

(75) Inventors: Maurice Pensaert, Berlare (BE); Hans Nauwynck, Zomergem (BE); Nathalie Vanderheijden, Merelbeke (BE)

(73) Assignee: Universiteit Gent, Gent (BE)

( * ) Notice: Subject to any disclaimer, the term of this patent is extended or adjusted under 35 U.S.C. 154(b) by 496 days.

This patent is subject to a terminal disclaimer.

(21) Appl. No.: 11/781,558

(22) Filed: Jul. 23, 2007

(65) Prior Publication Data

US 2008/0057537 A1 Mar. 6, 2008

Related U.S. Application Data

(63) Continuation of application No. 10/485,045, filed as application No. PCT/EP02/08047 on Jul. 18, 2002, now Pat. No. 7,563,881.

(30) Foreign Application Priority Data

Jul. 24, 2001 (EP) .................................. 01202824
Oct. 31, 2001 (EP) .................................. 01204220

(51) Int. Cl.
C07H 21/04 (2006.01)
C12N 15/12 (2006.01)
C12N 15/85 (2006.01)
C12N 7/00 (2006.01)
C12N 7/02 (2006.01)
C12N 5/16 (2006.01)
C12P 21/02 (2006.01)

(52) U.S. Cl. ................ 536/23.5; 435/320.1; 435/235.1; 435/325; 435/70.1; 435/455

(58) Field of Classification Search ....................... None
See application file for complete search history.

(56) References Cited

U.S. PATENT DOCUMENTS

2004/0248124 A1 12/2004 Pensaert et al.
2009/0104147 A1 4/2009 Delputte et al.

FOREIGN PATENT DOCUMENTS

WO WO03010200 * 2/2003

OTHER PUBLICATIONS

Vanderheijden, N. et al., "Involvement of Sialoadhesin in Entry of Porcine Reproductive and Respiratory Syndrome Virus into Porcine Alveolar Macrophages," J. Virology, vol. 77, No. 15, p. 8207-8215 (2003).
Nauwynck, H. et al., "PRRSV-macrophage interaction and putative receptors," Veterinary Research, vol. 31, No. 1, p. 22 (Jan. 2000).

Therrien, D. et al., "Preliminary characterization of protein binding factor for porcine reproductive and respiratory syndrome virus on the surface of permissive and non-permissive cells," Archives of Virology, vol. 145, p. 1099-1116 (2000).
Nauwynck, H. et al., "Entry of porcine reproductive and respiratory syndrome virus into porcine alveolar macrophages via receptor-mediated endocytosis," Journal of General Virology, vol. 80, p. 297-305 (1999).
Duan, X. et al., "Identification of a Putative Receptor for Porcine Reproductive and Respiratory Syndrome Virus on Porcine Alveolar Macrophages," Journal of Virology, vol. 72, No. 5, p. 4520-4523 (May 1998).
Duan, X., et al., "Porcine reproductive and respiratory syndrome virus Infection of alveolar macrophages can be blocked by monoclonal antibodies against cell surface antigens," Advances in Experimental Medicine and Biology, vol. 440, p. 81-88 (1998).
Duan, X., et al., "Effects of origin and state of differentiation and activation of monocytes/macrophages on their susceptibility to porcine reproductive and respiratory syndrome virus (PRRSV)," Archives of Virology, vol. 142, p. 2483-2497 (1997).
Crocker, P., et al., "Sialoadhesin, a macrophage sialic acid binding receptor for haemopoietic cells with 17 immunoglobulin-like domains," The EMBO Journal, vol. 13, No. 19, p. 4490-4503 (1994).
Ngo, J. et al., "Computational Complexity, Protein Structure Prediction, and the Levinthal Paradox," from "The Protein Folding Problem and Tertiary Structure Prediction," Birkhauser Boston, p. 491-495 (1994).
Rudinger, J., "Characteristics of the amino acids as components of a peptide sequence," in "Peptide Hormones," University Park Press, p. 1-7 (1976).
Frishman et al., Seventy-Five Percent Accuracy in Protein Secondary Structure Prediction, Proteins: Structure, Function and Genetics, 1997, pp. 329-335, vol. 27.

* cited by examiner

*Primary Examiner*—Michael Burkhart
(74) *Attorney, Agent, or Firm*—TraskBritt

(57) ABSTRACT

The present invention relates to a new polynucleotide that encodes a polypeptide involved in cellular entrance of PRRSV, to a recombinant vector comprising said polynucleotide, to a cell capable of expressing said polypeptide, a method of producing said polypeptide as well as to cell culture and to a novel method of producing the PRRSV virus. The present invention further relates to a method of identifying compounds that affect the PRRSV receptor function of the polypeptide as well as to the use of the polypeptide or identified compounds in the manufacture of medicaments. The present inventors have succeeded in isolating a protein from PAM membranes that seems to play a crucial role in virus entry into the cell. The elucidated nucleotide sequence encoding the protein, as well as the amino acid sequence of the protein, were compared with sequences stored in sequence databases. Surprisingly the putative PRRSV receptor provided by the present invention showed a great deal of homology to certain proteins belonging to the Siglec family.

12 Claims, 28 Drawing Sheets

Figure 1:
Figure 1:
Figure 1:
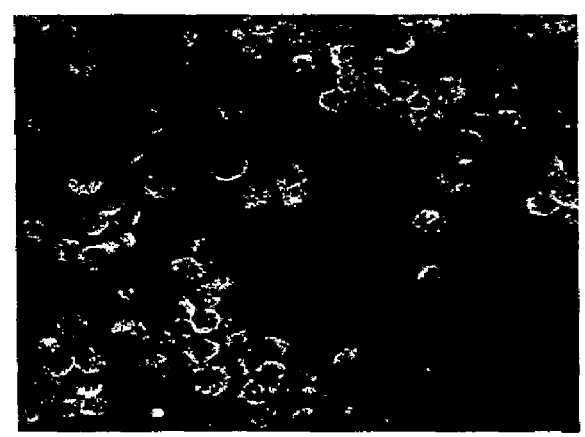

A.

B.

C.

FIGURE 3A

```
                10                  30                  50
                 .                   .                   .
      atggacttcctgctcctgctcctcctcctggcttcatctgctctagcaggcctggcctcg
  1   ---------+---------+---------+---------+---------+---------+   60
      tacctgaaggacgaggacgaggaggaggaccgaagtagacgagatcgtccggaccggagc
      M  D  F  L  L  L  L  L  L  A  S  S  A  L  A  G  L  A  S 70                  90                 110
                 .                   .                   .
      tggacggtttccagccccgagaccgtgcagggcatcaagggctcctgcctcatcatcccc
 61   ---------+---------+---------+---------+---------+---------+  120
      acctgccaaaggtcggggctctggcacgtcccgtagttcccgaggacggagtagtagggg
      W  T  V  S  P  E  T  V  Q  G  I  K  G  S  C  L  I  I  P 130                 150                 170
                 .                   .                   .
      tgcaccttcggcttcccggccaacgtggaggtgccccatggcatcacagccatctggtac
121   ---------+---------+---------+---------+---------+---------+  180
      acgtggaagccgaagggccggttgcacctccacggggtaccgtagtgtcggtagaccatg
      C  T  F  G  F  P  A  N  V  E  V  P  H  G  I  T  A  I  W  Y 190                 210                 230
                 .                   .                   .
      tatgactactcaggcaagcgcctggtagtgagccactccaggaacccaaaggtggtggag
181   ---------+---------+---------+---------+---------+---------+  240
      atactgatgagtccgttcgcggaccatcactcggtgaggtccttgggtttccaccacctc
      Y  D  Y  S  G  K  R  L  V  V  S  H  S  R  N  P  K  V  V  E 250                 270                 290
                 .                   .                   .
      aaccacttccaaggccgggccctgctgttgGGGCAGGTTGAACAGAGGACGTGCAGCCTG
241   ---------+---------+---------+---------+---------+---------+  300
      ttggtgaaggttccggcccgggacgacaacCCCGTCCAACTTGTCTCCTGCACGTCGGAC
      N  H  F  Q  G  R  A  L  L  L  G  Q  V  E  Q  R  T  C  S  L 310                 330                 350
                 .                   .                   .
      CTGCTGAAGGACCTGCAGCCCCAGGACTCGGGCTCCTATAACTTCCGCTTTGAGATCAGC
301   ---------+---------+---------+---------+---------+---------+  360
      GACGACTTCCTGGACGTCGGGGTCCTGAGCCCGAGGATATTGAAGGCGAAACTCTAGTCG
      L  L  K  D  L  Q  P  Q  D  S  G  S  Y  N  F  R  F  E  I  S 370                 390                 410
                 .                   .                   .
      GAGGGCAACCGCTGGTCAGATGTCAAAGGCACAGTTGTCACCGTGACAGAGGTGCCCAGC
361   ---------+---------+---------+---------+---------+---------+  420
      CTCCCGTTGGCGACCAGTCTACAGTTTCCGTGTCAACAGTGGCACTGTCTCCACGGGTCG
      E  G  N  R  W  S  D  V  K  G  T  V  V  T  V  T  E  V  P  S
```

FIGURE 3B

```
                 430                 450                  470
       GTGCCCACCATTGCCTTGCCAGCCAAGCTGCATGAGGGCATGGAGGTGGACTTCAACTGC
421    ---------+---------+---------+---------+---------+---------+    480
       CACGGGTGGTAACGGAACGGTCGGTTCGACGTACTCCCGTACCTCCACCTGAAGTTGACG
        V  P  T  I  A  L  P  A  K  L  H  E  G  M  E  V  D  F  N  C 490                 510                  530
       TCCACTCCCTATGTGTGCCCGACGGAGCCGGTCAACCTACAGTGGCAAGGCCAGGATCCC
481    ---------+---------+---------+---------+---------+---------+    540
       AGGTGAGGGATACACACGGGCTGCCTCGGCCAGTTGGATGTCACCGTTCCGGTCCTAGGG
        S  T  P  Y  V  C  P  T  E  P  V  N  L  Q  W  Q  G  Q  D  P 550                 570                  590
       ACCCGCTCCGTCACCTCCCACCTCCAGAAGCTTGAGCCCTCGGGCACCAGCCACATGGAG
541    ---------+---------+---------+---------+---------+---------+    600
       TGGGCGAGGCAGTGGAGGGTGGAGGTCTTCGAACTCGGGAGCCCGTGGTCGGTGTACCTC
        T  R  S  V  T  S  H  L  Q  K  L  E  P  S  G  T  S  H  M  E 610                 630                  650
       ACCCTGCACATGGCCCTGTCCTGGCAGGACCATGGCCGGATCCTGAGCTGCCAGGTCTCA
601    ---------+---------+---------+---------+---------+---------+    660
       TGGGACGTGTACCGGGACAGGACCGTCCTGGTACCGGCCTAGGACTCGACGGTCCAGAGT
        T  L  H  M  A  L  S  W  Q  D  H  G  R  I  L  S  C  Q  V  S 670                 690                  710
       GCAGCCGAACGCAGGATGCAGAAGGAGATTCACCTCCAAGTGCAGTATGCCCCCAAGGGT
661    ---------+---------+---------+---------+---------+---------+    720
       CGTCGGCTTGCGTCCTACGTCTTCCTCTAAGTGGAGGTTCACGTCATACGGGGGTTCCCA
        A  A  E  R  R  M  Q  K  E  I  H  L  Q  V  Q  Y  A  P  K  G 730                 750                  770
       GTGGAGATCCTTTTCAGCCACTCCGGACGGAACGTCCTTCCAGGTGATCTGGTCACCCTC
721    ---------+---------+---------+---------+---------+---------+    780
       CACCTCTAGGAAAAGTCGGTGAGGCCTGCCTTGCAGGAAGGTCCACTAGACCAGTGGGAG
        V  E  I  L  F  S  H  S  G  R  N  V  L  P  G  D  L  V  T  L 790                 810                  830
       AGCTGCCAGGTGAATAGCAGCAACCCTCAGGTCAGTTCCGTGCAGTGGGTCAAGGATGGG
781    ---------+---------+---------+---------+---------+---------+    840
       TCGACGGTCCACTTATCGTCGTTGGGAGTCCAGTCAAGGCACGTCACCCAGTTCCTACCC
        S  C  Q  V  N  S  S  N  P  Q  V  S  S  V  Q  W  V  K  D  G
```

FIGURE 3C

```
              850                    870                    890
              .                      .                      .
     ACGAAGCTCAAAGACCAGAAACGTGTACTGCAGTTGCGCCGGGCAGCCTGGGCTGATGCT
841  ---------+---------+---------+---------+---------+---------+  900
     TGCTTCGAGTTTCTGGTCTTTGCACATGACGTCAACGCGGCCCGTCGGACCCGACTACGA
      T  K  L  K  D  Q  K  R  V  L  Q  L  R  R  A  A  W  A  D  A 910                    930                    950
              .                      .                      .
     GGCGTCTACACCTGCCAAGCCGGGAATGCCGTGGGCTCTTCAGTCTCACCCCCGGTCAGC
901  ---------+---------+---------+---------+---------+---------+  960
     CCGCAGATGTGGACGGTTCGGCCCTTACGGCACCCGAGAAGTCAGAGTGGGGGCCAGTCG
      G  V  Y  T  C  Q  A  G  N  A  V  G  S  S  V  S  P  P  V  S 970                    990                   1010
              .                      .                      .
     CTCCACGTCTTCATGGCTGAGGTCCAGGTAAGCCCTGTGGGCTCCATCCTGGAGAACCAG
961  ---------+---------+---------+---------+---------+---------+  1020
     GAGGTGCAGAAGTACCGACTCCAGGTCCATTCGGGACACCCGAGGTAGGACCTCTTGGTC
      L  H  V  F  M  A  E  V  Q  V  S  P  V  G  S  I  L  E  N  Q 1030                   1050                   1070
              .                      .                      .
     ACGGTGACGCTGGCCTGCAATACACCTAAGGAAGCGCCCAGCGAGCTGCGCTACAGCTGG
1021 ---------+---------+---------+---------+---------+---------+  1080
     TGCCACTGCGACCGGACGTTATGTGGATTCCTTCGCGGGTCGCTCGACGCGATGTCGACC
      T  V  T  L  A  C  N  T  P  K  E  A  P  S  E  L  R  Y  S  W 1090                   1110                   1130
              .                      .                      .
     TACAAGAACCACGCCCTGCTGGAGGGCTCTCACAGCCGCACCCTCCGGCTGCACTCAGTT
1081 ---------+---------+---------+---------+---------+---------+  1140
     ATGTTCTTGGTGCGGGACGACCTCCCGAGAGTGTCGGCGTGGGAGGCCGACGTGAGTCAA
      Y  K  N  H  A  L  L  E  G  S  H  S  R  T  L  R  L  H  S  V 1150                   1170                   1190
              .                      .                      .
     ACCAGGGCGGATTCGGGCTTCTACTTCTGCGAGGTGCAGAACGCCCGGGGCAGAGAGCGC
1141 ---------+---------+---------+---------+---------+---------+  1200
     TGGTCCCGCCTAAGCCCGAAGATGAAGACGCTCCACGTCTTGCGGGCCCCGTCTCTCGCG
      T  R  A  D  S  G  F  Y  F  C  E  V  Q  N  A  R  G  R  E  R 1210                   1230                   1250
              .                      .                      .
     TCTCCCCCTGTCAGCGTGGTGGTCAGCCACCCACCCCTCACCCCGGACCTAACTGCCTTC
1201 ---------+---------+---------+---------+---------+---------+  1260
     AGAGGGGGACAGTCGCACCACCAGTCGGTGGGTGGGGAGTGGGGCCTGGATTGACGGAAG
      S  P  P  V  S  V  V  V  S  H  P  P  L  T  P  D  L  T  A  F
```

FIGURE 3D

```
          1270                1290                1310
           .                   .                   .
       CTGGAGACACAGGCGGGGCTGGTGGGCATCCTCCAATGCTCTGTGGTCAGCGAGCCCCCA
1261   ---------+---------+---------+---------+---------+---------+  1320
       GACCTCTGTGTCCGCCCCGACCACCCGTAGGAGGTTACGAGACACCAGTCGCTCGGGGGT
        L  E  T  Q  A  G  L  V  G  I  L  Q  C  S  V  V  S  E  P  P 1330                1350                1370
           .                   .                   .
       GCTACTCTGGTGTTGTCACACGGGGGCCTCATCTTGGCCTCTACCTCCGGGGAGGGTGAC
1321   ---------+---------+---------+---------+---------+---------+  1380
       CGATGAGACCACAACAGTGTGCCCCCGGAGTAGAACCGGAGATGGAGGCCCCTCCCACTG
        A  T  L  V  L  S  H  G  G  L  I  L  A  S  T  S  G  E  G  D 1390                1410                1430
           .                   .                   .
       CACAGCCCACGCTTCAGTGTCGCCTCTGCCCCCAACTCCCTGCGCCTGGAGATTCAAGAC
1381   ---------+---------+---------+---------+---------+---------+  1440
       GTGTCGGGTGCGAAGTCACAGCGGAGACGGGGGTTGAGGGACGCGGACCTCTAAGTTCTG
        H  S  P  R  F  S  V  A  S  A  P  N  S  L  R  L  E  I  Q  D 1450                1470                1490
           .                   .                   .
       CTGGGGCCAACAGACAGTGGGGAATACATGTGCTCAGCCAGCAGTTCTCTTGGGAATGCG
1441   ---------+---------+---------+---------+---------+---------+  1500
       GACCCCGGTTGTCTGTCACCCCTTATGTACACGAGTCGGTCGTCAAGAGAACCCTTACGC
        L  G  P  T  D  S  G  E  Y  M  C  S  A  S  S  S  L  G  N  A 1510                1530                1550
           .                   .                   .
       TCCTCCACCCTGGACTTCCATGCCAATGCAGCCCGCCTCCTCATCAGCCCAGCAGCAGAG
1501   ---------+---------+---------+---------+---------+---------+  1560
       AGGAGGTGGGACCTGAAGGTACGGTTACGTCGGGCGGAGGAGTAGTCGGGTCGTCGTCTC
        S  S  T  L  D  F  H  A  N  A  A  R  L  L  I  S  P  A  A  E 1570                1590                1610
           .                   .                   .
       GTGGTGGAAGGGCAGGCGGTGACACTGAGCTGCAGGAGCAGCCTGAGCCTGATGCCTGAC
1561   ---------+---------+---------+---------+---------+---------+  1620
       CACCACCTTCCCGTCCGCCACTGTGACTCGACGTCCTCGTCGGACTCGGACTACGGACTG
        V  V  E  G  Q  A  V  T  L  S  C  R  S  S  L  S  L  M  P  D 1630                1650                1670
           .                   .                   .
       ACCCGTTTTTCCTGGTACCTGAACGGGGCCCTGATTCTCGAGGGGCCCAGCAGCAGCCTC
1621   ---------+---------+---------+---------+---------+---------+  1680
       TGGGCAAAAAGGACCATGGACTTGCCCCGGGACTAAGAGCTCCCCGGGTCGTCGTCGGAG
        T  R  F  S  W  Y  L  N  G  A  L  I  L  E  G  P  S  S  S  L
```

FIGURE 3E

```
              1690                1710                1730
              .                   .                   .         .
      CTGCTCCCAGCAGCCTCCAGCACAGATGCCGGCTCATACCACTGCCGGGCCCAGAACAGC
1681  ---------+---------+---------+---------+---------+---------+  1740
      GACGAGGGTCGTCGGAGGTCGTGTCTACGGCCGAGTATGGTGACGGCCCGGGTCTTGTCG
       L  L  P  A  A  S  S  T  D  A  G  S  Y  H  C  R  A  Q  N  S 1750                1770                1790
              .                   .                   .         .
      CACAGCACCAGCGGGCCCTCCTCACCTGCTGTTCTCACCGTGCTCTACGCCCCACGCCAG
1741  ---------+---------+---------+---------+---------+---------+  1800
      GTGTCGTGGTCGCCCGGGAGGAGTGGACGACAAGAGTGGCACGAGATGCGGGGTGCGGTC
       H  S  T  S  G  P  S  S  P  A  V  L  T  V  L  Y  A  P  R  Q 1810                1830                1850
              .                   .                   .         .
      CCCGTGTTCACTGCCCAGCTGGACCCTGATACTGCAGGAGCTGGGGCCGGACGCCAAGGC
1801  ---------+---------+---------+---------+---------+---------+  1860
      GGGCACAAGTGACGGGTCGACCTGGGACTATGACGTCCTCGACCCCGGCCTGCGGTTCCG
       P  V  F  T  A  Q  L  D  P  D  T  A  G  A  G  R  Q  G 1870                1890                1910
              .                   .                   .         .
      CTCCTCTTGTGCCGTGTGGACAGCGACCCCCAGCCCAGCTGCAGCTGCTCCACAGGGGC
1861  ---------+---------+---------+---------+---------+---------+  1920
      GAGGAGAACACGGCACACCTGTCGCTGGGGGGTCGGGTCGACGTCGACGAGGTGTCCCCG
       L  L  L  C  R  V  D  S  D  P  P  A  Q  L  Q  L  L  H  R  G 1930                1950                1970
              .                   .                   .         .
      CGTGTTGTGGCCTCTTCTCTGTCATGGGGGGGCGGCTGCTGCACCTGCGGAGGCTGTTTC
1921  ---------+---------+---------+---------+---------+---------+  1980
      GCACAACACCGGAGAAGAGACAGTACCCCCCGCCGACGACGTGGACGCCTCCGACAAAG
       R  V  V  A  S  S  L  S  W  G  G  G  C  T  C  G  G  C  F 1990                2010                2030
              .                   .                   .         .
      CACCGCATGAAGGTCACCAAAGCACCCAACCTACTGCGTGTAGAGATCCGAGACCCGGTG
1981  ---------+---------+---------+---------+---------+---------+  2040
      GTGGCGTACTTCCAGTGGTTTCGTGGGTTGGATGACGCACATCTCTAGGCTCTGGGCCAC
       H  R  M  K  V  T  K  A  P  N  L  L  R  V  E  I  R  D  P  V 2050                2070                2090
              .                   .                   .         .
      CTGGAGGATGAGGGTGTGTACCTGTGCGAGGCCAGCAGCGCCCTGGGCAACGCCTCCGCC
2041  ---------+---------+---------+---------+---------+---------+  2100
      GACCTCCTACTCCCACACATGGACACGCTCCGGTCGTCGCGGGACCCGTTGCGGAGGCGG
       L  E  D  E  G  V  Y  L  C  E  A  S  S  A  L  G  N  A  S  A
```

FIGURE 3F

```
              2110                2130                 2150
       TCTGCAACCTTGGATGCCCAGGCCACTGTCCTGGTCATCACACCGTCACACACGCTGCAG
2101   ---------+---------+---------+---------+---------+---------+   2160
       AGACGTTGGAACCTACGGGTCCGGTGACAGGACCAGTAGTGTGGCAGTGTGTGCGACGTC
        S  A  T  L  D  A  Q  A  T  V  L  V  I  T  P  S  H  T  L  Q 2170                2190                 2210
       GAAGGCATTGAAGCCAACCTGACTTGCAACGTGAGCCGTGAAGCCAGCGGCCCTGCCAAC
2161   ---------+---------+---------+---------+---------+---------+   2220
       CTTCCGTAACTTCGGTTGGACTGAACGTTGCACTCGGCACTTCGGTCGCCGGGACGGTTG
        E  G  I  E  A  N  L  T  C  N  V  S  R  E  A  S  G  P  A  N 2230                2250                 2270
       TTCTCCTGGTTCCGAGATGGGGCGCTATGGGCCCAGGGCCCTCTGGACACCGTGACGCTG
21     ---------+---------+---------+---------+---------+---------+   2280
       AAGAGGACCAAGGCTCTACCCCGCGATACCCGGGTCCCGGGAGACCTGTGGCACTGCGAC
        F  S  W  F  R  D  G  A  L  W  A  Q  G  P  L  D  T  V  T  L 2290                2310                 2330
       CTACCTGTGGCCAGAACTGATGCTGCCCTCTATGCTTGCCGCATCGTCACCGAGGCTGGT
2281   ---------+---------+---------+---------+---------+---------+   2340
       GATGGACACCGGTCTTGACTACGACGGGAGATACGAACGGCGTAGCAGTGGCTCCGACCA
        L  P  V  A  R  T  D  A  A  L  Y  A  C  R  I  V  T  E  A  G 2350                2370                 2390
       GCTGGCCTCTCCACCCCTGTGGCCCTGAATGTGCTCTATCCCCCCGATCCTCCAAAGTTG
2341   ---------+---------+---------+---------+---------+---------+   2400
       CGACCGGAGAGGTGGGGACACCGGGACTTACACGAGATAGGGGGGCTAGGAGGTTTCAAC
        A  G  L  S  T  P  V  A  L  N  V  L  Y  P  P  D  P  P  K  L 2410                2430                 2450
       TCAGCCCTCCTGGACGTGGACCAGGGCCACACGGCTGTGTTCGTCTGTACTGTGGACAGT
2401   ---------+---------+---------+---------+---------+---------+   2460
       AGTCGGGAGGACCTGCACCTGGTCCCGGTGTGCCGACACAAGCAGACATGACACCTGTCA
        S  A  L  L  D  V  D  Q  G  H  T  A  V  F  V  C  T  V  D  S 2470                2490                 2510
       CGCCCTCTTGCCCAGTTGGCCCTGTTCCGTGGGGAACACCTCCTGGCCGCCAGCTCGGCA
2461   ---------+---------+---------+---------+---------+---------+   2520
       GCGGGAGAACGGGTCAACCGGGACAAGGCACCCCTTGTGGAGGACCGGCGGTCGAGCCGT
        R  P  L  A  Q  L  A  L  F  R  G  E  H  L  L  A  A  S  S  A
```

FIGURE 3G

```
              2530              2550              2570
     CTCCGGCTCCCCCCTCGTGGCCGCCTCCAGGCCAAAGCCTCGGCCAACTCCTTGCAGCTA
2521 ---------+---------+---------+---------+---------+---------+ 2580
     GAGGCCGAGGGGGGAGCACCGGCGGAGGTCCGGTTTCGGAGCCGGTTGAGGAACGTCGAT
     L  R  L  P  P  R  G  R  L  Q  A  K  A  S  A  N  S  L  Q  L 2590              2610              2630
     GAGGTCCGAGACTTGAGCCTTGGGGACTCTGGCAGCTACCACTGTGAGGCCACCAACATC
2581 ---------+---------+---------+---------+---------+---------+ 2640
     CTCCAGGCTCTGAACTCGGAACCCCTGAGACCGTCGATGGTGACACTCCGGTGGTTGTAG
     E  V  R  D  L  S  L  G  D  S  G  S  Y  H  C  E  A  T  N  I 2650              2670              2690
     CTTGGATCAGCCAACACTTCTCTTACCTTCCAGGTCCGAGGAGCCTGGGTCCGGGTGTCA
2641 ---------+---------+---------+---------+---------+---------+ 2700
     GAACCTAGTCGGTTGTGAAGAGAATGGAAGGTCCAGGCTCCTCGGACCCAGGCCCACAGT
     L  G  S  A  N  T  S  L  T  F  Q  V  R  G  A  W  V  R  V  S 2710              2730              2750
     CCGTCGCCTGAGCTCCAGGAGGGCCAGGCTGTGGTCCTGAGCTGCCAGGTACCCATAGGG
2701 ---------+---------+---------+---------+---------+---------+ 2760
     GGCAGCGGACTCGAGGTCCTCCCGGTCCGACACCAGGACTCGACGGTCCATGGGTATCCC
     P  S  P  E  L  Q  E  G  Q  A  V  V  L  S  C  Q  V  P  I  G 2770              2790              2810
     GTCCTGGAGGGGACCTCATATCGTTGGTATCGGGATGGCCAGCCCCTCCAGGAGTCCACT
2761 ---------+---------+---------+---------+---------+---------+ 2820
     CAGGACCTCCCCTGGAGTATAGCAACCATAGCCCTACCGGTCGGGGAGGTCCTCAGGTGA
     V  L  E  G  T  S  Y  R  W  Y  R  D  G  Q  P  L  Q  E  S  T 2830              2850              2870
     TCGGCCACGCTCCGTTTTGCAGCCATAACTCTGAGCCAGGCTGGAGCCTACCATTGCCAA
2821 ---------+---------+---------+---------+---------+---------+ 2880
     AGCCGGTGCGAGGCAAAACGTCGGTATTGAGACTCGGTCCGACCTCGGATGGTAACGGTT
     S  A  T  L  R  F  A  A  I  T  L  S  Q  A  G  A  Y  H  C  Q 2890              2910              2930
     GCCCAAGCTCCAGGCTCAGCCACCACGGACCTGGCTGCCCCTGTCAGCCTCCACGTGACC
2881 ---------+---------+---------+---------+---------+---------+ 2940
     CGGGTTCGAGGTCCGAGTCGGTGGTGCCTGGACCGACGGGGACAGTCGGAGGTGCACTGG
     A  Q  A  P  G  S  A  T  T  D  L  A  A  P  V  S  L  H  V  T
```

FIGURE 3H

```
              2950                2970                2990
                 .                   .                   .
        TACGCACCTCGCCAGGCCACACTCACCACCCTGATGGACTCAGGCCTCGGGCGACTGGGC
2941    ---------+---------+---------+---------+---------+---------+    3000
        ATGCGTGGAGCGGTCCGGTGTGAGTGGTGGGACTACCTGAGTCCGGAGCCCGCTGACCCG
         Y  A  P  R  Q  A  T  L  T  T  L  M  D  S  G  L  G  R  L  G 3010                3030                3050
                 .                   .                   .
        CTCCTTCTGTGCCGTGTGAACAGTGACCCTCCTGCCCAGCTCCGACTGCTCCATGGGAGC
3001    ---------+---------+---------+---------+---------+---------+    3060
        GAGGAAGACACGGCACACTTGTCACTGGGAGGACGGGTCGAGGCTGACGAGGTACCCTCG
         L  L  L  C  R  V  N  S  D  P  P  A  Q  L  R  L  L  H  G  S 3070                3090                3110
                 .                   .                   .
        CGCCTCGTGGCCTCTACTCTACAAGGTGTGGAGGAGCTTGCAGGCAGCTCTCCCCGCCTA
3061    ---------+---------+---------+---------+---------+---------+    3120
        GCGGAGCACCGGAGATGAGATGTTCCACACCTCCTCGAACGTCCGTCGAGAGGGGCGGAT
         R  L  V  A  S  T  L  Q  G  V  E  E  L  A  G  S  S  P  R  L 3130                3150                3170
                 .                   .                   .
        CAGGTGGCCACAGCCCCCAACACGCTGCGCCTGGAGATCCACAACGCAGTGCTGGAGGAT
3121    ---------+---------+---------+---------+---------+---------+    3180
        GTCCACCGGTGTCGGGGGTTGTGCGACGCGGACCTCTAGGTGTTGCGTCACGACCTCCTA
         Q  V  A  T  A  P  N  T  L  R  L  E  I  H  N  A  V  L  E  D 3190                3210                3230
                 .                   .                   .
        GAAGGCGTCTACACCTGCGAGGCCACCAACACCCTGGGTCAGACCTTGGCCTCCGCCGCC
3181    ---------+---------+---------+---------+---------+---------+    3240
        CTTCCGCAGATGTGGACGCTCCGGTGGTTGTGGGACCCAGTCTGGAACCGGAGGCGGCGG
         E  G  V  Y  T  C  E  A  T  N  T  L  G  Q  T  L  A  S  A  A 3250                3270                3290
                 .                   .                   .
        TTCGATGCCCAGGCTATGAGAGTGCAGGTGTGGCCCAATGCCACCGTGCAAGAGGGGCAG
3241    ---------+---------+---------+---------+---------+---------+    3300
        AAGCTACGGGTCCGATACTCTCACGTCCACACCGGGTTACGGTGGCACGTTCTCCCCGTC
         F  D  A  Q  A  M  R  V  Q  V  W  P  N  A  T  V  Q  E  G  Q 3310                3330                3350
                 .                   .                   .
        CTGGTGAACCTGACCTGCCTTGTATGGACCACGCACCTGGCCCAGCTCACCTACACGTGG
3301    ---------+---------+---------+---------+---------+---------+    3360
        GACCACTTGGACTGGACGGAACATACCTGGTGCGTGGACCGGGTCGAGTGGATGTGCACC
         L  V  N  L  T  C  L  V  W  T  T  H  L  A  Q  L  T  Y  T  W
```

FIGURE 3I

```
              3370                3390                3410
      TACCGAGACCAGCAGCAGCTCCCAGGTGCTGCCCACTCCATCCTCCTGCCCAATGTCACT
3361  ---------+---------+---------+---------+---------+---------+  3420
      ATGGCTCTGGTCGTCGTCGAGGGTCCACGACGGGTGAGGTAGGAGGACGGGTTACAGTGA
       Y  R  D  Q  Q  Q  L  P  G  A  A  H  S  I  L  L  P  N  V  T 3430                3450                3470
      GTCACAGATGCCGCCTCCTACCGCTGTGGCATATTGATCCCTGGCCAGGCACTCCGCCTC
3421  ---------+---------+---------+---------+---------+---------+  3480
      CAGTGTCTACGGCGGAGGATGGCGACACCGTATAACTAGGGACCGGTCCGTGAGGCGGAG
       V  T  D  A  A  S  Y  R  C  G  I  L  I  P  G  Q  A  L  R  L 3490                3510                3530
      TCCAGACCTGTCGCCCTGGATGTCCTCTACGCACCCCGCAGACTGCGCCTGACCCATCTC
3481  ---------+---------+---------+---------+---------+---------+  3540
      AGGTCTGGACAGCGGGACCTACAGGAGATGCGTGGGGCGTCTGACGCGGACTGGGTAGAG
       S  R  P  V  A  L  D  V  L  Y  A  P  R  R  L  R  L  T  H  L 3550                3570                3590
      TTGGAGAGCCGTGGTGGGCAGCTGGCCGTGGTGCTGTGCACTGTGGACAGTCGCCCAGCT
3541  ---------+---------+---------+---------+---------+---------+  3600
      AACCTCTCGGCACCACCCGTCGACCGGCACCACGACACGTGACACCTGTCAGCGGGTCGA
       L  E  S  R  G  G  Q  L  A  V  V  L  C  T  V  D  S  R  P  A 3610                3630                3650
      GCCCAGCTGACCCTCAGCCATGCTGGCCGCCTCCTGGCCTCCTCAACCGCAGCCTCTGTC
3601  ---------+---------+---------+---------+---------+---------+  3660
      CGGGTCGACTGGGAGTCGGTACGACCGGCGGAGGACCGGAGGAGTTGGCGTCGGAGACAG
       A  Q  L  T  L  S  H  A  G  R  L  L  A  S  S  T  A  A  S  V 3670                3690                3710
      CCCAACACCCTGCGCCTGGAGCTGTGGGAGCCCCGGCCCAGTGATGAGGGTCTCTACAGC
3661  ---------+---------+---------+---------+---------+---------+  3720
      GGGTTGTGGGACGCGGACCTCGACACCCTCGGGGCCGGGTCACTACTCCCAGAGATGTCG
       P  N  T  L  R  L  E  L  W  E  P  R  P  S  D  E  G  L  Y  S 3730                3750                3770
      TGCTCGGCCCGCAGTCCTCTGGGCCAGGCCAACACATCCCTGGAGCTGCGGCTAGAGGGC
3721  ---------+---------+---------+---------+---------+---------+  3780
      ACGAGCCGGGCGTCAGGAGACCCGGTCCGGTTGTGTAGGGACCTCGACGCCGATCTCCCG
       C  S  A  R  S  P  L  G  Q  A  N  T  S  L  E  L  R  L  E  G
```

FIGURE 3J

```
              3790                3810                3830
                 .                   .                   .
        GTGCAGGTGGCACTGGCTCCATCGGCCACTGTGCCGGAGGGGGCCCCTGTCACAGTGACC
3781    ---------+---------+---------+---------+---------+---------+   3840
        CACGTCCACCGTGACCGAGGTAGCCGGTGACACGGCCTCCCCCGGGGACAGTGTCACTGG
         V  Q  V  A  L  A  P  S  A  T  V  P  E  G  A  P  V  T  V  T 3850                3870                3890
                 .                   .                   .
        TGTGAAGACCCTGCTGCCCGCCCACCCACTCTCTATGTCTGGTACCACAACAGCCGTTGG
3841    ---------+---------+---------+---------+---------+---------+   3900
        ACACTTCTGGGACGACGGGCGGGTGGGTGAGAGATACAGACCATGGTGTTGTCGGCAACC
         C  E  D  P  A  A  R  P  P  T  L  Y  V  W  Y  H  N  S  R  W 3910                3930                3950
                 .                   .                   .
        CTGCAGGAGGGGTCGGCTGCCTCCCTCTCGTTTCCAGCGGCTACACGGGCTCACGCGGGC
3901    ---------+---------+---------+---------+---------+---------+   3960
        GACGTCCTCCCCAGCCGACGGAGGGAGAGCAAAGGTCGCCGATGTGCCCGAGTGCGCCCG
         L  Q  E  G  S  A  A  S  L  S  F  P  A  A  T  R  A  H  A  G 3970                3990                4010
                 .                   .                   .
        GCCTATACCTGCCAGGTCCAGGATGCCCAGGGCACACGCATCTCCCAGCCCGCAGCACTG
3961    ---------+---------+---------+---------+---------+---------+   4020
        CGGATATGGACGGTCCAGGTCCTACGGGTCCCGTGTGCGTAGAGGGTCGGGCGTCGTGAC
         A  Y  T  C  Q  V  Q  D  A  Q  G  T  R  I  S  Q  P  A  A  L 4030                4050                4070
                 .                   .                   .
        CACATCCTCTATGCCCCTCGGGATGCtgtcctttcctccttctgggactcaagggccagc
4021    ---------+---------+---------+---------+---------+---------+   4080
        GTGTAGGAGATACGGGGAGCCCTACgacaggaaaggaggaagaccctgagttcccggtcg
         H  I  L  Y  A  P  R  D  A  V  L  S  S  F  W  D  S  R  A  S 4090                4110                4130
                 .                   .                   .
        cctatggccgtggtacagtgcactgtggacagcgagccacctgccgagatgaccctgtcc
4081    ---------+---------+---------+---------+---------+---------+   4140
        ggataccggcaccatgtcacgtgacacctgtcgctcggtggacggctctactgggacagg
         P  M  A  V  V  Q  C  T  V  D  S  E  P  P  A  E  M  T  L  S 4150                4170                4190
                 .                   .                   .
        catgatggcaaggtgctggccaccagccatggggtccacggcttagcagtggggacaggc
4141    ---------+---------+---------+---------+---------+---------+   4200
        gtactaccgttccacgaccggtggtcggtacccccaggtgccgaatcgtcaccctgtccg
         H  D  G  K  V  L  A  T  S  H  G  V  H  G  L  A  V  G  T  G
```

FIGURE 3K

```
           4210                4230                4250
             .                   .                   .
     catgtccaggtggcccgcaacgccctgcagctgcggctgcagaatgtgccctcacgtgac
4201 ---------+---------+---------+---------+---------+---------+ 4260
     gtacaggtccaccgggcgttgcgggacgtcgacgcccacgtcttacacgggagtgcactg
      H  V  Q  V  A  R  N  A  L  Q  L  R  V  Q  N  V  P  S  R  D 4270                4290                4310
             .                   .                   .
     aaggacacctacgtctgcatggaccgcaactccttgggctcagtcagcaccatggggcag
4261 ---------+---------+---------+---------+---------+---------+ 4320
     ttcctgtggatgcagacgtacctggcgttgaggaacccgagtcagtcgtggtaccccgtc
      K  D  T  Y  V  C  M  D  R  N  S  L  G  S  V  S  T  M  G  Q 4330                4350                4370
             .                   .                   .
     ctgcagccagaaggtgtgcacgtggtagctgagccagggctggatgtgcctgaaggcaca
4321 ---------+---------+---------+---------+---------+---------+ 4380
     gacgtcggtcttccacacgtgcaccatcgactcggtcccgacctacacggacttccgtgt
      L  Q  P  E  G  V  H  V  V  A  E  P  G  L  D  V  P  E  G  T 4390                4410                4430
             .                   .                   .
     gcgctgaacctgagctgtcgcctccctagtggccctgggcacataggcaactccaccttt
4381 ---------+---------+---------+---------+---------+---------+ 4440
     cgcgacttggactcgacagcggagggatcaccgggacccgtgtatccgttgaggtggaaa
      A  L  N  L  S  C  R  L  P  S  G  P  G  H  I  G  N  S  T  F 4450                4470                4490
             .                   .                   .
     gcttggttccggaacggtcggcagctacacacagagtctgtgcccaccccttaccttcacc
4441 ---------+---------+---------+---------+---------+---------+ 4500
     cgaaccaaggccttgccagccgtcgatgtgtgtctcagacacgggtgggaatggaagtgg
      A  W  F  R  N  G  R  Q  L  H  T  E  S  V  P  T  L  T  F  T 4510                4530                4550
             .                   .                   .
     catgtggcccgcgcccaagctggcttgtaccactgccaggctgagctccccgccggggct
4501 ---------+---------+---------+---------+---------+---------+ 4560
     gtacaccgggcgcgggttcgaccgaacatggtgacggtccgactcgaggggcggccccga
      H  V  A  R  A  Q  A  G  L  Y  H  C  Q  A  E  L  P  A  G  A 4570                4590                4610
             .                   .                   .
     gccacctctgctccagtcttgctccgggtgctctaccctcccaagacgcccaccatgact
4561 ---------+---------+---------+---------+---------+---------+ 4620
     cggtggagacgaggtcagaacgaggcccacgagatgggagggttctgcggtggtactga
      A  T  S  A  P  V  L  L  R  V  L  Y  P  P  K  T  P  T  M  T
```

FIGURE 3L

```
                4630                4650                4670
         gttttttgtggagcccgagggtggcatccagggcattctggactgccgagtggacagtgag
4621     ---------+---------+---------+---------+---------+---------+    4680
         caaaaacacctcgggctcccaccgtaggtcccgtaagacctgacggctcacctgtcactc
          V  F  V  E  P  E  G  G  I  Q  G  I  L  D  C  R  V  D  S  E 4690                4710                4730
         cccctagccagcctgaccctccacctgggcagtcggctggtggcctccagccagcctcag
4681     ---------+---------+---------+---------+---------+---------+    4740
         ggggatcggtcggactgggaggtggacccgtcagccgaccaccggaggtcggtcggagtc
          P  L  A  S  L  T  L  H  L  G  S  R  L  V  A  S  S  Q  P  Q 4750                4770                4790
         gctgcccctgccaagccgcacatccgcgtctcagccagtcccaatgcCTTGCGAGTGGAC
4741     ---------+---------+---------+---------+---------+---------+    4800
         cgacggggacggttcggcgtgtaggcgcagagtcggtcagggttacgGAACGCTCACCTG
          A  A  P  A  K  P  H  I  R  V  S  A  S  P  N  A  L  R  V  D 4810                4830                4850
         ATGGAGGAGCTGAAGCCCAGTGACCAGGGGGAGTATGTGTGCTCGGCCTCCAATGCCCTG
4801     ---------+---------+---------+---------+---------+---------+    4860
         TACCTCCTCGACTTCGGGTCACTGGTCCCCCTCATACACACGAGCCGGAGGTTACGGGAC
          M  E  E  L  K  P  S  D  Q  G  E  Y  V  C  S  A  S  N  A  L 4870                4890                4910
         GGCTCTGCCTCTGCTGCCACCTACTTCGGAACCAGAGCCCTGCATCGCCTGCATCTGTTC
4861     ---------+---------+---------+---------+---------+---------+    4920
         CCGAGACGGAGACGACGGTGGATGAAGCCTTGGTCTCGGGACGTAGCGGACGTAGACAAG
          G  S  A  S  A  A  T  Y  F  G  T  R  A  L  H  R  L  H  L  F 4930                4950                4970
         CAGCACCTTCTCTGGTTCCTGGGGCTGCTGGCGAGCCTCCTCTTCCTACTGTTGGGCCTG
4921     ---------+---------+---------+---------+---------+---------+    4980
         GTCGTGGAAGAGACCAAGGACCCCGACGACCGCTCGGAGGAGAAGGATGACAACCCGGAC
          Q  H  L  L  W  F  L  G  L  L  A  S  L  L  F  L  L  L  G  L 4990                5010                5030
         GGGGTCTGGTACGCCTGGAGACGGGGAAATTTTTACAAGCTGAGAATGGGCGAATATTCA
4981     ---------+---------+---------+---------+---------+---------+    5040
         CCCCAGACCATGCGGACCTCTGCCCCTTTAAAAATGTTCGACTCTTACCCGCTTATAAGT
          G  V  W  Y  A  W  R  R  G  N  F  Y  K  L  R  M  G  E  Y  S
```

FIGURE 3M

```
              5050                5070                 5090
                 .                   .                    .
       gtagagatggtatctcggaaggaaaccacgcagatgtccactgaccaggaagaagttact
5041   ---------+---------+---------+---------+---------+---------+   5100
       catctctaccatagagccttcctttggtgcgtctacaggtgactggtccttcttcaatga
       V  E  M  V  S  R  K  E  T  T  Q  M  S  T  D  Q  E  E  V  T 5110                5130                 5150
                 .                   .                    .
       ggaatcggtgatgatgcgggctctgtgaaccaggcggcatttgatcctgcccacctctgt
5101   ---------+---------+---------+---------+---------+---------+   5160
       ccttagccactactacgcccgagacacttggtccgccgtaaactaggacgggtggagaca
       G  I  G  D  D  A  G  S  V  N  Q  A  A  F  D  P  A  H  L  C 5170                5190
                 .                   .
       gaaaacacacagtctgtGaaaagcacagtctga
5161   ---------+---------+---------+---   5193
       cttttgtgtgtcagacaCttttcgtgtcagact
       E  N  T  Q  S  V  K  S  T  V  *
```

FIGURE 4A

```
            10                    30                    50
             .                     .                     .
    atggacttcctgctcctgctcctcctcctggcttcatccgctctagcaggcctggcctcg
 1  ---------+---------+---------+---------+---------+---------+   60
    tacctgaaggacgaggacgaggaggaggaccgaagtaggcgagatcgtccggaccggagc
     M  D  F  L  L  L  L  L  A  S  S  A  L  A  G  L  A  S 70                    90                   110
             .                     .                     .
    tggacggtttccaaccccgagaccgtgcagggcatcaagggctcctgcctcatcatcccc
 61 ---------+---------+---------+---------+---------+---------+  120
    acctgccaaaggttggggctctggcacgtcccgtagttcccgaggacggagtagtagggg
     W  T  V  S  N  P  E  T  V  Q  G  I  K  G  S  C  L  I  I  P 130                   150                   170
             .                     .                     .
    tgcaccttcggcttcccggccaacgtggaggtgccccatggcatcacagccatctggtac
121 ---------+---------+---------+---------+---------+---------+  180
    acgtggaagccgaagggccggttgcacctccacggggtaccgtagtgtcggtagaccatg
     C  T  F  G  F  P  A  N  V  E  V  P  H  G  I  T  A  I  W  Y 190                   210                   230
             .                     .                     .
    tatgactactcaggcaagcgcctggtagtgagccactccaggaacccaaaggtggtggag
181 ---------+---------+---------+---------+---------+---------+  240
    atactgatgagtccgttcgcggaccatcactcggtgaggtccttgggttttccaccacctc
     Y  D  Y  S  G  K  R  L  V  V  S  H  S  R  N  P  K  V  V  E 250                   270                   290
             .                     .                     .
    aaccacttccaagaccgggccctgctgttgGGGCAGGTTGAGCAGAGGACGTGCAGCCTG
241 ---------+---------+---------+---------+---------+---------+  300
    ttggtgaaggttctggcccgggacgacaacCCCGTCCAACTCGTCTCCTGCACGTCGGAC
     N  H  F  Q  D  R  A  L  L  L  G  Q  V  E  Q  R  T  C  S  L 310                   330                   350
             .                     .                     .
    CTGCTGAAGGACCTGCAGCCCCAGGACTCGGGCTCCTATAACTTCCGCTTTGAGATCAGC
301 ---------+---------+---------+---------+---------+---------+  360
    GACGACTTCCTGGACGTCGGGGTCCTGAGCCCGAGGATATTGAAGGCGAAACTCTAGTCG
     L  L  K  D  L  Q  P  Q  D  S  G  S  Y  N  F  R  F  E  I  S 370                   390                   410
             .                     .                     .
    GAGGGCAACCGCTGGTCAGATGTCAAAGGCACAGTTGTCACCGTGACAGAGGTGCCCAGC
361 ---------+---------+---------+---------+---------+---------+  420
    CTCCCGTTGGCGACCAGTCTACAGTTTCCGTGTCAACAGTGGCACTGTCTCCACGGGTCG
     E  G  N  R  W  S  D  V  K  G  T  V  V  T  V  T  E  V  P  S
```

FIGURE 4B

```
              430                 450                 470
    GTGCCCACCATTGCCTTGCCAGCCAAGCTGCATGAGGGCATGGAGGTGGACTTCAACTGC
421 ---------+---------+---------+---------+---------+---------+ 480
    CACGGGTGGTAACGGAACGGTCGGTTCGACGTACTCCCGTACCTCCACCTGAAGTTGACG
     V  P  T  I  A  L  P  A  K  L  H  E  G  M  E  V  D  F  N  C 490                 510                 530
    TCCACTCCCTATGTGTGCCCGACGGAGCCGGTCAACCTACAGTGGCAAGGCCAGGATCCC
481 ---------+---------+---------+---------+---------+---------+ 540
    AGGTGAGGGATACACACGGGCTGCCTCGGCCAGTTGGATGTCACCGTTCCGGTCCTAGGG
     S  T  P  Y  V  C  P  T  E  P  V  N  L  Q  W  Q  G  Q  D  P 550                 570                 590
    ACCCGCTCCGTCACCTCCCACCTCCAGAAGCTTGAGCCCTCGGGCACCAGCCACATGGAG
541 ---------+---------+---------+---------+---------+---------+ 600
    TGGGCGAGGCAGTGGAGGGTGGAGGTCTTCGAACTCGGGAGCCCGTGGTCGGTGTACCTC
     T  R  S  V  T  S  H  L  Q  K  L  E  P  S  G  T  S  H  M  E 610                 630                 650
    ACCCTGCACATGGCCCTGTCCTGGCAGGACCATGGCCGGATCCTGAGCTGCCAGGTCTCA
601 ---------+---------+---------+---------+---------+---------+ 660
    TGGGACGTGTACCGGGACAGGACCGTCCTGGTACCGGCCTAGGACTCGACGGTCCAGAGT
     T  L  H  M  A  L  S  W  Q  D  H  G  R  I  L  S  C  Q  V  S 670                 690                 710
    GCAGCCGAACGCAGGATGCAGAAGGAGATTCACCTCCAAGTGCAGTATGCCCCCAAGGGT
661 ---------+---------+---------+---------+---------+---------+ 720
    CGTCGGCTTGCGTCCTACGTCTTCCTCTAAGTGGAGGTTCACGTCATACGGGGGTTCCCA
     A  A  E  R  R  M  Q  K  E  I  H  L  Q  V  Q  Y  A  P  K  G 730                 750                 770
    GTGGAGATCCTTTTTCAGCCACTCCGGACGGAACGTCCTTCCAGGTGATCTGGTCACCCTC
721 ---------+---------+---------+---------+---------+---------+ 780
    CACCTCTAGGAAAAGTCGGTGAGGCCTGCCTTGCAGGAAGGTCCACTAGACCAGTGGGAG
     V  E  I  L  F  S  H  S  G  R  N  V  L  P  G  D  L  V  T  L 790                 810                 830
    AGCTGCCAGGTGAATAGCAGCAACCCTCAGATCAGTTCCGTGCAGTGGGTCAAGGATGGG
781 ---------+---------+---------+---------+---------+---------+ 840
    TCGACGGTCCACTTATCGTCGTTGGGAGTCTAGTCAAGGCACGTCACCCAGTTCCTACCC
     S  C  Q  V  N  S  S  N  P  Q  I  S  S  V  Q  W  V  K  D  G
```

FIGURE 4C

```
              850              870              890
              .                .                .
     ACGAAGCTCAAAGACCAGAAACGTGTACTGCAGTTGCGCCGGGCAGCCTGGGCTGATGCT
841  ---------+---------+---------+---------+---------+---------+  900
     TGCTTCGAGTTTCTGGTCTTTGCACATGACGTCAACGCGGCCCGTCGGACCCGACTACGA
      T  K  L  K  D  Q  K  R  V  L  Q  L  R  R  A  A  W  A  D  A 910              930              950
              .                .                .
     GGCGTCTACACCTGCCAAGCCGGGAATGCCGTGGGCTCTTCAGTCTCACCCCCGGTCAGC
901  ---------+---------+---------+---------+---------+---------+  960
     CCGCAGATGTGGACGGTTCGGCCCTTACGGCACCCGAGAAGTCAGAGTGGGGGCCAGTCG
      G  V  Y  T  C  Q  A  G  N  A  V  G  S  S  V  S  P  P  V  S 970              990              1010
              .                .                .
     CTCCACGTCTTCATGGCTGAGGTCCAGGTAAGCCCTGTGGGCTCCATCCTGGAGAACCAG
961  ---------+---------+---------+---------+---------+---------+  1020
     GAGGTGCAGAAGTACCGACTCCAGGTCCATTCGGGACACCCGAGGTAGGACCTCTTGGTC
      L  H  V  F  M  A  E  V  Q  V  S  P  V  G  S  I  L  E  N  Q 1030             1050             1070
              .                .                .
     ACGGTGACGCTGGCCTGCAATACACCTAAGGAAGCGCCCAGCGAGCTGCGCTACAGCTGG
1021 ---------+---------+---------+---------+---------+---------+  1080
     TGCCACTGCGACCGGACGTTATGTGGATTCCTTCGCGGGTCGCTCGACGCGATGTCGACC
      T  V  T  L  A  C  N  T  P  K  E  A  P  S  E  L  R  Y  S  W 1090             1110             1130
              .                .                .
     TACAAGAACCACGCCCTCCTGGAGGGCTCTCACAGCCGCACCCTCCGGCTGCACTCAGTC
1081 ---------+---------+---------+---------+---------+---------+  1140
     ATGTTCTTGGTGCGGGAGGACCTCCCGAGAGTGTCGGCGTGGGAGGCCGACGTGAGTCAG
      Y  K  N  H  A  L  L  E  G  S  H  S  R  T  L  R  L  H  S  V 1150             1170             1190
              .                .                .
     ACCAGGGCGGATTCGGGCTTCTACTTCTGCGAGGTGCAGAACGCCCGGGGCAGAGAGCGC
1141 ---------+---------+---------+---------+---------+---------+  1200
     TGGTCCCGCCTAAGCCCGAAGATGAAGACGCTCCACGTCTTGCGGGCCCCGTCTCTCGCG
      T  R  A  D  S  G  F  Y  F  C  E  V  Q  N  A  R  G  R  E  R 1210             1230             1250
              .                .                .
     TCTCCCCCTGTCAGCGTGGTGGTCAGCCACCCACCCCTCACCCCGGACCTAACTGCCTTC
1201 ---------+---------+---------+---------+---------+---------+  1260
     AGAGGGGGACAGTCGCACCACCAGTCGGTGGGTGGGGAGTGGGGCCTGGATTGACGGAAG
      S  P  P  V  S  V  V  V  S  H  P  P  L  T  P  D  L  T  A  F
```

FIGURE 4D

```
              1270                1290                1310
                 .                   .                   .
       CTGGAGACACAGGCGGGGCTGGTGGGCATCCTCCAATGCTCTGTGGTCAGCGAGCCCCCA
1261   ---------+---------+---------+---------+---------+---------+   1320
       GACCTCTGTGTCCGCCCCGACCACCCGTAGGAGGTTACGAGACACCAGTCGCTCGGGGGT
        L  E  T  Q  A  G  L  V  G  I  L  Q  C  S  V  V  S  E  P  P 1330                1350                1370
                 .                   .                   .
       GCTACTCTGGTGTTGTCACACGGGGGCCTCATCTTGACCTCTACCTCCGAGGAGGGTGAC
1321   ---------+---------+---------+---------+---------+---------+   1380
       CGATGAGACCACAACAGTGTGCCCCCGGAGTAGAACTGGAGATGGAGGCTCCTCCCACTG
        A  T  L  V  L  S  H  G  G  L  I  L  T  S  T  S  E  G  D 1390                1410                1430
                 .                   .                   .
       CACAGCCCACGCTTCAGTGTCACCTCTGCCCCCAACTCCCTGCGCCTGGAGATTCAAGAC
1381   ---------+---------+---------+---------+---------+---------+   1440
       GTGTCGGGTGCGAAGTCACAGTGGAGACGGGGGTTGAGGGACGCGGACCTCTAAGTTCTG
        H  S  P  R  F  S  V  T  S  A  P  N  S  L  R  L  E  I  Q  D 1450                1470                1490
                 .                   .                   .
       CTGGGGCCAACAGACAGTGGGGAATACATGTGCTCAGCCAGCAGTTCTCTTGGGAATGCG
1441   ---------+---------+---------+---------+---------+---------+   1500
       GACCCCGGTTGTCTGTCACCCCTTATGTACACGAGTCGGTCGTCAAGAGAACCCTTACGC
        L  G  P  T  D  S  G  E  Y  M  C  S  A  S  S  S  L  G  N  A 1510                1530                1550
                 .                   .                   .
       TCCTCCACCCTGGACTTCCATGCCAATGCAGCCCGCCTCCTCATCAGCCCAGCAGCAGAG
1501   ---------+---------+---------+---------+---------+---------+   1560
       AGGAGGTGGGACCTGAAGGTACGGTTACGTCGGGCGGAGGAGTAGTCGGGTCGTCGTCTC
        S  S  T  L  D  F  H  A  N  A  A  R  L  L  I  S  P  A  A  E 1570                1590                1610
                 .                   .                   .
       GTGGTGGAAGGGCAGGCGGTGACACTGAGCTGCAGGAGCAGCCTGAGCCTGATGCCTGAC
1561   ---------+---------+---------+---------+---------+---------+   1620
       CACCACCTTCCCGTCCGCCACTGTGACTCGACGTCCTCGTCGGACTCGGACTACGGACTG
        V  V  E  G  Q  A  V  T  L  S  C  R  S  S  L  S  L  M  P  D 1630                1650                1670
                 .                   .                   .
       ACCCGTTTTTCCTGGTACCTGAACGGGGCCCTGATTCTCGAGGGGCCCAGCAGCAGCCTC
1621   ---------+---------+---------+---------+---------+---------+   1680
       TGGGCAAAAAGGACCATGGACTTGCCCCGGGACTAAGAGCTCCCCGGGTCGTCGTCGGAG
        T  R  F  S  W  Y  L  N  G  A  L  I  L  E  G  P  S  S  L
```

FIGURE 4E

```
              1690                1710                1730
                 .                   .                   .
       CTGCTCCCAGCAGCCTCCAGCACAGATGCCGGCTCATACCACTGCCGGGCCCAGAACAGC
1681   ---------+---------+---------+---------+---------+---------+   1740
       GACGAGGGTCGTCGGAGGTCGTGTCTACGGCCGAGTATGGTGACGGCCCGGGTCTTGTCG
        L  L  P  A  A  S  S  T  D  A  G  S  Y  H  C  R  A  Q  N  S 1750                1770                1790
                 .                   .                   .
       CACAGCACCAGCGGGCCCTCCTCACCTGCTGTTCTCACCGTGCTCTACGCCCCACGCCAG
1741   ---------+---------+---------+---------+---------+---------+   1800
       GTGTCGTGGTCGCCCGGGAGGAGTGGACGACAAGAGTGGCACGAGATGCGGGGTGCGGTC
        H  S  T  S  G  P  S  S  P  A  V  L  T  V  L  Y  A  P  R  Q 1810                1830                1850
                 .                   .                   .
       CCCGTGTTCACTGCCCAGCTGGACCCTGATACTGCAGGAGCTGGGGCCGGACGCCAAGGC
1801   ---------+---------+---------+---------+---------+---------+   1860
       GGGCACAAGTGACGGGTCGACCTGGGACTATGACGTCCTCGACCCCGGCCTGCGGTTCCG
        P  V  F  T  A  Q  L  D  P  D  T  A  G  A  G  R  Q  G 1870                1890                1910
                 .                   .                   .
       CTCCTCTTGTGCCGTGTGGACAGCGACCCCCCAGCCCAGCTGCAGCTGCTCCACAGGGGC
1861   ---------+---------+---------+---------+---------+---------+   1920
       GAGGAGAACACGGCACACCTGTCGCTGGGGGGTCGGGTCGACGTCGACGAGGTGTCCCCG
        L  L  L  C  R  V  D  S  D  P  P  A  Q  L  Q  L  L  H  R  G 1930                1950                1970
                 .                   .                   .
       CGTGTTGTGGCCTCTTCTCTGTCATGGGGGGGCGGCTGCTGCACCTGCGGAGGCTGTTTC
1921   ---------+---------+---------+---------+---------+---------+   1980
       GCACAACACCGGAGAAGAGACAGTACCCCCCCGCCGACGACGTGGACGCCTCCGACAAAG
        R  V  V  A  S  S  L  S  W  G  G  G  C  T  C  G  G  C  F 1990                2010                2030
                 .                   .                   .
       CACCGCATGAAGGTCACCAAAGCACCCAACCTACTGCGTGTAGAGATCCGAGACCCGGTG
1981   ---------+---------+---------+---------+---------+---------+   2040
       GTGGCGTACTTCCAGTGGTTTCGTGGGTTGGATGACGCACATCTCTAGGCTCTGGGCCAC
        H  R  M  K  V  T  K  A  P  N  L  L  R  V  E  I  R  D  P  V 2050                2070                2090
                 .                   .                   .
       CTGGAGGATGAGGGTGTGTACCTGTGCGAGGCCAGCAGCACCCTGGGCAACGCCTCCGCC
2041   ---------+---------+---------+---------+---------+---------+   2100
       GACCTCCTACTCCCACACATGGACACGCTCCGGTCGTCGTGGGACCCGTTGCGGAGGCGG
        L  E  D  E  G  V  Y  L  C  E  A  S  S  T  L  G  N  A  S  A
```

FIGURE 4F

```
            2110                2130                2150
             .                   .                   .
       TCTGCAACCTTGGATGCCCAGGCCACTGTCCTGGTCATCACACCGTCACACACGCTGCAG
2101   ---------+---------+---------+---------+---------+---------+   2160
       AGACGTTGGAACCTACGGGTCCGGTGACAGGACCAGTAGTGTGGCAGTGTGTGCGACGTC
        S  A  T  L  D  A  Q  A  T  V  L  V  I  T  P  S  H  T  L  Q 2170                2190                2210
             .                   .                   .
       GAAGGCATTGAAGCCAACCTGATTTGCAACGTGAGCCGTGAAGCCAGCGGCCCTGCCAAC
2161   ---------+---------+---------+---------+---------+---------+   2220
       CTTCCGTAACTTCGGTTGGACTAAACGTTGCACTCGGCACTTGGGTCGCCGGGACGGTTG
        E  G  I  E  A  N  L  I  C  N  V  S  R  E  A  S  G  P  A  N 2230                2250                2270
             .                   .                   .
       TTCTCCTGGTTCCGAGATGGGGCGCTATGGGCCCAGGGCCCTCTGGACACCGTGACACTG
2221   ---------+---------+---------+---------+---------+---------+   2280
       AAGAGGACCAAGGCTCTACCCCGCGATACCCGGGTCCCGGGAGACCTGTGGCACTGTGAC
        F  S  W  F  R  D  G  A  L  W  A  Q  G  P  L  D  T  V  T  L 2290                2310                2330
             .                   .                   .
       CTACCTGTGGCCAGAACTGATGCTGCCCTCTATGCTTGCCGCATCGTCACCGAGGCTGGT
2281   ---------+---------+---------+---------+---------+---------+   2340
       GATGGACACCGGTCTTGACTACGACGGGAGATACGAACGGCGTAGCAGTGGCTCCGACCA
        L  P  V  A  R  T  D  A  A  L  Y  A  C  R  I  V  T  E  A  G 2350                2370                2390
             .                   .                   .
       GCTGGCCTCTCCACCCCTGTGGCCCTGAATGTGCTCTATCCCCCCGATCCTCCAAAGTTG
2341   ---------+---------+---------+---------+---------+---------+   2400
       CGACCGGAGAGGTGGGGACACCGGGACTTACACGAGATAGGGGGGCTAGGAGGTTTCAAC
        A  G  L  S  T  P  V  A  L  N  V  L  Y  P  P  D  P  P  K  L 2410                2430                2450
             .                   .                   .
       TCAGCCCTCCTGGACGTGGACCAGGGCCACACGGCTGTGTTCGTCTGTACTGTGGACAGT
2401   ---------+---------+---------+---------+---------+---------+   2460
       AGTCGGGAGGACCTGCACCTGGTCCCGGTGTGCCGACACAAGCAGACATGACACCTGTCA
        S  A  L  L  D  V  D  Q  G  H  T  A  V  F  V  C  T  V  D  S 2470                2490                2510
             .                   .                   .
       CGCCCTCTTGCCCAGTTGGCCCTGTTCCGTGGGGAACACCTCCTGGCCGCCAGCTCGGCA
2461   ---------+---------+---------+---------+---------+---------+   2520
       GCGGGAGAACGGGTCAACCGGGACAAGGCACCCCTTGTGGAGGACCGGCGGTCGAGCCGT
        R  P  L  A  Q  L  A  L  F  R  G  E  H  L  L  A  A  S  S  A
```

FIGURE 4G

```
                   2530                2550                2570
                     .                   .                   .
         CTCCGGCTCCCCCCTCGTGGCCGCCTCCAGGCCAAAGCCTCGGCCAACTCCTTGCAGCTA
2521     ---------+---------+---------+---------+---------+---------+    2580
         GAGGCCGAGGGGGGAGCACCGGCGGAGGTCCGGTTTCGGAGCCGGTTGAGGAACGTCGAT
          L  R  L  P  P  R  G  R  L  Q  A  K  A  S  A  N  S  L  Q  L 2590                2610                2630
                     .                   .                   .
         GAGGTCCGAGACTTGAGCCTTGGGGACTCTGGCAGCTACCACTGTGAGGCCACCAACATC
2581     ---------+---------+---------+---------+---------+---------+    2640
         CTCCAGGCTCTGAACTCGGAACCCCTGAGACCGTCGATGGTGACACTCCGGTGGTTGTAG
          E  V  R  D  L  S  L  G  D  S  G  S  Y  H  C  E  A  T  N  I 2650                2670                2690
                     .                   .                   .
         CTTGGATCAGCCAACACTTCTCTTACCTTCCAGGTCCGAGGAGCCTGGGTCCGGGTGTCA
2641     ---------+---------+---------+---------+---------+---------+    2700
         GAACCTAGTCGGTTGTGAAGAGAATGGAAGGTCCAGGCTCCTCGGACCCAGGCCCACAGT
          L  G  S  A  N  T  S  L  T  F  Q  V  R  G  A  W  V  R  V  S 2710                2730                2750
                     .                   .                   .
         CCGTCGCCTGAGCTCCAGGAGGGCCAGGCTGTGGTCCTGAGCTGCCAGGTACCCATAGGG
2701     ---------+---------+---------+---------+---------+---------+    2760
         GGCAGCGGACTCGAGGTCCTCCCGGTCCGACACCAGGACTCGACGGTCCATGGGTATCCC
          P  S  P  E  L  Q  E  G  Q  A  V  V  L  S  C  Q  V  P  I  G 2770                2790                2810
                     .                   .                   .
         GTCCTGGAGGGGACCTCATATCGTTGGTATCGGGATGGCCAGCCCCTCCAGGAGTCCACT
2761     ---------+---------+---------+---------+---------+---------+    2820
         CAGGACCTCCCCTGGAGTATAGCAACCATAGCCCTACCGGTCGGGGAGGTCCTCAGGTGA
          V  L  E  G  T  S  Y  R  W  Y  R  D  G  Q  P  L  Q  E  S  T 2830                2850                2870
                     .                   .                   .
         TCGGCCACGCTCCGTTTTGCAGCCATAACTCTGAGCCAGGCTGGAGCCTACCATTGCCAA
2821     ---------+---------+---------+---------+---------+---------+    2880
         AGCCGGTGCGAGGCAAAACGTCGGTATTGAGACTCGGTCCGACCTCGGATGGTAACGGTT
          S  A  T  L  R  F  A  A  I  T  L  S  Q  A  G  A  Y  H  C  Q 2890                2910                2930
                     .                   .                   .
         GCCCAAGCTCCAGGCTCAGCCACCACGGACCTGGCTGCCCCTGTCAGCCTCCACGTGACC
2881     ---------+---------+---------+---------+---------+---------+    2940
         CGGGTTCGAGGTCCGAGTCGGTGGTGCCTGGACCGACGGGGACAGTCGGAGGTGCACTGG
          A  Q  A  P  G  S  A  T  T  D  L  A  A  P  V  S  L  H  V  T
```

FIGURE 4H

```
              2950                2970                2990
                .                  .                  .
       TACGCACCTCGCCAGGCCACACTCACCACCCTGATGGACTCAGGCCTCGGGCGACTGGGC
2941   ---------+---------+---------+---------+---------+---------+   3000
       ATGCGTGGAGCGGTCCGGTGTGAGTGGTGGGACTACCTGAGTCCGGAGCCCGCTGACCCG
        Y  A  P  R  Q  A  T  L  T  T  L  M  D  S  G  L  G  R  L  G 3010                3030                3050
                .                  .                  .
       CTCCTTCTGTGCCGTGTGAACAGTGACCCTCCTGCCCAGCTCCGACTGCTCCATGGGAGC
3001   ---------+---------+---------+---------+---------+---------+   3060
       GAGGAAGACACGGCACACTTGTCACTGGGAGGACGGGTCGAGGCTGACGAGGTACCCTCG
        L  L  L  C  R  V  N  S  D  P  P  A  Q  L  R  L  L  H  G  S 3070                3090                3110
                .                  .                  .
       CGCCTCGTGGCCTCTACTCTACAAGGTGTGGAGGAGCTTGCAGGCAGCTCTCCCCGCCTA
3061   ---------+---------+---------+---------+---------+---------+   3120
       GCGGAGCACCGGAGATGAGATGTTCCACACCTCCTCGAACGTCCGTCGAGAGGGGCGGAT
        R  L  V  A  S  T  L  Q  G  V  E  E  L  A  G  S  S  P  R  L 3130                3150                3170
                .                  .                  .
       CAGGTGGCCACAGCCCCCAACACGCTGCGCCTGGAGATCCACAACGCAGTGCTGGAGGAT
3121   ---------+---------+---------+---------+---------+---------+   3180
       GTCCACCGGTGTCGGGGGTTGTGCGACGCGGACCTCTAGGTGTTGCGTCACGACCTCCTA
        Q  V  A  T  A  P  N  T  L  R  L  E  I  H  N  A  V  L  E  D 3190                3210                3230
                .                  .                  .
       GAAGGCGTCTACACCTGCGAGGCCACCAACACCCTGGGTCAGACCTTGGCCTCCGCCGCC
3181   ---------+---------+---------+---------+---------+---------+   3240
       CTTCCGCAGATGTGGACGCTCCGGTGGTTGTGGGACCCAGTCTGGAACCGGAGGCGGCGG
        E  G  V  Y  T  C  E  A  T  N  T  L  G  Q  T  L  A  S  A  A 3250                3270                3290
                .                  .                  .
       TTCGATGCCCAGGCTATGAGAGTGCAGGTGTGGCCCAATGCCACCGTGCAAGAGGGGCAG
3241   ---------+---------+---------+---------+---------+---------+   3300
       AAGCTACGGGTCCGATACTCTCACGTCCACACCGGGTTACGGTGGCACGTTCTCCCCGTC
        F  D  A  Q  A  M  R  V  Q  V  W  P  N  A  T  V  Q  E  G  Q 3310                3330                3350
                .                  .                  .
       CTGGTGAACCTGACCTGCCTTGTATGGACCACGCACCTGGCCCAGCTCACCTACACATGG
3301   ---------+---------+---------+---------+---------+---------+   3360
       GACCACTTGGACTGGACGGAACATACCTGGTGCGTGGACCGGGTCGAGTGGATGTGTACC
        L  V  N  L  T  C  L  V  W  T  T  H  L  A  Q  L  T  Y  T  W
```

FIGURE 4I

```
              3370                3390                3410
                 .                   .                   .
       TACCGAGACCAGCAGCAGCTCCCAGGTGCTGCCCACTCCATCCTCCTGCCCAATGTCACT
3361   ---------+---------+---------+---------+---------+---------+   3420
       ATGGCTCTGGTCGTCGTCGAGGGTCCACGACGGGTGAGGTAGGAGGACGGGTTACAGTGA
        Y  R  D  Q  Q  Q  L  P  G  A  A  H  S  I  L  L  P  N  V  T 3430                3450                3470
                 .                   .                   .
       GTCACAGATGCCGCCTCCTACCGCTGTGGCATATTGATCCCTGGCCAGGCACTCCGCCTC
3421   ---------+---------+---------+---------+---------+---------+   3480
       CAGTGTCTACGGCGGAGGATGGCGACACCGTATAACTAGGGACCGGTCCGTGAGGCGGAG
        V  T  D  A  A  S  Y  R  C  G  I  L  I  P  G  Q  A  L  R  L 3490                3510                3530
                 .                   .                   .
       TCCAGACCTGTCGCCCTGGATGTCCTCTACGCACCCCGCAGACTGCGCCTGACCCATCTC
3481   ---------+---------+---------+---------+---------+---------+   3540
       AGGTCTGGACAGCGGGACCTACAGGAGATGCGTGGGGCGTCTGACGCGGACTGGGTAGAG
        S  R  P  V  A  L  D  V  L  Y  A  P  R  R  L  R  L  T  H  L 3550                3570                3590
                 .                   .                   .
       TTGGAGAGCCGTGGTGGGCAGCTGGCCGTGGTGCTGTGCACTGTGGACAGTCGCCCAGCT
3541   ---------+---------+---------+---------+---------+---------+   3600
       AACCTCTCGGCACCACCCGTCGACCGGCACCACGACACGTGACACCTGTCAGCGGGTCGA
        L  E  S  R  G  G  Q  L  A  V  V  L  C  T  V  D  S  R  P  A 3610                3630                3650
                 .                   .                   .
       GCCCAGCTGACCCTCAGCCATGCTGGCCGCCTCCTGGCCTCCTCAACCGCAGCCTCTGTC
3601   ---------+---------+---------+---------+---------+---------+   3660
       CGGGTCGACTGGGAGTCGGTACGACCGGCGGAGGACCGGAGGAGTTGGCGTCGGAGACAG
        A  Q  L  T  L  S  H  A  G  R  L  L  A  S  S  T  A  A  S  V 3670                3690                3710
                 .                   .                   .
       CCCAACACCCTGCGCCTGGAGCTGTGGGAGCCCCGGCCCAGTGATGAGGGTCTCTACAGC
3661   ---------+---------+---------+---------+---------+---------+   3720
       GGGTTGTGGGACGCGGACCTCGACACCCTCGGGGCCGGGTCACTACTCCCAGAGATGTCG
        P  N  T  L  R  L  E  L  W  E  P  R  P  S  D  E  G  L  Y  S 3730                3750                3770
                 .                   .                   .
       TGCTCGGCCCGCAGTCCTCTGGGCCAGGCCAACACATCCCTGGAGCTGCGGCTAGAGGGC
3721   ---------+---------+---------+---------+---------+---------+   3780
       ACGAGCCGGGCGTCAGGAGACCCGGTCCGGTTGTGTAGGGACCTCGACGCCGATCTCCCG
        C  S  A  R  S  P  L  G  Q  A  N  T  S  L  E  L  R  L  E  G
```

FIGURE 4J

```
             3790                3810                3830
              .                   .                   .
         GTGCAGGTGACACTGGCTCCATCGACCACTGTGCCGGAGGGGGCCCCTGTCACAGTGACC
3781     ---------+---------+---------+---------+---------+---------+     3840
         CACGTCCACTGTGACCGAGGTAGCTGGTGACACGGCCTCCCCCGGGGACAGTGTCACTGG
          V  Q  V  T  L  A  P  S  T  T  V  P  E  G  A  P  V  T  V  T 3850                3870                3890
              .                   .                   .
         TGTGAAGACCCTGCTGCCCGCCCACCCACCCTCTATGTCTGGTACCACAACAGCCGTTGG
3841     ---------+---------+---------+---------+---------+---------+     3900
         ACACTTCTGGGACGACGGGCGGGTGGGTGGGAGATACAGACCATGGTGTTGTCGGCAACC
          C  E  D  P  A  A  R  P  P  T  L  Y  V  W  Y  H  N  S  R  W 3910                3930                3950
              .                   .                   .
         CTGCAGGAGGGGTCGGCTGCCTCCCTCTCGTTTCCAGCGGCTACACGGGCTCACGCGGGC
3901     ---------+---------+---------+---------+---------+---------+     3960
         GACGTCCTCCCCAGCCGACGGAGGGAGAGCAAAGGTCGCCGATGTGCCCGAGTGCGCCCG
          L  Q  E  G  S  A  A  S  L  S  F  P  A  A  T  R  A  H  A  G 3970                3990                4010
              .                   .                   .
         GCCTATACCTGCCAGGTCCAGGATGCCCAGGGCACACGCATCTCCCAGCCCGCAGCACTG
3961     ---------+---------+---------+---------+---------+---------+     4020
         CGGATATGGACGGTCCAGGTCCTACGGGTCCCGTGTGCGTAGAGGGTCGGGCGTCGTGAC
          A  Y  T  C  Q  V  Q  D  A  Q  G  T  R  I  S  Q  P  A  A  L 4030                4050                4070
              .                   .                   .
         CACATCCTCTATGCCCCTCGGGATGctgtcctttcctccttctgggactcaagggccagc
4021     ---------+---------+---------+---------+---------+---------+     4080
         GTGTAGGAGATACGGGGAGCCCTACgacaggaaaggaggaagaccctgagttcccggtcg
          H  I  L  Y  A  P  R  D  A  V  L  S  S  F  W  D  S  R  A  S 4090                4110                4130
              .                   .                   .
         cctatggccgtggtacagtgcactgtggacagcgagccacctgccgagatgaccctgtcc
4081     ---------+---------+---------+---------+---------+---------+     4140
         ggataccggcaccatgtcacgtgacacctgtcgctcggtggacggctctactgggacagg
          P  M  A  V  V  Q  C  T  V  D  S  E  P  P  A  E  M  T  L  S 4150                4170                4190
              .                   .                   .
         cgtgatggcaaggtgctggccaccagccatggggcccacggcttagcagtggggacaggc
4141     ---------+---------+---------+---------+---------+---------+     4200
         gcactaccgttccacgaccggtggtcggtaccccgggtgccgaatcgtcaccctgtccg
          R  D  G  K  V  L  A  T  S  H  G  A  H  G  L  A  V  G  T  G
```

FIGURE 4K

```
            4210               4230               4250
              .                  .                  .
      catgtccaggtggcccgcaacgccctgcagctgcgggtgcagaatgtgccctcacgtgac
4201  ---------+---------+---------+---------+---------+---------+  4260
      gtacaggtccaccgggcgttgcgggacgtcgacgcccacgtcttacacgggagtgcactg
      H  V  Q  V  A  R  N  A  L  Q  L  R  V  Q  N  V  P  S  R  D 4270               4290               4310
              .                  .                  .
      aaggacacctacgtctgcatggcccgcaactccttgggctcagtcagcaccatggggcag
4261  ---------+---------+---------+---------+---------+---------+  4320
      ttcctgtggatgcagacgtaccgggcgttgaggaacccgagtcagtcgtggtacccgtc
      K  D  T  Y  V  C  M  A  R  N  S  L  G  S  V  S  T  M  G  Q 4330               4350               4370
              .                  .                  .
      ctgcagccagaaggtgtgcacgtggtagccgagccagggctggatgtgcccgaaggcaca
4321  ---------+---------+---------+---------+---------+---------+  4380
      gacgtcggtcttccacacgtgcaccatcggctcggtcccgacctacacgggcttccgtgt
      L  Q  P  E  G  V  H  V  V  A  E  P  G  L  D  V  P  E  G  T 4390               4410               4430
              .                  .                  .
      gcgctgaaccctgagctgtcgcctccctagtggccctgggcacatgggcaactccacctt
4381  ---------+---------+---------+---------+---------+---------+  4440
      cgcgacttggactcgacagcggagggatcaccgggacccgtgtacccgttgaggtggaaa
      A  L  N  L  S  C  R  L  P  S  G  P  G  H  M  G  N  S  T  F 4450               4470               4490
              .                  .                  .
      gcttggttccggaacggtcggcagctacacacagagtctgtgcccaccccttaccttcacc
4441  ---------+---------+---------+---------+---------+---------+  4500
      cgaaccaaggccttgccagccgtcgatgtgtgtctcagacacgggtgggaatggaagtgg
      A  W  F  R  N  G  R  Q  L  H  T  E  S  V  P  T  L  T  F  T 4510               4530               4550
              .                  .                  .
      catgtggcccgcgcccaagctggcttgtaccactgccaggctgagctccccgccggggct
4501  ---------+---------+---------+---------+---------+---------+  4560
      gtacaccgggcgcgggttcgaccgaacatggtgacggtccgactcgaggggcggccccga
      H  V  A  R  A  Q  A  G  L  Y  H  C  Q  A  E  L  P  A  G  A 4570               4590               4610
              .                  .                  .
      gccacctctgctccagtcttgctccgggtgctctaccctcccaagacgcccaccatgact
4561  ---------+---------+---------+---------+---------+---------+  4620
      cggtggagacgaggtcagaacgaggcccacgagatgggagggttctgcggtggtactga
      A  T  S  A  P  V  L  L  R  V  L  Y  P  P  K  T  P  T  M  T
```

FIGURE 4L

```
              4630                4650                4670
               .                   .                   .
       gttttttgtggagcccgagggtggcatccagggcattctggactgccgagtggacagtgag
4621   ---------+---------+---------+---------+---------+---------+   4680
       caaaaacacctcgggctccaccgtaggtcccgtaagacctgacggctcacctgtcactc
        V  F  V  E  P  E  G  G  I  Q  G  I  L  D  C  R  V  D  S  E 4690                4710                4730
               .                   .                   .
       cccctagccagcctgaccctccacctgggcagtcggctggtggcctccagccagccccag
4681   ---------+---------+---------+---------+---------+---------+   4740
       ggggatcggtcggactgggaggtggacccgtcagccgaccaccggaggtcggtcggggtc
        P  L  A  S  L  T  H  L  G  S  R  L  V  A  S  S  Q  P  Q 4750                4770                4790
               .                   .                   .
       gctgcccctgccaagccgcacatccgcgtctcagccagtcccaatgcCTTGCGAGTGGAC
4741   ---------+---------+---------+---------+---------+---------+   4800
       cgacggggacggttcggcgtgtaggcgcagagtcggtcagggttacgGAACGCTCACCTG
        A  A  P  A  K  P  H  I  R  V  S  A  S  P  N  A  L  R  V  D 4810                4830                4850
               .                   .                   .
       ATGGAGGAGCTGAAGCCCAGTGACCAGGGGGAGTATGTGTGCTCGGCCTCCAATGCCCTG
4801   ---------+---------+---------+---------+---------+---------+   4860
       TACCTCCTCGACTTCGGGTCACTGGTCCCCCTCATACACACGAGCCGGAGGTTACGGGAC
        M  E  E  L  K  P  S  D  Q  G  E  Y  V  C  S  A  S  N  A  L 4870                4890                4910
               .                   .                   .
       GGCTCTGCCTCTGCTGCCACCTACTTCGGAACCAGAGCCCTGCATCGCCTGCATCTGTTC
4861   ---------+---------+---------+---------+---------+---------+   4920
       CCGAGACGGAGACGACGGTGGATGAAGCCTTGGTCTCGGGACGTAGCGGACGTAGACAAG
        G  S  A  S  A  A  T  Y  F  G  T  R  A  L  H  R  L  H  L  F 4930                4950                4970
               .                   .                   .
       CGGCACCTTCTCTGGTTCCTGGGGCTGCTGGCGAGCCTCCTCTTCCTACTGTTGGGCCTG
4921   ---------+---------+---------+---------+---------+---------+   4980
       GCCGTGGAAGAGACCAAGGACCCCGACGACCGCTCGGAGGAGAAGGATGACAACCCGGAC
        R  H  L  L  W  F  L  G  L  L  A  S  L  L  F  L  L  L  G  L 4990                5010                5030
               .                   .                   .
       GGGGTCTGGTACGCCTGGAGACGGGGAAATTTTCACAAGCTGAGAATGGGCGAATATTCA
4981   ---------+---------+---------+---------+---------+---------+   5040
       CCCCAGACCATGCGGACCTCTGCCCCTTTTAAAAGTGTTCGACTCTTACCCGCTTATAAGT
        G  V  W  Y  A  W  R  R  G  N  F  H  K  L  R  M  G  E  Y  S
```

FIGURE 4M

```
             5050                5070                5090
               .                   .                   .
         gtagagatggtatctcggaaggaaaccacgcagatgtccactgaccaggaagaagttact
5041     ---------+---------+---------+---------+---------+---------+    5100
         catctctaccatagagccttcctttggtgcgtctacaggtgactggtccttcttcaatga
         V  E  M  V  S  R  K  E  T  T  Q  M  S  T  D  Q  E  E  V  T 5110                5130                5150
               .                   .                   .
         ggaatcggtgatgatgcgggctctgtgaaccaggcggcatttgatcctgcccacctctgt
5101     ---------+---------+---------+---------+---------+---------+    5160
         ccttagccactactacgcccgagacacttggtccgccgtaaactaggacgggtggagaca
         G  I  G  D  D  A  G  S  V  N  Q  A  A  F  D  P  A  H  L  C 5170                5190
               .                   .
         gaaaacacacagtctgtGaaaagcacagtctga
5161     ---------+---------+---------+---    5193
         cttttgtgtgtcagacaCttttcgtgtcagact
         E  N  T  Q  S  V  K  S  T  V  *
```

NUCLEIC ACID ENCODING POLYPEPTIDE INVOLVED IN CELLULAR ENTRANCE OF THE PRRS VIRUS

PRIORITY CLAIM TO RELATED PATENT APPLICATIONS

This application is a continuation of U.S. application Ser. No. 10/485,045 filed Jan. 23, 2004, now U.S. Pat. No. 7,563,881, which is a national phase filing under 35 U.S.C. §371 of International Patent Application No. PCT/EP02/08047 (filed Jul. 18, 2002, and published on Feb. 6, 2003 as International Publication No. WO 03/010200), which, in turn, claims priority to European Patent Application Nos. 01202824.7 (filed Jul. 24, 2001) and 01204220.6 (filed Oct. 31, 2001); all of which are wholly incorporated by reference herein.

The present invention relates to a new polynucleotide that encodes a polypeptide involved in cellular entrance of the PRRS virus (PRRSV), to a recombinant vector comprising said polynucleotide, to a cell capable of expressing said polypeptide, a method of producing said polypeptide as well as to a cell culture and to a novel method of producing the PRRSV virus. The present invention further relates to a method of identifying compounds that affect the PRRSV receptor function of the polypeptide as well as to the use of the polypeptide or identified compounds in the manufacture of medicaments.

Porcine reproductive and respiratory syndrome (PRRS) was initially recognised in 1987 in the USA as a new disease of swine that causes reproductive failure in pregnant sows and respiratory failure in neonatal pigs. The disease was subsequently described In Europe and Canada. Until a causative agent had been identified the syndrome was known by various names, such as mystery swine disease, swine infertility and respiratory syndrome, blue eared pig disease, abortus blauw, etc.

An enveloped single-stranded RNA virus, the PRRS virus, causes the syndrome. PRRSV is a member of the Arterivirus family that includes lactate dehydrogenase-elevating virus LDV) of mice, equine arteritis virus (EAV), and simian hemorrhagic fever virus (SHFV).

The predominant cell type infected by PRRSV is the macrophage. The virus was first isolated in porcine alveolar macrophages (PAMs) but has also been reported to replicate in monocytes and in microglial cells. PRRSV has a restricted tropism for monocyte/macrophage cells both in vitro and in vivo.

Currently PRRSV replication only occurs in a few established cell lines.

Virus replication in vitro has been demonstrated in established cell lines such as monkey kidney cell line MA-104, and its permissive clone MARC-145 (Kim et al., Arch. Virol., 133, 477-483, 1993).

A process for growing PRRSV on an MA-104 derived cloned cell line, 9009B (designated as ATCC CRL 11302) is described in U.S. Pat. No. 5,510,258.

Failure of PRRSV replication in several other cell lines has been reported.

The mechanism that restricts PRRSV replication in a variety of cell lines has been investigated. It was found that PRRSV could not bind to most cell types tested. The absence of PRRSV binding to cells was suggested to be one of the determinants of PRRSV cell tropism. It was postulated that the absence of a specific cellular component might be crucial for virus entry, and that virus entry occurred by receptor mediated endocytosis (Kreutz, Virus Research, 53, 121-128, 1998.)

Receptor mediated endocytosis is known for other enveloped viruses. Receptors for some viruses have been reported. For example, the receptors for the different subgroups of avian sarcoma and leukosis virus (ASLV) have been identified and cloned. (Balliet et al., J. Virol., 73(4), 3054-3061, 1999.) The cellular receptor for mouse hepatitis virus (MHV) has also been identified and cloned. A vector into which the cDNA for the MHV receptor had been subcloned was used for expression of the MHV receptor in cells that were normally resistant to MHV infection (BHK line of hamster fibroblasts and the RD line of human rhabdomyosarcoma cells). This was sufficient to permit infection of these cells with MHV (Dveksler et al., J. Virology, 65(12), 6881-6891, 1991).

Some efforts to identify a PRRSV receptor have been reported as well.

In an attempt to identify the PAM receptor which may determine the susceptibility of macrophage to PRRSV two monoclonal antibodies (Mabs), 41D3 and 41D5, were produced that blocked PRRSV Infection of PAM. (Duan et al., in Coronaviruses and Arteriviruses, edited by Enjuanes et al, Plenum Press, New York, 81-87, 1998).

With the aid of these MAbs an attempt was made to identify the molecules which are used for virus attachment on the surface of PAM.

By using a protein biotinylation kit, all membrane proteins were labelled, and proteins from the biotinylated cell lysate were Immunoprecipitated using the MAbs. Thus, a biotin-labelled protein with a molecular weight of approximately 210 kDa could be visualised after immunoprecipitation (Duan et al., J. Virol., 4520-4523, 1998.)

However, so far a characterisation of the potential receptor for PRRSV has not been reported and its actual role in cell tropism has not been elucidated.

As already explained above, PRRSV can at present only be cultured in a limited number of cell lines.

For vaccine purposes, it would be convenient if the virus could be cultured in other cells than the limited number of cell lines available at present for culturing PRRSV. Only by changing the production process of PRRSV vaccines to other cell lines, the quality, quantity and the cost price of PRRSV vaccines can be improved.

A need for more efficient culturing methods for the virus therefore exists.

If indeed a PRRSV receptor is responsible for the unique cell specificity of the virus, expression of the receptor in cells that are normally non-permissive for the virus may open routes towards more efficient ways of culturing the virus.

The present inventors have succeeded in isolating a protein from PAM membranes that seems to play a crucial role in virus entry into the cell. The present inventors succeeded for the first time to identify and isolate the pure protein in large enough quantities for it to be analysed. By way of a unique process for the identification and isolation of the protein, the present inventors were thus the first to characterise the protein and to elucidate the amino acid sequence of the protein and the corresponding gene sequence.

The elucidated nucleotide sequence encoding the protein, as well as the amino acid sequence of the protein, were compared with sequences stored in sequence databases.

Surprisingly the putative PRRSV receptor provided by the present invention showed a great deal of homology to certain proteins belonging to the Siglec family. The siglec family is a family of sialic acid binding Imunnoglobulin (Ig)-like lectins.

The identified polypeptide showed 69% identity on the amino acid level and 75% identity on the nucleic acid level with a 185 kDa mouse sialoadhesin protein and its corresponding gene sequence respectively (GenBank Accession Code: Z36293, SwissProt annotated protein record: Q62230) as described by Crocker et al., EMBO J., 13(19), 4490-4503, 1994.

The polypeptide further showed 78% identity on the amino acid level and 82% identity on the nucleic acid level with a 200 kDa human sialoadhesin protein and its gene sequence respectively (GenBank accession code: AF230073), as described by Hartnell A et al., Blood, 97(1), 288-296, 2001.

Sequences were compared with sequences in databases using a BLAST program (BLASTF 2.1.2 [Oct. 19, 2000]) (Altschul, Stephen F., Thomas L. Madden, Alejandro A. Schaffer, Jinghui Zhang, Zheng Zhang, Webb Miller, and David J. Lipman (1997) "Gapped BLAST and PSI-BLAST: a new generation of protein database search programs", Nucleic Acids Res. 25, 3389-3402). The program was used to search for sequence alignments.

The mouse and human sialoadhesins show about 72% identity on the amino acid level and about 77% identity on the nucleic add level, with the greatest identity in the extracellular region, which comprises 17 lg domains in both species. The expression pattern of human sialoadhesin and mouse sialoadhesin is similar. They are absent from monocytes and other peripheral blood leukocytes, but expressed strongly by tissue macrophages in the spleen, lymph node, bone marrow, liver, colon and lungs.

Human sialoadhesin (Sn) is a macrophage-restricted cellular interaction molecule, likely to be involved in macrophage-hemopoietic cell interactions in the bone marrow and possibly also in other cell-cell interactions.

Human Sn is a prototypic member of the Siglec (sialic acid binding Ig-like lectin) family of cellular interaction molecules and was designated Siglec-I.

Apart from Sn, members of the Siglec family include CD22 (Siglec-2) on B-cells, CD33 (Siglec-3) on immature myeloid cells and monocytes, and myelin-associated glycoprotein (MAG) (Siglec-4A) on Schwann cells and oligodendrocytes, and Siglecs-5, -6, -7, -8 and expressed on various hemopoietic subsets. The biological functions of Sn are poorly understood.

Based on its % of identity with the above mentioned mouse- and human sialoadhesin, the identified polypeptide, that serves as the receptor for PRRSV on porcine alveolar macrophages, may be a porcine sialoadhesin (Sn).

The present Invention, in one aspect, provides an isolated polynucleotide comprising a nucleic acid sequence encoding a porcine polypeptide, or a functional fragment of said polypeptide, said polypeptide having the following characteristics:

said polypeptide is when expressed on the surface of a cell, capable of making the cell receptive for PRRSV, said polypeptide has an apparent molecular weight of approximately 210 kD and said polypeptide is reactive with Mab 41D3.

Hybridoma 41D3 producing this Mab is deposited at the CNCM of the Institute Pasteur, Paris, France, under accession no. I-2719.

The polynucleotide according to the invention encodes a polypeptide that plays a crucial role in entry of PRRSV into cells. Because the polypeptide mediates the entry of the virus into the cells, it is postulated that it is the PRRSV receptor from porcine aveolar macrophages.

Thus with the present invention polynucleotides are provided encoding an Sn like protein, that is a member of the super family of immunoglobulin-like molecules with the property that it facilitates the entry of PRRSV into a cell.

The Mab 41D3 specifically recognizes the identified polypeptide and blocks the entry of PRRSV into a cell. No membrane immunofluorescence staining with MAb 41D3 was observed on porcine peripheral blood mononuclear cells (PBMC), porcine peritoneal macrophages (PPM), ST (swine testis), SK (swine kidney), PK-15 and MARC-145 cells. Of these cells, only a faint intracellular staining was observed in some PBMC and PPM.

The polypeptide as identified has an apparent molecular weight of approximately 210 kD. The molecular weight was determined in SDS-PAGE using reducing conditions. The term "approximately" should be interpreted as meaning that the molecular weight Is over 200 kD (closest marker in the gel) and in the range between 205 and 225 kD.

The sequence of the polynucleotide, as it was elucidated, by the present inventors is depicted in SEQ ID NO.: 1. The sequence of the polypeptide encoded by this polynucleotide is depicted in SEQ ID No.: 2. The sequence information as provided herein should not be so narrowly construed as to require exclusion of erroneously identified bases or natural occurring variations of the nucleotide sequence in the pig population.

Fragments of the provided nucleic acid sequence that encode a functional fragment of the polypeptide are likewise part of the present invention. A functional fragment of the polypeptide is a fragment that at least represents the part of the polypeptide, which Is essential for the polypeptide to be able to serve as a receptor for PRRSV, and can fulfill this function, for example, when used alone or fused to heterologous sequences.

Thus, such polynucleotides, encoding functional fragments, may encode polypeptides that are functional per se, or the fragments may be functional when linked to other polypeptides, to obtain chimeric proteins.

For example, a polynucleotide encoding such a functional fragment of the polypeptide, may be fused to polynucleotides encoding transmembrane regions and/or signal sequences. By creating such chimeric proteins the functional site can be transferred to more abundant cell surface proteins creating cells with a higher sensitivity for PRRSV. Alternatively, to enhance the sensitivity of cells for PRRSV, multiple functional domains can be created on a single molecule or spacers of optimal length can be placed between the transmembrane region and the functional PRRSV binding site.

The polynucleotides encoding fragments of the complete polypeptides, preferably encode fragments being at least 50 amino acids, more preferred at least 100 amino acids or at least 200 amino acids in length.

Polynucleotides according to the invention also encompass those polynucleotides that encoding variants of the identified polypeptide. With variants of the identified polypeptide, polypeptides are meant that have a PRRSV receptor activity and comprise variations of the identified amino acid sequence while still maintaining functional characteristics, in that they still play a role in viral entry of PRRSV into cells. Thus these variants are functionally equivalent to a polypeptide with the identified amino acid sequence. These polypeptides do not necessarily encompass the full length amino acid sequence as provided herein.

Variations that can occur in an amino acid sequence may be demonstrated by (an) amino acid difference(s) in the overall sequence or by deletions, substitutions, insertions, inversions or additions of (an) amino acid(s) in said sequence. Amino acid substitutions that are expected not to essentially alter biological and immunological activities have been described. Amino acid replacements between related amino adds or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science, 1985 227, 1435-1441) and determining the functional similarity between homologous polypeptides. It will be clear that polynucleotides encoding such variants are likewise part of the invention.

Polynucleotides as defined with the present invention also include polynucleotides having variations in the nucleic acid sequence when compared to the identified nucleic acid sequence or having polymorphic sites. With "variants" polynucleotides are meant that differ from the identified nucleic acid sequence but still encode a polypeptide that has the same PRRSV receptor activity as the identified polypeptide.

Variants may be natural or non-natural variants. Non-naturally occurring variant may be introduced by mutagenesis. Natural variants may be allelic variants. An allelic variant is one of several alternate forms of a gene occupying a locus on a chromosome of an organism.

Sometimes, a gene is expressed in a certain tissue as a splicing variant, resulting in an altered 5' or 3' mRNA or the inclusion or exclusion of one or more exon sequences. These sequences as well as the proteins encoded by these sequences all are expected to perform the same or similar functions and form also part of the invention.

An isolated cDNA sequence may be incomplete due to incomplete transcription from the corresponding mRNA, or clones may be obtained containing fragments of the complete cDNA. Various techniques are known in the art to complete said cDNA sequences, such as RACE (Rapid Amplification of cDNA ends).

Polynucleotides that have a nucleic acid sequence that is a variants of the identified nucleic add sequence may be isolated by a method comprising the steps of: a) hybridizing a DNA comprising all or part of the identified sequence as reflected in SEQ ID NO: 1, under stringent conditions against nucleic acids being (genomic) DNA or cDNA isolated from porcine cells (preferably PAMs) which highly express the polynucleotide of interest; and b) isolating said nucleic acids by methods known to a skilled person in the art.

The hybridization conditions are preferably highly stringent.

According to the present invention the term "stringent" means washing conditions of 1×SSC, 0.1% SDS at a temperature of 65° C.; highly stringent conditions refer to a reduction in SSC towards 0.3×SSC, more preferably to 0.1×SSC. Preferably the first two washings are subsequently carried out twice each during 15-30 minutes. If there is a need to wash under highly stringent conditions an additional wash with 0.1×SSC is performed once during 15 minutes. Hybridization can be performed e.g. overnight in 0.5M phosphate buffer pH 7.5/7% SDS at 65° C. Such hybridization methods are disclosed in any standard textbook on molecular cloning, for example: Molecular Cloning: a laboratory manual, 3rd ed.; eds: Sambrook et al., CSHL press, 2001.

As an alternative the isolation method might comprise nucleic acid amplification methodology using primers and/or probes derived from the nucleic acid sequence provided with the present invention. Such primers and/or probes are oligonucleotides that are at least 15 nucleotides in length, preferred oligo's have about 25-50 nucleotides.

To test whether polynucleotides, the nucleic acid sequence of which represents a variant of the identified nucleic acid sequence, encode polypeptides that are functionally related to the identified sequence, methods as exemplified in the examples can be used. In example 6 it is disclosed how a sequence can be expressed in cells and how subsequently transfected cells can be tested for their susceptibility towards PRRSV infection.

Therefore, in a further aspect the present invention provides polynucleotides comprising a nucleic acid sequence encoding a polypeptide comprising an amino acid sequence having at least 90% identity with the amino acid sequence as depicted in SEQ ID NO: 2. Preferred are polynucleotides encoding polypeptides having at least 95% identity with SEQ ID NO: 2 and more preferred are those polynucleotides encoding polyproteins having at least 97% identity with SEQ ID NO: 2 wherein those encoding proteins having at least 98 or 99% are more preferred. Most preferred are polynucleotides encoding the polypeptide of SEQ ID NO: 2. Due to the degeneracy of the genetic code, polynucleotides encoding an identical or substantially identical amino add sequence may utilise different specific codons. All polynucleotides encoding the polypeptides as defined above are considered to be part of the invention.

In particular preferred polynucleotides according to the invention are isolated polynucleotides having at least 90% identity with the entire nucleic acid sequence of SEQ ID NO: 1. More preferred are those polynucleotides having at least 95% identity, and yet more preferred at least 97, preferably 98% or 99% identity to the entire sequence of SEQ ID NO: 1.

Such polynucleotides include polynucleotides comprising the nucleic acid sequence depicted in SEQ ID NO: 1. A polynucleotide encoding a polypeptide with a sequence as depicted in SEQ ID No.: 2 may comprise the nucleic acid sequence as depicted in SEQ ID No. 1. In a further preferred embodiment of the invention the polynucleotide consists of the nucleic acid sequence as depicted in SEQ ID No: 1.

The polynucleotides according to the invention may be DNA or RNA, preferably DNA. DNA according to the invention may be obtained from cDNA Alternatively, the coding sequence might be genomic DNA, or prepared using DNA synthesis techniques. If the polynucleotide is DNA, it may be in single stranded or double stranded form. The single strand might be the coding strand or the noncoding (anti-sense) strand.

Also included within the definition of polynucleotides are modified RNAs or DNAs.

Modifications in the bases of the nucleic acid may be made, and bases such as inosine may be incorporated. Other modification may involve, for example, modifications of the backbone.

With "isolated" is meant that the polynucleotide is isolated from the natural state, i.e. it has been changed or moved from its natural environment or both. The molecule is separate and discrete from the whole organism with which the molecule is found in nature.

"% Identity" defines the relation between two or more polynucleotides or polypeptides on the basis of a comparison between their aligned sequences.

Identity can be calculated by known methods. Identity percentages as mentioned herein are those that can be calculated with the GAP program, running under GCG (Genetics Computer Group Inc., Madison Wis.).

Parameters for polypeptide sequence comparison included the following:

Algorithm: Needleman and Wunch, J. Mol. Biol., 48, 443-453, 1970.

As a comparison matrix for amino acid alignments the BLO-
SUM62 matrix is used (Hentikoff and Hentikoff, P.N.A.S. USA, 89, 10915-10919, 1992) using the following parameters:
Gap penalty: 8
Gap length penalty: 2
No penalty for end gaps.
Parameters for nucleotide comparison used:
Algorithm: Needleman and Wunch (supra).
Comparison matrix: matches=+10, mismatch=0.
Gap penalty: 50.
Gap length penalty: 3.

The DNA according to the invention will be very useful for in vivo or in vitro expression of the encoded polypeptide in sufficient quantities and in substantially pure form. When the polynucleotides according to the invention are used for expression of the encoded polypeptide, the polynucleotides may include, in addition to the coding sequence for the polypeptide or functional fragment thereof, other coding sequences, for example, leader sequences or fusion portions, such as marker sequences and the like.

A wide variety of host cell and cloning vehicle combinations may be usefully employed in cloning the nucleic add sequence according to the invention. A polynucleotide according to the invention may be cloned into an appropriate expression system, such as a bacterial expression system (e.g. E. coli DH5α), a viral expression system (e.g. Baculovirus), a yeast system (e.g. S. Cerevisiae, Pichia) or eukaryotic cells (e.g. Cos, BHK, MDCK, MDBK, HeLa, PK15 cells). In all systems the polynucleotide is first cloned into an appropriate vector under control of a suitable constitutive or inducible promoter.

In another aspect the present invention therefore relates to a recombinant vector comprising a polynucleotide according to the invention. Suitable vectors are for example cosmids, bacterial or yeast plasmids, wide host range plasmids and vectors derived from combinations of plasmid and phage or virus DNA. Vectors derived from chromosomal DNA are also included. Furthermore an origin of replication and/or a dominant selection marker can be present in the vector according to the invention. The vectors according to the invention are suitable for transforming a host cell. Examples of suitable cloning vectors are plasmid vectors such as pBR322, the various pUC, pEMBL and Bluescript plasmids.

When used in the expression of the polypeptide or functional fragments thereof, a recombinant vector according to the present invention, may further comprise an expression control sequence operably linked to the nucleic acid sequence coding for the protein.

Operably linked refers to an arrangement wherein the control sequences are configured so as to perform their usual function, in effecting the expression of the polynucleotide.

Such expression control sequences generally comprise a promoter sequence and sequences, which regulate transcription and translation and/or enhance expression levels. Not all of these control sequences need to be present in a recombinant vector as long as the desired polynucleotide is capable of being transcribed and translated. Of course expression control and other sequences can vary depending on the host cell selected or can be made inducible.

Such expression control sequences are well known in the art and extend to any eukaryotic, prokaryotic, or viral promoter or poly-A signal capable of directing gene transcription.

Examples of useful promoters are the SV-40 promoter (Science 222, 524-527, 1983), the metallothionein promoter (Nature, 296, 39-42, 1982), the heat shock promoter (Voellmy et al., P.N.A.S. USA, 82, 4949-4953, 1985), the PRV gX promoter (Mettenleiter and Rauh, J. Virol. Methods, 30, 55-66, 1990), the human CMV IE promoter (U.S. Pat. No. 5,168,062), the Rous Sarcoma virus LTR promoter (Gorman et al., PNAS, 79, 6777-6781, 1982) or human elongation factor 1 alpha or ubiquitin promoter etc.

After the polynucleotide has been cloned into an appropriate vector, the construct may be transferred into the cell, bacteria, or yeast alone by means of an appropriate method, such as electroporation, CaCl2 transfection or lipofectins. When a baculovirus expression system is used, the transfer vector containing the polynucleotide may be transfected together with a complete baculo genome.

A recombinant virus, comprising a polynucleotide according to the invention, is likewise part of the present invention.

All these techniques are well known in the art and extensively described in protocols provided by manufactures of molecular biological materials (such as Promega, Stratagene, Clontech, and/or Invitrogen) and in literature or reference text books, for instance in Rodriguez, R. L. and D. T. Denhardt, edit., Vectors: A survey of molecular cloning vectors and their uses, Butterworths, 1988; Current protocols in Molecular Biology, eds.: F. M. Ausbel et al., Wiley N.Y., 1995; Molecular Cloning: a laboratory manual, 3rd ed.; eds: Sambrook et al., CSHL press, 2001 and DNA Cloning, Vol. 1-4, 2nd edition 1995, eds.: Glover and Hames, Oxford University Press).

The cells transformed with a polynucleotide or a vector according to the invention are likewise part of the present invention. Thus, in another aspect the present invention provides a cell capable of expressing a recombinant polypeptide, characterised in that the cell comprises a polynucleotide according to the invention encoding the expressed recombinant polypeptide. The term "recombinant" in this context refers to a polypeptide that is not expressed in the cell in nature. If the host cell is of porcine origin, the polynucleotide sequence may be present in the genomic material of the cell, but is not expressed in the particular type of porcine cell in a pig. Thus, a host cell which comprises the DNA or expression vector according to the invention is also within the scope of the invention. The engineered host cells can be cultured in conventional nutrient media which can be modified e.g. for appropriate selection, amplification or induction of transcription. The culture conditions such as temperature, pH, nutrients etc. are well known to those ordinary skilled in the art.

Cells that are transformed with a vector according to the invention may be of porcine or non-porcine origin. Cells that are of porcine origin may be PK 15 cells, SK cells or ST cells. Cells of nor-porcine origin that may be transformed to express a polypeptide according to the invention are, for example, MDCK cells, BHK cells, MDBK cells, insect cells, HeLa cells or COS cells.

A transformed cell according to the invention may comprise a polynucleotide according to the invention stably integrated into the genomic material or as part of an autonomously replicating vector.

A cell culture comprising a multitude of cells according to the Invention is likewise part of the present invention. In a preferred embodiment said cell culture is infected with a PRRSV. The PRRSV can be a wild-type virus or an attenuated virus. The latter is particularly suited for the preparation of vaccines. Cells according to the invention can be used to express the polypeptide and the polypeptide can be isolated from the cell culture.

In another aspect the present invention therefore provides for a method for producing a polypeptide that, when expressed on the surface of a cell, is capable of making the cell receptive for PRRSV, has an apparent molecular weight of approximately 210 kD and is reactive with MAB 41D3, comprising the steps of:

culturing a cell according to the invention, isolating polypeptide containing material from the cell culture.

Preferred cells according to the invention are cells that present the polypeptide on their surface. Since the polypeptide plays a role in the entrance of PRRSV in cells, cells that are able to express a polypeptide according to the invention on their surface, become accessible to the PRRSV virus. Thus, the present invention enables the infection with PRRSV of cells that are normally non-receptive for PRRSV. In this way, new routes to culturing PRRSV are provided.

The present invention thus provides for a method for producing PRRSV wherein a cell culture comprising cells according to the invention are infected with a PRRSV and cultured, after which the virus can be harvested from the cell culture. Whereas the virus, due to its limited cell tropism could be cultured in very specific cells only, with the present invention, new routes of culturing the virus become available. With the present invention it is now possible to grow PRRSV in cells that can be cultured in animal compound free media, a feature enhancing the quality of products based on the cultured virus, for example vaccine. Also cells that can grow in suspension can now be made susceptible for PRRSV, facilitating a more optimal production process in fermentors. Cells can be made more receptive for the virus and can be selected for higher PRRSV production titres. Once the virus has been grown to high titers, it can be processed according to the intended use by means known in the art. For example, viral fluids may be inactivated, for example with e.g. formalin, BPL, BEA or gamma-irradiation, for use in vaccines. In the alternative, the viral strain used in infection may be an attenuated strain for use in the production of live, attenuated, vaccines. Vaccines may be formulated by means known in the art. Usually this may involve the addition of an adjuvant and/or a suitable carrier.

Another advantage is related to the use of cells according to the invention in (diagnostic) testing. Cell lines that have been made more susceptible for the virus can be used in virus detection tests, whereas, with prior art methods, PAMs are needed. PAMs cells are primary non-growing cells that have to be harvested from pigs. The tedious process of harvesting PAMs is then avoided and a higher sensitivity can be obtained in such cell systems.

When porcine cells are used, these cells, may, like other cell types, be transformed with a vector comprising the genetic information for the polypeptide. However, porcine cells have, in their genomic material, already the genomic DNA sequence corresponding to the nucleic acid of the present invention. But the gene is not expressed in all porcine cells as it is in porcine alveolar macrophages. With the present invention the gene, in isolated form, and its sequence, have been elucidated. Now that this information, provided with the present invention, is available, other (other than transformation of the cell with a vector containing the gene) routes to expression of the gene in porcine cells have become available as well. Expression of the gene in porcine cells can also be achieved by "switching on" expression of the gene already present in porcine cells. With the present information the gene sequence Is provided and a promoter of choice can be inserted before the start codon by homologous recombination followed by the selection of cells expressing the receptor gene. This promoter can be a constitutive mammalian promoter (e.g. HCMV, SV40 LTR) or an inducible promoter (e.g. Tet-system).

Cells expressing the polypeptide on their surface may also be used in a screening assay used in screening compound libraries for compounds that specifically bind to the polypeptide. Since the polypeptide plays a role in entrance of PRRSV into cells, such compounds may be used in treating or preventing PRRSV infection.

Thus, in a further aspect, the present invention provides for a method for screening compounds, which affect this function of the polypeptide. These compounds may stimulate or inhibit the function of the polypeptide.

Compounds that may be identified with the screening method of the invention may be derived from a variety of sources including chemical compound libraries or mixtures of (natural) compounds.

The screening method may involve measuring the binding of a candidate compound to the polypeptide, or to cells or membranes bearing the polypeptide, or to a fusion protein bearing only the binding domain of the full-length polypeptide. Binding may be measured directly or indirectly. Binding may be measured directly, for example, by means of label associated with the compound. Binding may also be measured indirectly. For example, indirectly measuring the binding of a candidate compound may involve competition with a (labelled) competitor. The measuring of binding of a candidate compound may, for example, also be determined in a cell-based assay, wherein it can be determined whether a candidate compound is able to block the PRRSV virus from entering a cell. In that case it can be determined whether, in the presence of the compound, cells can still be infected with PRRSV.

In a further aspect, the present invention provides for methods of treating or preventing PRRSV infection in pigs by inhibiting binding of the PRRSV virus. This may be achieved by administering an inhibitor of the polypeptide, which will block the virus from entry into cells. Such an inhibitor may be a chemical compound, which may be (a derivative of) a compound identified with the screening method of the invention. Such an inhibitor can likewise be another molecule capable of binding to the polypeptide, e.g. an antibody or antibody fragment.

Another method of inhibiting the virus uptake is by covering the virus by soluble receptors. In that way the attachment and subsequent entry of the virus into the cells will be blocked: Thus the use of the polypeptide in the manufacture of a medicament for treatment or prevention of PRRSV infection in pigs is likewise part of the present invention.

The invention further relates to the use of a compound capable of affecting the PRRSV receptor function of a polypeptide in order to modulate the pig immune system. The use of the polypeptide, preferable in solubilized form, to modulate the pig immune system is likewise incorporated.

The composition used to administer the inhibitor should be formulated with a pharmaceutically acceptable carrier, adapted to the route of administration chosen.

FIGURES

FIG. 1. Expression of the p210 in recombinant PK-15 cells stably transfected with plasmid pcDNA3.1D/V5-His-TOPO containing the p210 cDNA (clone 80.2). An indirect immunofluorescence staining using MAb 41D3 (directed against the p210) and FITC labeled goat serum anti-mouse Ig was performed on methanol-fixed (A) or unfixed (B) cells. Porcine alveolar macrophages fixed with methanol were stained using the same protocol and included as a positive control (C).

Figure 2:
Figure 2:
Figure 2:

FIG. 2. Co-localization of PRRSV nucleocapsid and p210 in recombinant PK-15 cells expressing the p210 and infected with the Lelystad Virus. A double indirect immunofluorescence staining using MAb A27 (directed against the PRRSV nucleocapsid) and FITC labeled goat serum anti-mouse Ig followed by staining with biotinylated MAb 41D3 (directed against the p210) and Texas-Red labelled streptavidin was performed on methanol-fixed cells. Image (A) shows FITC signal, image (B) shows Texas Red signal and image (3), obtained by merging (A) and (B) gives a yellow signal when (A) and (B) co-localize.

FIG. 3: Identified genomic nucleic acid sequence (exons) of the p210 gene (SEQ ID NO:1), the complement thereto (SEQ ID NO:32), and the encoded amino acid sequence (SEQ ID NO:2).

FIG. 4: Identified cDNA nucleic acid sequence of a clone that expresses a functional p210 PRRSV receptor (SEQ ID NO:3), the complement thereto (SEQ ID NO:33), and the encoded amino acid sequence (SEQ ID NO:4).

EXAMPLES

Example 1

Identification of the PRRSV Receptor

1) Monoclonal Antibody Production:

To identify the receptor which may determine the macrophage tropism of PRRSV, a monoclonal antibody (41D3) was produced. This Mab completely blocked PRRSV infection of PAM (Duan et al., J. Virol, 72, 4520-4523, 1998; Duan et al., Adv. Exp. Med. Biol., 440, 81-88, 1998). Mab 41D3 reduced the attachment of PRRSV to PAM and immunoprecipitated a 210 kDa protein from PAM. This protein was detected on the dell membrane of PAM by flow cytometry and fluorescence microscopy. Fluorescence staining was absent on the membranes of PRRSV-nonpermissive cells including PBMC, porcine peritoneal macrophages, ST, SK, and PK15 cells. Cells from a PRRSV-permissive cell line, MARC-145 were also negatively stained with Mab 41D3.

Example 2

Purification of p210

Materials & Methods:

1) PAM Membrane Purification

PAM were obtained from 4- to 6-week-old conventional Belgian Landrace pigs from a PRRSV-negative herd according to the method previously described by Wensvoort et al. (Vet. Q., 13,121-130, 1991).

PAM were maintained in RPMI medium supplemented with 10% fetal bovine serum, 1% Penicillin/Streptomycin, and 1% Kanamycin. Twenty-four hours after planting at a density of 50×106 cells/175 cm2, fresh medium supplemented with 50 U/ml of recombinant porcine interferon α (rPo IFN-α1, Lefèvre et al., J. Gen. Virol., 71, 1057-1063, 1990) was added and PAM were maintained in this medium for an additional 48-72 hours. Non-adherent PAM were collected in medium by low speed centrifugation and adherent PAM were dislodged in PBS by manual agitation. Cells were pooled, washed three times with PBS and collected by centrifugation (7 min 700 g 4° C.). Cell pellet was resuspended in buffer A (10 mM Tris-HCl pH7.4, Complete™ protease inhibitor cocktail (Boehringer)) and lysed using a Douncer homogeneizer B1. Cell nuclei were pelleted by centrifugation (10 min 800 g 4° C.) and supernatant was further centrifuged (1 h 100,000 g 4° C.) to pellet the membrane fraction. This fraction was subsequently resuspended in 70% saccharose in buffer A and submitted to a 60%-30%-0% saccharose step gradient (1 h 100,000 g 4° C.). The 60-30% interface was collected, diluted 3 times in buffer A and pelleted by centrifugation (1 h 100,000 g 4° C.). The purified membrane fraction corresponding to 3×175 cm2 of PAM was resuspended in 1 ml buffer A and frozen at −70° C.

2) Purification of p210 by Immunoprecipitation and SDS-PAGE.

Protein-C sepharose (100 microliter, Pharmacia) was incubated for 1 h at 20° C. with 20 µl rabbit anti-mouse polyclonal serum (Dako), washed with PBS, and further incubated for 1 hr at 20° C. with 20 µl MAb 41D3. After washing with PBS, 400 µl of solubilized membrane fraction was added and incubated 16 h at 4° C. The solubilized membrane fraction was obtained by treating the purified membrane fraction of PAM with 0.1% Triton X-100 in 25 mM Tris-HCl pH7.4 for 1 h at 37° C. and centrifuging (30 min, 13000 g, 4° C.) to pellet non-solubilized products. Immunocomplexes were washed four times with PBS-0.1% Tween20 and once with water. To allow efficient recovery of p210 and allow its subsequent concentration to give a final volume compatible with SDS-PAGE, a modified Laemmli buffer (15.5 mM Tris-HCl pH6.8, 1% SDS, 1.25% 2-mercaptoethanol) was added to the immunocomplexes before boiling for 3 min. After centrifuging 1 min at 13000 g, the supernatant was concentrated 8 times using a vacuum centrifuge (Jouan RC 10.10), 10% glycerol was added, and proteins were separated by SDS PAGE using 7% acrylamide gel and reducing conditions. The 210 kDa band corresponded to p210. Three preparations of p210 purified from 8×175 cm2 of PAM (corresponding approximately to the quantity of PAM extracted from one pig) were pooled and analyzed by mass spectrometry.

Results:

It was observed that treatment of PAM for 72 h with porcine interferon resulted in an increased surface expression of p210 by a factor of 4 approximately as determined by FACS analysis using MAb 41D3. MAb 41D3 was found to be conformation-dependant because no recognition of p210 in Western blot occurred under reducing conditions. Many difficulties were encountered regarding recognition of the antigen by MAb 41D3 after detergent solubilisation, Consequently, the solubilisation and immunoprecipitation conditions allowing an efficient recovery of p210 were empirically determined. The type of detergent (ionic, non-ionic), its concentration, the incubation temperature, the solubilisation buffer were critical parameters affecting the recognition of p210 by MAb 41D3. Another critical problem was caused by the migration of the antibodies in the gel, under non-reducing conditions, just below p210, preventing an efficient separation. After labelling p210 (see below) and immunoprecipitation with MAb 41D3, we could determine the apparent molecular weight of the reduced glycoprotein and use reducing conditions to separate it from the reduced antibody molecules. Using the described conditions, we could purify 2-4 pmoles of p210 that were necessary to perform internal sequencing.

Example 3

Protein Sequence Analysis

Overnight in gel tryptic digestion was performed on the excised 210 kDa protein band in the presence of 2M urea, 0.1M Tris-HCl pH8.2. The resulting peptides were extracted and prepared to load them on a short reversed phase column (1 mm I.D.×100 mm-C18) in a 0.1% (v/v) TFA water/acetonitrile mobile phase system. The eluted peptides were collected automatically in 18 fractions of 50 µl. Aliquots of 0.5 µl of each fractions were taken and mixed with 0.5 µl matrix solution (a cyano-4-hydroxy cinnamic/2,5-dimethyl benzoic add ratio 1/4 by weight) and analyzed by reflectron mode. Peptides could be detected only in fractions 16 and 17. Maldi-T of mass spectrometry revealed in fraction 16 peptides with molecular monoisotopic masses of 956.1 Da, 1676.34 Da, 1853.51 Da, 1870.57 Da and in fraction 17, 1790.47 Da respectively, Fractions 7 to 14 and fractions 15, 17 and 18 were pooled. The pooled fractions and fraction 16 were lyophilised. Capillary Chromatography was performed on a PepMap C18 reversed phase column (0.3 mm I.D.×250 mm) in a 0.05% (v/v) formic acid water/acetonitrile mobile phase system at flow about 3 microliter/min. The eluted peptides were manually collected in fractions of 2 to 5 microliter. Aliquots of relevant peaks were loaded in gold coated needles and subjected to nanospray ESI-TOF-MS. The most intensive ions were selected for fragmentation.

Results:

The amino add sequence of 7 peptides was determined (Table 1). After searches of protein databases (BLAST 2.0.9., Altschul et al. Nucleic Acids Res., 25, 3389-3402, 1997) with the amino add sequence of these peptides, sequence Identities ranging form 75% to 91% to mouse sialoadhesin (Crocker et al., EMBO J., 13, 4490-4503, 1994) were found with peptides 1-5. No significant homology with any proteins were observed for peptides 6 and 7. Clearly the p210 is the porcine ortholog of mouse sialoadhesin.

TABLE 1

Sequence of the peptides derived from the p210 and comparison with mouse sialoadhesin.

| Peptide | Sequence of the p210 peptides | Sequence deduced from cDNA | Sequence of mouse sialoadhesin |
|---------|-------------------------------|----------------------------|--------------------------------|
| PEP1 | FSWYR (SEQ ID NO:5) | FSWYL (SEQ ID NO:12) | FSWYL (SEQ ID NO:19) |
| PEP2 | PPAQLQLIHR (SEQ ID NO:6) | PPAQLRLLHG (SEQ ID NO:13) | PPAQLQLFHR (SEQ ID NO:20) |
| PEP3 | ASSTMSVP (SEQ ID NO:7) | ASSTAASVP (SEQ ID NO:14) | ASSTEASVP (SEQ ID NO:21) |
| PEP4 | WLQEGSAASLSF (SEQ ID NO:8) | WLQEGSAASLSF (SEQ ID NO:15) | WLQEGPASSLQF (SEQ ID NO:22) |
| PEP5 | DAVLSSFWDSR (SEQ ID NO:9) | DAVLSSFWDSR (SEQ ID NO:16) | DAVLSSFRDSR (SEQ ID NO:23) |
| PEP6 | ALLLGQVEQR (SEQ ID NO:10) | ALLLGQVEQR (SEQ ID NO:17) | / |
| PEP7 | QATLTTIMDSGLGR (SEQ ID NO:11) | QATLTTLMDSGLGR (SEQ ID NO:18) | / |

Example 4

Biochemical Characterization of p210

Materials & Methods

To characterize p210, surface proteins of 7×106 PAM cells were labelled by biotinylation using the recommended protocol (protocol D 2, ECL protein biotinylation module, RPN2202, Amersham). The cell pellet was lysed in 100 µl of Tris 25 mM pH7.4, 0.1% Triton-X-100 and Complete™ protease inhibitor cocktail for 1 h at 37° C. After centrifugation (30 min, 13000 g, 4° C.), 30 µl of supernatant was added to 20 µl of protein G-sepharose preincubated with 2 µl Mab 41D3 and incubated for 2 h at 20° C. Immunocomplexes were washed four times with PBS-0.1% Tween20 and once with water. Treatments with endoglycosidases H and F, neuraminidase, O-glycosidase (Boehringer) and heparinase I (Sigma) were subsequently performed. EndoF treatments (16 h at 37° C.) were performed after denaturation using the endoF deglycosylation kit (Boehringer, cat. no 1836552) and 2.5-4 U endoF (Boehringer, cat. no 1 365 169) or without predenaturation, in PBS. EndoH treatment (16 h at 37° C.) was performed in NaAc 50 mM pH5.5, 0.02% SDS, 0.1M 2-mercaptoethanol and 10 mU endoH (Boehringer 1088726). Neuraminidase treatment (16 h at 37° C.) in 50 mM NaAc pH5.5, 4 mM CaCl2, 100 µg/ml BSA, 2 mU neuraminidase (Boehringer 1080725) was followed by 2 mU O-glycosidase (Boehringer 1347101) incubation in PBS for 16 h at 37° C. A combined endoglycosidases digestion was also performed using endoF (2.5 U), neuraminidase (2 mU) and O-glycosidase (2 mU) in PBS for 16 h at 37° C. Heparinase I (Sigma H2519) digestion was performed at 37° C. for 16 h in PBS using 5 U of the enzyme, like in Keil et al., 1996, J. Virol. 70, 3032-3038. Western blotting was carried out as recommended (Amersham) except the detection step that was performed using DAB (Sigma) reagent (Sambrook J. et al., Molecular Cloning: a laboratory manual, 2nd ed., Cold Spring Harbor Laboratory Press, Cold Spring Harbor, new York, 1989).

Results:

MAb 41D3 could not bind to p210 in a Western blot under reducing conditions. Therefore, we labelled p210 with biotin, and after immunoprecipitation with MAb 41D3, a Western blot experiment was performed using streptavidin conjugated to horse radish peroxidase. Different treatments were performed on the immunoprecipitated, biotin-labelled p210.

1) Migration Under Reducing and Non-Reducing Conditions:

In the presence of 2-mercaptoethanol, the biotinylated p210 migrated as a single band of 220 kDa. In non-reducing conditions, a major diffuse band migrating as a 180 kDa protein was observed together with a minor band of much higher apparent molecular weight As no other proteins could be detected, we suggested that p210 occurred as a multimer (minor band, probably a dimer) and monomer (major band) that were linked by intermolecular disulphide bridges, resulting in a single band after reduction. In addition, our data also suggest the presence of intramolecular disulphide bridges because the reduced protein migrated much slower than the non-educed monomer.

2) Treatment with Endoglycosidase H, F and Heparinase I

To analyze the glycosylation of p210, we treated the immunoprecipitated protein with endoglycosidases H (endoH) or F (endoF). The lack of sensitivity to endoH suggested that p210 did not contain hybrid or high mannose glycans and that the n-glycans present on p210 were of the complex type. An important shift of approximately 30 kDa was observed in the presence of endoF, yielding a protein of 180 kDa in reducing conditions. In non-reducing conditions, we observed a shift in molecular weight of both the dimer and the monomer, resulting in the appearance of two bands of higher mobilities. These results indicated that p210 was highly modified with N-linked glycans and provided additional indication that the dimer was a complex of p210.

Because it was shown that the binding of PRRSV to MARC cells was inhibited when these cells were treated with heparinase 1, we also assessed the heparinase I sensitivity of p210. No shift in SDS-PAGE were observed, indicating the absence of heparan-like moieties sensitive to heparinase I on p210.

3) Treatment with O-Glycosidase and Neuraminidase

Immunoprecipitated p210 was treated with Neuraminidase to detect the presence of sialic acid residues. No shift in SDS-PAGE was observed, indicating the lack of major amounts of sialic add residues on p210. Also, subsequent treatment with O-glycosidase did not result in a shift of apparent molecular weight, indicating the lack of O-glycans sensitive to cleavage by O-glycosidase on p210.

Example 5

Cloning and Sequencing of the p210 cDNA

DNA was prepared from pig whole blood as described in Innis et al. (in PCR protocols. A guide to methods and applications., Academic Press Inc., Harcourt Brace Jovanovich, Publishers, 1990) and served as initial target for PCR experiments using non-degenerate oligonucleotides based on the peptides 3 and 4. The degenerated nucleotide codes in the primers were chosen similar to the nucleotide sequence corresponding of the p210 peptides in mouse (accession number: EMBL Z36293) or in human (accession number: EMBL AL 109804). Two primers derived from mouse (forward 5' TCCTCAACTGCAGCCTCTGT 3' (SEQ ID NO:24) and reverse 5' AGTGAGGCAGCCGTTCCCTC 3' (SEQ ID NO:25)) amplified a 340 nt fragment corresponding to the end of exon 14, an intron, and exon 15 of the mouse sialoadhesin gene.

Specific porcine oligonucleotides were derived from this first sequence and used to screen a swine BAC library (Rogel-Gaillard et al., Cytogenet Cell genet., 85, 205-211, 1999) by PCR. One clone (BAC634C10) could be selected and was used for further sequence analysis of the pig p210 gene. Using standard techniques sequence information from exon 4 to 18 of the p210 gene was obtained.

To determine the sequence of exons 1-4 and exons 18-21, a 5' and 3' RACE was performed using total pig alveolar macrophage RNA according to the manufacturers instructions (GibcoBRL, RACE protocols for GC rich cDNA).

For the 5'RACE, the first strand cDNA was synthesized using a reverse primer derived from exon4 (5' TCTGGTCTTTGAGCTTCGTC 3' (SEQ ID NO:26)) and TdT tailed with dCTP. Second-strand synthesis was performed using supplied 5'-RACE Abridged Anchor primer and a nested primer derived from exon4 (5' ACCTGAGGGTTGCTGCTATT 3' (SEQ ID NO:27)). A semi-nested PCR was performed using supplied Abridged Universal Amplification Primer (AUAP) and a nested primer also derived from exon4 (5' CACCTGGCAGCTGAGGGTGACCAGATC 3' (SEQ ID NO:34)).

For the 3'RACE the supplied Adapter Primer for making the first strand cDNA was used and a forward primer derived from exon 18 (5' GACGCCCACCATGACTGTTTTTG 3' (SEQ ID NO:28)) together with supplied primer AUAP for the semi-nested PCR.

The full DNA sequence of the exons corresponding to the p210 coding sequence was assembled from the data of the PCR, RT-PCR, 5'RACE and 3'RACE (FIG. 3 and SEQ ID 1-2).

To isolate the total RNA and to obtain optimal amounts of the p210 encoding RNA, $5 \times 10^7$ macrophages were lysed directly in the culture vessel and the RNA extracted using the Rneasy kit (Quiagen). The first strand was made using SuperScript II RNase H- Reverse Transcriptase (GibcoBRL) and 2.5 µM random nonamers (Sigma) following the instructions of the manufacturer (GibcoBRL). For the PCR, 0.4 µM of forward primer 5' CACCATGGACTTCCTGCTCCTGCTCCTC 3' (SEQ ID NO:29) and 0.4 µM of reverse primer 5' CTTGGGGTTTGAAGCTAGGTCATAA 3' (SEQ ID NO:30) were mixed with 200 µM of each dNTP, 1U of ThermalAce DNA polymerase and ThermalAce reaction buffer (Invitrogen). Thermal cycling was performed as follows: 3 min at 95° C. then 30 cycles of {20 sec at 95° C., 30 sec at 65° C. and 5.3 min at 74° C.} and finally 10 min at 74 C°. Using these parameters the total 5.2kb p210 cDNA was amplified. The amplified DNA was purified from an agarose gel (GeneClean) and TOPO cloned in the eukaryotic expression vector (Invitrogen) according to the manufacturer's instructions. After transformation (*E. coli* TOP10 strain, Invitrogen), 9 colonies were selected for the presence of the cloned gene in the expected orientation. In this vector the coding sequence is expressed as a non-fusion protein from the CMV promoter. Finally the clone that rendered a functional p210 gene was sequenced and the cDNA sequence of the p210 gene determined (FIG. 4).

Example 6

Transfection of PK-15 Cells and Detection of Expression of the p210 PRRSV Receptor and Culturing of PRRSV PK-15 cells at 50% confluency were transfected with purified pcDNA3.1D/V5-His-TOPO plasmid containing the p210 cDNA using the Calcium Phosphate technique (Cell-Phect transfection kit, Pharmacia). Transfected cells were trypsinized 72 h post-transfection and cultivated in the presence of 1 mg/ml geneticin (GibcoBRL). Ten days post geneticin addition, colonies of geneticin resistant cells were isolated using sterile 3 mM filter papers soaked in trypsin. After culture of these colonies for 2 additional weeks in the presence of geneticin, the expression of the recombinant p210 was checked.

To check the expression of p210, cells were fixed with methanol for 10 min at 4 C, rehydrated in PBS, and incubated for 1 h at 37° C. with MAb p210 (ascites diluted 11300 in PBS supplemented with 10% decomplemented goat serum). After washing with PBS, cells were incubated for 1 h at 37° C. with a FITC labeled goat serum anti-mouse Ig (Molecular Probes) diluted 11100 in PBS supplemented with 10% decomplemented goat serum. After washing with PBS and water, cells were dried and observed under a fluorescent microscope.

Positive staining of groups of cells was detected in monolayers derived from the transfections made with 3 of the 9 selected plasmids.

To assess surface expression of the p210, the same staining protocol as described above was used except that cells were not fixed, PBS was replaced by culture medium (MEM without additives), 0.1% sodium azide was added to the antibodies and incubation steps were performed at 4° C. to block antibody endocytosis. From the 9 plasmids used, only 1 showed surface expression of the p210 in groups of cells.

To check whether the expression of p210 would make the cell permissive for PRRS the cells were infected in a minimum culture volume with different PRRSV strains at a multiplicity of infection of 0.1 TCID50/cell. After 1 h incubation, culture medium was added and cells incubated at 37° C. for a further 20 h. After washing with PBS, cells were fixed with methanol, washed with PBS and incubated for 1 h at 37 C with MAb A27 specific for PRRSV (hybridoma supernatant supplemented with 10% decomplemented goat serum). After washing with PBS, cells were Incubated for 1 h at 37° C. with a FITC labeled goat serum anti-mouse Ig (Molecular Probes) supplemented with 10% decomplemented goat serum. After washing with PBS and water, cells were dried and observed under a fluorescent microscope (FITC filter). Cells were then washed in PBS and incubated for 1 h at 37° C. with biotinylated Mab 41D3 in PBS. After washing with PBS, cells were incubated for 1 hour at 37° C. with Texas-Red labelled streptavidin (Molecular Probes) diluted in PBS. After washing with PBS and water, cells were dried and observed under a fluorescent microscope (Texas-Red filter).

Positive, infected cells were observed only in cells transfected with p210 where the p210 was displayed on the cell surface. Furthermore, all virus strains Incubated on this cell (LV strain, VR2332 and two Belgium wild type PRRSV strains) were able to infect the p210-expressing cell.

Example 7

Transfection of the Human Cell Line HEK293T Detection of Expression of the p210 PRRSV Receptor and Culturing of PRRSV HEK293T cells were transfected at 25% confluency with the Qiagen pcDNA3.1D/V5-His-TOPO (Invitrogen) plasmid containing the p210 cDNA using the Calcium Phosphate technique (Cellphect transfection kit, Amersham Pharmacia Biotech). Sixteen hours post-transfection, the cells were inoculated with the American type PRRSV VR-2332 (grown on Marc-145 cells), with the European type PRRSV Lelystad virus (grown on porcine alveoalar macrophages) and with the Belgian isolate 94V360 (grown on Marc-145 cells). Eight hours post infection, the cells were fixed with methanol for 10 minutes at 4° C., rehydrated in PBS, and both infected cells and cells expressing the p210 were identified using a double immunofluorescence staining. To detect PRRSV infection, the cells were incubated for 1 hour at 37° C. with Mab A27 (culture supernatant diluted 1/100 in PBS) which recognizes the PRRSV nucleocapsid protein. Cells were washed with PBS and incubated with FITC labeled goat-anti-mouse serum diluted 1/100 in PBS. HEK293T cells expressing the p210 protein were detected by incubating the cells for 1 hour at 37° C. with biotinylated Mab 41D3 (ascites diluted 1/200 in PBS), which is directed against the p210 protein. After washing with PBS, the cell; were further incubated for 1 hour at 37° C. with streptavidin Texas Red, diluted 1150 in PBS. Finally the cells were washed with PBS and mounted in a buffered glycerin solution containing 2.5% DABCO (Janssen Chimica). PRRSV infected cells (green) and cells expressing the p210 (red) were visualized by fluorescence microscopy. The transfected HEK293T cells could be infected both with the American type and the two European types of PRRSV.

The invention claimed is:

1. An isolated polynucleotide, comprising: a nucleic acid sequence encoding a porcine polypeptide, wherein said porcine polypeptide has greater than 99% sequence identity with SEQ ID NO:2, has a molecular weight of approximately 210 KD, and is reactive with MAB 41D3, and wherein said porcine polypeptide when expressed on the surface of a cell makes the cell receptive for PRRSV.

2. A recombinant vector, comprising: the polynucleotide according to claim 1.

3. The recombinant vector according to claim 2, wherein the polynucleotide is operably linked to an expression control sequence.

4. A recombinant virus, comprising: the polynucleotide according to claim 1.

5. A method for producing a polypeptide encoded by the polynucleotide according to claim 1, comprising the steps of:
   culturing cells infected with a recombinant vector comprising the polynucleotide according to claim 1, and
   isolating polypeptide containing material from the cell culture.

6. A method for producing a polypeptide encoded by the polynucleotide according to claim 1, comprising the steps of:
   culturing cells infected with a recombinant virus comprising the polynucleotide according to claim 1, and
   isolating polypeptide containing material from the cell culture.

7. A method of producing transformed cells comprising
   a) transfecting cells with a recombinant vector or a recombinant virus comprising the polynucleotide according to claim 1; and
   b) culturing the transfected cells thereby producing transformed cells.

8. A method for producing PRRSV, comprising:
   a) transfecting cells with a recombinant virus comprising the polynucleotide according to claim 1 thereby making transformed cells;
   b) infecting the transformed cells with a PRRSV;
   c) culturing the infected transformed cells; and
   d) harvesting the virus from the cell culture.

9. A method for producing PRRSV, comprising:
   a) transfecting cells with a recombinant vector comprising the polynucleotide according to claim 1 thereby making transformed cells;
   b) infecting the transformed cells with a PRRSV;
   c) culturing the infected transformed cells; and
   d) harvesting the virus from the cell culture.

10. An isolated non-porcine cell comprising the polynucleotide according to claim 1.

11. A cell culture comprising a multitude of cells according to claim 10.

12. The cell culture according to claim 11, infected with a PRRS virus.

* * * * *

SEQUENCE LISTING

```
<160> NUMBER OF SEQ ID NOS: 34

<210> SEQ ID NO 1
<211> LENGTH: 5193
<212> TYPE: DNA
<213> ORGANISM: porcine

<400> SEQUENCE: 1
atggacttcc tgctcctgct cctcctcctg gcttcatctg ctctagcagg cctggcctcg      60
tggacggttt ccagccccga gaccgtgcag ggcatcaagg gctcctgcct catcatcccc     120
tgcaccttcg gcttcccggc caacgtggag gtgccccatg gcatcacagc catctggtac     180
tatgactact caggcaagcg cctggtagtg agccactcca ggaacccaaa ggtggtggag     240
aaccacttcc aaggccgggc cctgctgttg ggcaggttga acagaggac gtgcagcctg     300 ctgctgaagg acctgcagcc ccaggactcg ggctcctata acttccgctt tgagatcagc     360
gagggcaacc gctggtcaga tgtcaaaggc acagttgtca ccgtgacaga ggtgcccagc     420
gtgcccacca ttgccttgcc agccaagctg catgagggca tggaggtgga cttcaactgc     480
tccactccct atgtgtgccc gacggagccg gtcaacctac agtggcaagg ccaggatccc     540
acccgctccg tcacctccca cctccagaag cttgagccct cgggcaccag ccacatggag     600
accctgcaca tggccctgtc ctggcaggac catggccgga tcctgagctg ccaggtctca     660
```

-continued

```
gcagccgaac gcaggatgca gaaggagatt cacctccaag tgcagtatgc ccccaagggt    720
gtggagatcc tttttcagcca ctccggacgg aacgtccttc caggtgatct ggtcaccctc    780
agctgccagg tgaatagcag caaccctcag gtcagttccg tgcagtgggt caaggatggg    840
acgaagctca aagaccagaa acgtgtactg cagttgcgcc gggcagcctg ggctgatgct    900
ggcgtctaca cctgccaagc cgggaatgcc gtgggctctt cagtctcacc cccggtcagc    960
ctccacgtct tcatggctga ggtccaggta agccctgtgg gctccatcct ggagaaccag   1020
acggtgacgc tggcctgcaa tacacctaag gaagcgccca gcgagctgcg ctacagctgg   1080
tacaagaacc acgccctgct ggagggctct cacagccgca ccctccggct gcactcagtt   1140
accagggcgg attcgggctt ctacttctgc gaggtgcaga acgcccgggg cagagagcgc   1200 tctcccctg tcagcgtggt ggtcagccac ccacccctca ccccggacct aactgccttc   1260
ctggagacac aggcggggct ggtgggcatc ctccaatgct ctgtggtcag cgagccccca   1320
gctactctgg tgttgtcaca cggggggcctc atcttggcct ctacctccgg ggagggtgac   1380
cacagcccac gcttcagtgt cgcctctgcc cccaactccc tgcgcctgga gattcaagac   1440
ctggggccaa cagacagtgg ggaatacatg tgctcagcca gcagttctct tgggaatgcg   1500
tcctccaccc tggacttcca tgccaatgca gcccgcctcc tcatcagccc agcagcagag   1560
gtggtggaag gcaggcggt gacactgagc tgcaggagca gcctgagcct gatgcctgac   1620
acccgttttt cctggtacct gaacggggcc ctgattctcg aggggcccag cagcagcctc   1680
ctgctcccag cagcctccag cacagatgcc ggctcatacc actgccgggc ccagaacagc   1740
cacagcacca gcgggccctc ctcacctgct gttctcaccg tgctctacgc cccacgccag   1800
cccgtgttca ctgcccagct ggaccctgat actgcaggag ctggggccgg acgccaaggc   1860
ctcctcttgt gccgtgtgga cagcgacccc ccagcccagc tgcagctgct ccacaggggc   1920
cgtgttgtgg cctcttctct gtcatggggg ggcggctgct gcacctgcgg aggctgtttc   1980
caccgcatga aggtcaccaa agcacccaac ctactgcgtg tagagatccg agacccggtg   2040
ctggaggatg agggtgtgta cctgtgcgag gccagcagcg ccctgggcaa cgcctccgcc   2100
tctgcaacct tggatgccca ggccactgtc ctggtcatca caccgtcaca cacgctgcag   2160
gaaggcattg aagccaacct gacttgcaac gtgagccgtg aagccagcgg ccctgccaac   2220
ttctcctggt tccgagatgg ggcgctatgg gcccagggcc ctctggacac cgtgacgctg   2280
ctacctgtgg ccagaactga tgctgccctc tatgcttgcc gcatcgtcac cgaggctggt   2340
gctggcctct ccaccctgt ggccctgaat gtgctctatc cccccgatcc tccaaagttg   2400
tcagccctcc tggacgtgga ccagggccac acggctgtgt tcgtctgtac tgtggacagt   2460
cgccctcttg cccagttggc cctgttccgt ggggaacacc tcctgccgc cagctcggca   2520 ctccggctcc ccctcgtgg ccgcctccag gccaaagcct cggccaactc cttgcagcta   2580
gaggtccgag acttgagcct tggggactct ggcagctacc actgtgaggc caccaacatc   2640
cttggatcag ccaacactc tcttaccttc caggtccgag agcctgggt ccgggtgtca   2700 ccgtcgcctg agtccagga gggccaggct gtggtcctga ctgccaggt acccataggg   2760 gtcctggagg ggacctcata tcgttggtat cgggatggcc agcccctcca ggagtccact   2820
tcggccacgc tccgttttgc agccataact ctgagccagg ctggagccta ccattgccaa   2880
gcccaagctc caggctcagc caccacggac ctggctgccc ctgtcagcct ccacgtgacc   2940
tacgcacctc gccaggccac actcaccacc ctgatggact caggcctcgg gcgactgggc   3000
ctccttctgt gccgtgtgaa cagtgaccct cctgcccagc tccgactgct ccatgggagc   3060
```

-continued

```
cgcctcgtgg cctctactct acaaggtgtg gaggagcttg caggcagctc tccccgccta    3120
caggtggcca cagcccccaa cacgctgcgc ctggagatcc acaacgcagt gctggaggat    3180
gaaggcgtct acacctgcga ggccaccaac accctgggtc agaccttggc ctccgccgcc    3240
ttcgatgccc aggctatgag agtgcaggtg tggcccaatg ccaccgtgca agaggggcag    3300
ctggtgaacc tgacctgcct tgtatggacc acgcacctgg cccagctcac ctacacgtgg    3360
taccgagacc agcagcagct cccaggtgct gcccactcca tcctcctgcc caatgtcact    3420
gtcacagatg ccgcctccta ccgctgtggc atattgatcc ctggccaggc actccgcctc    3480
tccagacctg tcgccctgga tgtcctctac gcaccccgca gactgcgcct gacccatctc    3540
ttggagagcc gtggtgggca gctggccgtg gtgctgtgca ctgtggacag tcgcccagct    3600
gcccagctga ccctcagcca tgctggccgc ctcctggcct cctcaaccgc agcctctgtc    3660
cccaacaccc tgcgcctgga gctgtgggag ccccggccca gtgatgaggg tctctacagc    3720
tgctcggccc gcagtcctct gggccaggcc aacacatccc tggagctgcg gctagagggc    3780
gtgcaggtgg cactggctcc atcggccact gtgccggagg gggcccctgt cacagtgacc    3840
tgtgaagacc tgctgccccg cccacccact ctctatgtct ggtaccacaa cagccgttgg    3900
ctgcaggagg ggtcggctgc ctccctctcg tttccagcgg ctacacgggc tcacgcgggc    3960
gcctatacct gccaggtcca ggatgcccag ggcacacgca tctcccagcc cgcagcactg    4020
cacatcctct atgcccctcg ggatgctgtc ctttcctcct tctgggactc aagggccagc    4080
cctatggccg tggtacagtg cactgtggac agcgagccac ctgccgagat gaccctgtcc    4140
catgatggca aggtgctggc caccagccat ggggtccacg gcttagcagt ggggacaggc    4200
catgtccagg tggcccgcaa cgccctgcag ctgcgggtgc agaatgtgcc ctcacgtgac    4260
aaggacacct acgtctgcat ggaccgcaac tccttgggct cagtcagcac catggggcag    4320
ctgcagccag aaggtgtgca cgtggtagct gagccagggc tggatgtgcc tgaaggcaca    4380
gcgctgaacc tgagctgtcg cctccctagt ggccctgggc acataggcaa ctccaccttt    4440
gcttggttcc ggaacggtcg gcagctacac acagagtctg tgcccaccct taccttcacc    4500
catgtggccc gcgcccaagc tggcttgtac cactgccagg ctgagctccc cgccggggct    4560
gccacctctg ctccagtctt gctccgggtg ctctacccct ccaagacgcc caccatgact    4620
gttttttgtg gagcccgaggg tggcatccag ggcattctgg actgccgagt ggacagtgag    4680
cccctagcca gcctgaccct ccacctgggc agtcggctgg tggcctccag ccagcctcag    4740
gctgcccctg ccaagccgca catccgcgtc tcagccagtc ccaatgcctt gcgagtggac    4800
atggaggagc tgaagcccag tgaccagggg agtatgtgt gctcggcctc caatgccctg    4860
ggctctgcct ctgctgccac ctacttcgga accagagccc tgcatcgcct gcatctgttc    4920
cagcaccttc tctggttcct ggggctgctg gcgagcctcc tcttcctact gttgggcctg    4980
ggggtctggt acgcctggag acggggaaat ttttacaagc tgagaatggg cgaatattca    5040
gtagagatgg tatctcggaa ggaaaccacg cagatgtcca ctgaccagga agaagttact    5100
ggaatcggtg atgatgcggg ctctgtgaac caggcggcat ttgatcctgc ccacctctgt    5160
gaaaacacac agtctgtgaa aagcacagtc tga                                 5193
```

<210> SEQ ID NO 2
<211> LENGTH: 1730
<212> TYPE: PRT
<213> ORGANISM: porcine

<400> SEQUENCE: 2

```
Met Asp Phe Leu Leu Leu Leu Leu Ala Ser Ser Ala Leu Ala
1               5                   10                  15

Gly Leu Ala Ser Trp Thr Val Ser Ser Pro Glu Thr Val Gln Gly Ile
            20                  25                  30

Lys Gly Ser Cys Leu Ile Ile Pro Cys Thr Phe Gly Phe Pro Ala Asn
            35                  40                  45

Val Glu Val Pro His Gly Ile Thr Ala Ile Trp Tyr Tyr Asp Tyr Ser
    50                  55                  60

Gly Lys Arg Leu Val Val Ser His Ser Arg Asn Pro Lys Val Val Glu
65                  70                  75                  80

Asn His Phe Gln Gly Arg Ala Leu Leu Gly Gln Val Glu Gln Arg
                85                  90                  95

Thr Cys Ser Leu Leu Leu Lys Asp Leu Gln Pro Gln Asp Ser Gly Ser
                100                 105                 110

Tyr Asn Phe Arg Phe Glu Ile Ser Glu Gly Asn Arg Trp Ser Asp Val
                115                 120                 125

Lys Gly Thr Val Val Thr Val Thr Glu Val Pro Ser Val Pro Thr Ile
    130                 135                 140

Ala Leu Pro Ala Lys Leu His Glu Gly Met Glu Val Asp Phe Asn Cys
145                 150                 155                 160

Ser Thr Pro Tyr Val Cys Pro Thr Glu Pro Val Asn Leu Gln Trp Gln
                165                 170                 175

Gly Gln Asp Pro Thr Arg Ser Val Thr Ser His Leu Gln Lys Leu Glu
                180                 185                 190

Pro Ser Gly Thr Ser His Met Glu Thr Leu His Met Ala Leu Ser Trp
            195                 200                 205

Gln Asp His Gly Arg Ile Leu Ser Cys Gln Val Ser Ala Ala Glu Arg
        210                 215                 220

Arg Met Gln Lys Glu Ile His Leu Gln Val Gln Tyr Ala Pro Lys Gly
225                 230                 235                 240

Val Glu Ile Leu Phe Ser His Ser Gly Arg Asn Val Leu Pro Gly Asp
                245                 250                 255

Leu Val Thr Leu Ser Cys Gln Val Asn Ser Ser Asn Pro Gln Val Ser
                260                 265                 270

Ser Val Gln Trp Val Lys Asp Gly Thr Lys Leu Lys Asp Gln Lys Arg
            275                 280                 285

Val Leu Gln Leu Arg Arg Ala Ala Trp Ala Asp Ala Gly Val Tyr Thr
    290                 295                 300

Cys Gln Ala Gly Asn Ala Val Gly Ser Ser Val Ser Pro Pro Val Ser
305                 310                 315                 320

Leu His Val Phe Met Ala Glu Val Gln Val Ser Pro Val Gly Ser Ile
                325                 330                 335

Leu Glu Asn Gln Thr Val Thr Leu Ala Cys Asn Thr Pro Lys Glu Ala
                340                 345                 350

Pro Ser Glu Leu Arg Tyr Ser Trp Tyr Lys Asn His Ala Leu Leu Glu
            355                 360                 365

Gly Ser His Ser Arg Thr Leu Arg Leu His Ser Val Thr Arg Ala Asp
        370                 375                 380

Ser Gly Phe Tyr Phe Cys Glu Val Gln Asn Ala Arg Gly Arg Glu Arg
385                 390                 395                 400

Ser Pro Pro Val Ser Val Val Ser His Pro Leu Thr Pro Asp
                405                 410                 415
```

```
Leu Thr Ala Phe Leu Glu Thr Gln Ala Gly Leu Val Gly Ile Leu Gln
            420                 425                 430

Cys Ser Val Val Ser Glu Pro Pro Ala Thr Leu Val Leu Ser His Gly
            435                 440                 445

Gly Leu Ile Leu Ala Ser Thr Ser Gly Glu Gly Asp His Ser Pro Arg
            450                 455                 460

Phe Ser Val Ala Ser Ala Pro Asn Ser Leu Arg Leu Glu Ile Gln Asp
465                 470                 475                 480

Leu Gly Pro Thr Asp Ser Gly Glu Tyr Met Cys Ser Ala Ser Ser Ser
            485                 490                 495

Leu Gly Asn Ala Ser Ser Thr Leu Asp Phe His Ala Asn Ala Ala Arg
            500                 505                 510

Leu Leu Ile Ser Pro Ala Ala Glu Val Val Glu Gly Gln Ala Val Thr
            515                 520                 525

Leu Ser Cys Arg Ser Ser Leu Ser Leu Met Pro Asp Thr Arg Phe Ser
            530                 535                 540

Trp Tyr Leu Asn Gly Ala Leu Ile Leu Glu Gly Pro Ser Ser Ser Leu
545                 550                 555                 560

Leu Leu Pro Ala Ala Ser Ser Thr Asp Ala Gly Ser Tyr His Cys Arg
            565                 570                 575

Ala Gln Asn Ser His Ser Thr Ser Gly Pro Ser Ser Pro Ala Val Leu
            580                 585                 590

Thr Val Leu Tyr Ala Pro Arg Gln Pro Val Phe Thr Ala Gln Leu Asp
            595                 600                 605

Pro Asp Thr Ala Gly Ala Gly Ala Gly Arg Gln Gly Leu Leu Leu Cys
            610                 615                 620

Arg Val Asp Ser Asp Pro Pro Ala Gln Leu Gln Leu Leu His Arg Gly
625                 630                 635                 640

Arg Val Val Ala Ser Ser Leu Ser Trp Gly Gly Gly Cys Cys Thr Cys
            645                 650                 655

Gly Gly Cys Phe His Arg Met Lys Val Thr Lys Ala Pro Asn Leu Leu
            660                 665                 670

Arg Val Glu Ile Arg Asp Pro Val Leu Glu Asp Glu Gly Val Tyr Leu
            675                 680                 685

Cys Glu Ala Ser Ser Ala Leu Gly Asn Ala Ser Ala Ser Ala Thr Leu
            690                 695                 700

Asp Ala Gln Ala Thr Val Leu Val Ile Thr Pro Ser His Thr Leu Gln
705                 710                 715                 720

Glu Gly Ile Glu Ala Asn Leu Thr Cys Asn Val Ser Arg Glu Ala Ser
            725                 730                 735

Gly Pro Ala Asn Phe Ser Trp Phe Arg Asp Gly Ala Leu Trp Ala Gln
            740                 745                 750

Gly Pro Leu Asp Thr Val Thr Leu Leu Pro Val Ala Arg Thr Asp Ala
            755                 760                 765

Ala Leu Tyr Ala Cys Arg Ile Val Thr Glu Ala Gly Ala Gly Leu Ser
            770                 775                 780

Thr Pro Val Ala Leu Asn Val Leu Tyr Pro Pro Asp Pro Pro Lys Leu
785                 790                 795                 800

Ser Ala Leu Leu Asp Val Asp Gln Gly His Thr Ala Val Phe Val Cys
            805                 810                 815

Thr Val Asp Ser Arg Pro Leu Ala Gln Leu Ala Leu Phe Arg Gly Glu
            820                 825                 830
```

```
His Leu Leu Ala Ala Ser Ser Ala Leu Arg Leu Pro Pro Arg Gly Arg
    835                 840                 845

Leu Gln Ala Lys Ala Ser Ala Asn Ser Leu Gln Leu Glu Val Arg Asp
    850                 855                 860

Leu Ser Leu Gly Asp Ser Gly Ser Tyr His Cys Glu Ala Thr Asn Ile
865                 870                 875                 880

Leu Gly Ser Ala Asn Thr Ser Leu Thr Phe Gln Val Arg Gly Ala Trp
                885                 890                 895

Val Arg Val Ser Pro Ser Pro Glu Leu Gln Glu Gly Gln Ala Val Val
            900                 905                 910

Leu Ser Cys Gln Val Pro Ile Gly Val Leu Glu Gly Thr Ser Tyr Arg
    915                 920                 925

Trp Tyr Arg Asp Gly Gln Pro Leu Gln Glu Ser Thr Ser Ala Thr Leu
    930                 935                 940

Arg Phe Ala Ala Ile Thr Leu Ser Gln Ala Gly Ala Tyr His Cys Gln
945                 950                 955                 960

Ala Gln Ala Pro Gly Ser Ala Thr Thr Asp Leu Ala Ala Pro Val Ser
                965                 970                 975

Leu His Val Thr Tyr Ala Pro Arg Gln Ala Thr Leu Thr Leu Met
            980                 985                 990

Asp Ser Gly Leu Gly Arg Leu Gly  Leu Leu Leu Cys Arg  Val Asn Ser
            995                 1000                 1005

Asp Pro  Pro Ala Gln Leu Arg  Leu Leu His Gly Ser  Arg Leu Val
    1010                 1015                 1020

Ala Ser  Thr Leu Gln Gly Val  Glu Glu Leu Ala Gly  Ser Ser Pro
    1025                 1030                 1035

Arg Leu  Gln Val Ala Thr Ala  Pro Asn Thr Leu Arg  Leu Glu Ile
    1040                 1045                 1050

His Asn  Ala Val Leu Glu Asp  Glu Gly Val Tyr Thr  Cys Glu Ala
    1055                 1060                 1065

Thr Asn  Thr Leu Gly Gln Thr  Leu Ala Ser Ala Ala  Phe Asp Ala
    1070                 1075                 1080

Gln Ala  Met Arg Val Gln Val  Trp Pro Asn Ala Thr  Val Gln Glu
    1085                 1090                 1095

Gly Gln  Leu Val Asn Leu Thr  Cys Leu Val Trp Thr  Thr His Leu
    1100                 1105                 1110

Ala Gln  Leu Thr Tyr Thr Trp  Tyr Arg Asp Gln Gln  Gln Leu Pro
    1115                 1120                 1125

Gly Ala  Ala His Ser Ile Leu  Leu Pro Asn Val Thr  Val Thr Asp
    1130                 1135                 1140

Ala Ala  Ser Tyr Arg Cys Gly  Ile Leu Ile Pro Gly  Gln Ala Leu
    1145                 1150                 1155

Arg Leu  Ser Arg Pro Val Ala  Leu Asp Val Leu Tyr  Ala Pro Arg
    1160                 1165                 1170

Arg Leu  Arg Leu Thr His Leu  Leu Glu Ser Arg Gly  Gly Gln Leu
    1175                 1180                 1185

Ala Val  Val Leu Cys Thr Val  Asp Ser Arg Pro Ala  Ala Gln Leu
    1190                 1195                 1200

Thr Leu  Ser His Ala Gly Arg  Leu Leu Ala Ser Ser  Thr Ala Ala
    1205                 1210                 1215

Ser Val  Pro Asn Thr Leu Arg  Leu Glu Leu Trp Glu  Pro Arg Pro
    1220                 1225                 1230

Ser Asp  Glu Gly Leu Tyr Ser  Cys Ser Ala Arg Ser  Pro Leu Gly
```

|                                    | 1235 |     |     |     | 1240 |     |     |     | 1245 |     |
|---|---|---|---|---|---|---|---|---|---|---|

```
Gln Ala Asn Thr Ser Leu Glu Leu Arg Leu Glu Gly Val Gln Val
    1250                1255                1260
Ala Leu Ala Pro Ser Ala Thr Val Pro Glu Gly Ala Pro Val Thr
    1265                1270                1275
Val Thr Cys Glu Asp Pro Ala Ala Arg Pro Pro Thr Leu Tyr Val
    1280                1285                1290
Trp Tyr His Asn Ser Arg Trp Leu Gln Glu Gly Ser Ala Ala Ser
    1295                1300                1305
Leu Ser Phe Pro Ala Ala Thr Arg Ala His Ala Gly Ala Tyr Thr
    1310                1315                1320
Cys Gln Val Gln Asp Ala Gln Gly Thr Arg Ile Ser Gln Pro Ala
    1325                1330                1335
Ala Leu His Ile Leu Tyr Ala Pro Arg Asp Ala Val Leu Ser Ser
    1340                1345                1350
Phe Trp Asp Ser Arg Ala Ser Pro Met Ala Val Val Gln Cys Thr
    1355                1360                1365
Val Asp Ser Glu Pro Pro Ala Glu Met Thr Leu Ser His Asp Gly
    1370                1375                1380
Lys Val Leu Ala Thr Ser His Gly Val His Gly Leu Ala Val Gly
    1385                1390                1395
Thr Gly His Val Gln Val Ala Arg Asn Ala Leu Gln Leu Arg Val
    1400                1405                1410
Gln Asn Val Pro Ser Arg Asp Lys Asp Thr Tyr Val Cys Met Asp
    1415                1420                1425
Arg Asn Ser Leu Gly Ser Val Ser Thr Met Gly Gln Leu Gln Pro
    1430                1435                1440
Glu Gly Val His Val Val Ala Glu Pro Gly Leu Asp Val Pro Glu
    1445                1450                1455
Gly Thr Ala Leu Asn Leu Ser Cys Arg Leu Pro Ser Gly Pro Gly
    1460                1465                1470
His Ile Gly Asn Ser Thr Phe Ala Trp Phe Arg Asn Gly Arg Gln
    1475                1480                1485
Leu His Thr Glu Ser Val Pro Thr Leu Thr Phe Thr His Val Ala
    1490                1495                1500
Arg Ala Gln Ala Gly Leu Tyr His Cys Gln Ala Glu Leu Pro Ala
    1505                1510                1515
Gly Ala Ala Thr Ser Ala Pro Val Leu Leu Arg Val Leu Tyr Pro
    1520                1525                1530
Pro Lys Thr Pro Thr Met Thr Val Phe Val Glu Pro Glu Gly Gly
    1535                1540                1545
Ile Gln Gly Ile Leu Asp Cys Arg Val Asp Ser Glu Pro Leu Ala
    1550                1555                1560
Ser Leu Thr Leu His Leu Gly Ser Arg Leu Val Ala Ser Ser Gln
    1565                1570                1575
Pro Gln Ala Ala Pro Ala Lys Pro His Ile Arg Val Ser Ala Ser
    1580                1585                1590
Pro Asn Ala Leu Arg Val Asp Met Glu Glu Leu Lys Pro Ser Asp
    1595                1600                1605
Gln Gly Glu Tyr Val Cys Ser Ala Ser Asn Ala Leu Gly Ser Ala
    1610                1615                1620
Ser Ala Ala Thr Tyr Phe Gly Thr Arg Ala Leu His Arg Leu His
    1625                1630                1635
```

-continued

| | | | | | | | | | | |
|---|---|---|---|---|---|---|---|---|---|---|
| Leu | Phe | Gln | His | Leu | Leu | Trp | Phe | Leu | Gly | Leu | Leu | Ala | Ser | Leu |
| | 1640 | | | | 1645 | | | | 1650 | |

| Leu | Phe | Leu | Leu | Leu | Gly | Leu | Gly | Val | Trp | Tyr | Ala | Trp | Arg | Arg |
| | 1655 | | | | 1660 | | | | 1665 | |

| Gly | Asn | Phe | Tyr | Lys | Leu | Arg | Met | Gly | Glu | Tyr | Ser | Val | Glu | Met |
| | 1670 | | | | 1675 | | | | 1680 | |

| Val | Ser | Arg | Lys | Glu | Thr | Thr | Gln | Met | Ser | Thr | Asp | Gln | Glu | Glu |
| | 1685 | | | | 1690 | | | | 1695 | |

| Val | Thr | Gly | Ile | Gly | Asp | Asp | Ala | Gly | Ser | Val | Asn | Gln | Ala | Ala |
| | 1700 | | | | 1705 | | | | 1710 | |

| Phe | Asp | Pro | Ala | His | Leu | Cys | Glu | Asn | Thr | Gln | Ser | Val | Lys | Ser |
| | 1715 | | | | 1720 | | | | 1725 | |

Thr Val
 1730

<210> SEQ ID NO 3
<211> LENGTH: 5193
<212> TYPE: DNA
<213> ORGANISM: porcine

<400> SEQUENCE: 3

```
atggacttcc tgctcctgct cctcctcctg gcttcatccg ctctagcagg cctggcctcg      60
tggacggttt ccaaccccga ccgtgcagg gcatcaagg gctcctgcct catcatcccc      120
tgcaccttcg gctcccggc caacgtggag gtgccccatg gcatcacagc catctggtac      180
tatgactact caggcaagcg cctggtagtg agccactcca ggaacccaaa ggtggtggag      240
aaccacttcc aagaccgggc cctgctgttg gggcaggttg agcagaggac gtgcagcctg      300
ctgctgaagg acctgcagcc ccaggactcg ggctcctata acttccgctt tgagatcagc      360
gagggcaacc gctggtcaga tgtcaaaggc acagttgtca ccgtgacaga ggtgcccagc      420
gtgcccacca ttgccttgcc agccaagctg catgagggca tggaggtgga cttcaactgc      480
tccactccct atgtgtgccc gacggagccg gtcaacctac agtggcaagg ccaggatccc      540
acccgctccg tcacctccca cctccagaag cttgagccct cgggcaccag ccacatggag      600
accctgcaca tggccctgtc ctggcaggac catggccgga tcctgagctg ccaggtctca      660
gcagccgaac gcaggatgca gaaggagatt cacctccaag tgcagtatgc ccccaagggt      720
gtggagatcc ttttcagcca ctccggacgg aacgtcctcc aggtgatctg gtcacccctc      780
agctgccagg tgaatagcag caaccctcag atcagttccg tgcagtgggt caaggatggg      840
acgaagctca agaccagaa acgtgtactg cagttgcgcc gggcagcctg gctgatgct      900
ggcgtctaca cctgccaagc cgggaatgcc gtgggctctt cagtctcacc cccggtcagc      960
ctccacgtct tcatggctga ggtccaggta agccctgtgg ctccatcct ggagaaccag      1020
acggtgacgc tggcctgcaa tacacctaag gaagcgccca cgagctgcg ctacagctgg      1080
tacaagaacc acgccctcct ggagggctct cacagccgca ccctccggct gcactcagtc      1140
accagggcgg attcgggctt ctacttctgc gaggtgcaga acgcccgggg cagagagcgc      1200
tctccccctg tcagcgtggg ggtcagccac ccacccctca cccggacct aactgccttc      1260
ctggagacac aggcggggct ggtgggcatc tccaatgct ctgtggtcag cgagccccca      1320
gctactctgg tgttgtcaca cggggggcctc atcttgacct ctaccctccga ggagggtgac      1380
cacagcccac gcttcagtgt cacctctgcc cccaactccc tgcgcctgga gattcaagac      1440
ctggggccaa cagacagtgg ggaatacatg tgctcagcca gcagttctct tgggaatgcg      1500
```

```
tcctccaccc tggacttcca tgccaatgca gcccgcctcc tcatcagccc agcagcagag    1560
gtggtggaag ggcaggcggt gacactgagc tgcaggagca gcctgagcct gatgcctgac    1620
acccgttttt cctggtacct gaacggggcc ctgattctcg aggggcccag cagcagcctc    1680
ctgctcccag cagcctccag cacagatgcc ggctcatacc actgccgggc ccagaacagc    1740
cacagcacca gcgggccctc ctcacctgct gttctcaccg tgctctacgc cccacgccag    1800
cccgtgttca ctgcccagct ggaccctgat actgcaggag ctggggccgg acgccaaggc    1860
ctcctcttgt gccgtgtgga cagcgacccc ccagcccagc tgcagctgct ccacaggggc    1920
cgtgttgtgg cctcttctct gtcatggggg ggcggctgct gcacctgcgg aggctgtttc    1980
caccgcatga aggtcaccaa agcacccaac ctactgcgtg tagagatccg agacccggtg    2040
ctggaggatg agggtgtgta cctgtgcgag gccagcagca ccctgggcaa cgcctccgcc    2100
tctgcaacct ggatgcccca ggccactgtc ctggtcatca caccgtcaca cacgctgcag    2160
gaaggcattg aagccaacct gatttgcaac gtgagccgtg aagccagcgg ccctgccaac    2220
ttctcctggt tccgagatgg ggcgctatgg gcccagggcc ctctggacac cgtgacactg    2280
ctacctgtgg ccagaactga tgctgccctc tatgcttgcc gcatcgtcac cgaggctggt    2340
gctggcctct ccacccctgt ggccctgaat gtgctctatc cccccgatcc tccaaagttg    2400
tcagccctcc tggacgtgga ccagggccac acggctgtgt cgtctgtac tgtggacagt    2460 cgccctcttg cccagttggc cctgttccgt ggggaacacc tcctggccgc cagctcggca    2520
ctccggctcc cccctcgtgg ccgcctccag gccaaagcct cggccaactc cttgcagcta    2580
gaggtccgag acttgagcct tggggactct ggcagctacc actgtgaggc caccaacatc    2640 cttgatcag ccaacacttc tcttaccttc caggtccgag gagcctgggt ccgggtgtca    2700
ccgtcgcctg agctccagga gggccaggct gtggtcctga gctgccaggt acccataggg    2760
gtcctggagg ggacctcata tcgttggtat cgggatggcc agccctcca ggagtccact    2820 tcggccacgc tccgttttgc agccataact ctgagccagg ctggagccta ccattgccaa    2880
gcccaagctc caggctcagc caccacggac ctggctgccc ctgtcagcct ccacgtgacc    2940
tacgcacctc gccaggccac actcaccacc ctgatggact caggcctcgg gcgactgggc    3000
ctccttctgt gccgtgtgaa cagtgaccct cctgcccagc tccgactgct ccatgggagc    3060
cgcctcgtgg cctctactct acaaggtgtg gaggagcttg caggcagctc tccccgccta    3120
caggtggcca cagcccccaa cacgctgcgc ctggagatcc acaacgcagt gctggaggat    3180
gaaggcgtct acacctgcga ggccaccaac acctgggtc agaccttggc ctccgccgcc    3240
ttcgatgccc aggctatgag agtgcaggtg tggcccaatg ccaccgtgca agaggggcag    3300
ctggtgaacc tgacctgcct tgtatggacc acgcacctgg cccagctcac ctacacatgg    3360
taccgagacc agcagcagct cccaggtgct gcccactcca tcctcctgcc caatgtcact    3420
gtcacagatg ccgcctccta ccgctgtggc atattgatcc ctggccaggc actccgcctc    3480
tccagacctg tcgccctgga tgtcctctac gcacccgca gactgcgcct gacccatctc    3540
ttggagagcc gtggtgggca gctggccgtg gtgctgtgca ctgtggacag tcgcccagct    3600
gcccagctga ccctcagcca tgctggccgc ctcctggcct cctcaaccgc agcctctgtc    3660
cccaacaccc tgcgcctgga gctgtgggag ccccggccca gtgatgaggg tctctacagc    3720
tgctcggccc gcagtcctct gggccaggcc aacacatccc tggagctgcg gctagagggc    3780
gtgcaggtga cactggctcc atcgaccact gtgccggagg gggcccctgt cacagtgacc    3840
```

```
tgtgaagacc ctgctgcccg cccacccacc ctctatgtct ggtaccacaa cagccgttgg    3900
ctgcaggagg ggtcggctgc ctccctctcg tttccagcgg ctacacgggc tcacgcgggc    3960
gcctatacct gccaggtcca ggatgcccag ggcacacgca tctcccagcc cgcagcactg    4020
cacatcctct atgcccctcg ggatgctgtc ctttcctcct tctgggactc aagggccagc    4080
cctatggccg tggtacagtg cactgtggac agcgagccac ctgccgagat gaccctgtcc    4140
cgtgatggca aggtgctggc caccagccat ggggcccacg gcttagcagt ggggacaggc    4200
catgtccagg tggcccgcaa cgccctgcag ctgcgggtgc agaatgtgcc ctcacgtgac    4260
aaggacacct acgtctgcat ggcccgcaac tccttgggct cagtcagcac catggggcag    4320
ctgcagccag aaggtgtgca cgtggtagcc gagccagggc tggatgtgcc cgaaggcaca    4380
gcgctgaacc tgagctgtcg cctccctagt ggccctgggc acatgggcaa ctccaccttt    4440
gcttggttcc ggaacggtcg gcagctacac acagagtctg tgcccaccct taccttcacc    4500
catgtggccc gcgcccaagc tggcttgtac cactgccagg ctgagctccc cgccggggct    4560
gccacctctg ctccagtctt gctccgggtg ctctaccctc caagacgcc caccatgact    4620 gttttttgtgg agcccgaggg tggcatccag ggcattctgg actgccgagt ggacagtgag    4680
cccctagcca gcctgaccct ccacctgggc agtcggctgg tggcctccag ccagccccag    4740 gctgccctg ccaagccgca catccgcgtc tcagccagtc ccaatgcctt gcgagtggac    4800
atggaggagc tgaagcccag tgaccagggg gagtatgtgt gctcggcctc caatgccctg    4860
ggctctgcct ctgctgccac ctacttcgga accagagccc tgcatcgcct gcatctgttc    4920
cggcaccttc tctggttcct ggggctgctg gcgagcctcc tcttcctact gttgggcctg    4980
ggggtctggt acgcctggag acggggaaat tttcacaagc tgagaatggg cgaatattca    5040
gtagagatgg tatctcggaa ggaaaccacg cagatgtcca ctgaccagga agaagttact    5100
ggaatcggtg atgatgcggg ctctgtgaac caggcggcat ttgatcctgc ccacctctgt    5160
gaaaacacac agtctgtgaa aagcacagtc tga                                 5193
```

<210> SEQ ID NO 4
<211> LENGTH: 1730
<212> TYPE: PRT
<213> ORGANISM: porcine

<400> SEQUENCE: 4

```
Met Asp Phe Leu Leu Leu Leu Leu Ala Ser Ser Ala Leu Ala
1               5                   10                  15

Gly Leu Ala Ser Trp Thr Val Ser Asn Pro Glu Thr Val Gln Gly Ile
                20                  25                  30

Lys Gly Ser Cys Leu Ile Ile Pro Cys Thr Phe Gly Phe Pro Ala Asn
            35                  40                  45

Val Glu Val Pro His Gly Ile Thr Ala Ile Trp Tyr Tyr Asp Tyr Ser
        50                  55                  60

Gly Lys Arg Leu Val Val Ser His Ser Arg Asn Pro Lys Val Val Glu
65                  70                  75                  80

Asn His Phe Gln Asp Arg Ala Leu Leu Leu Gly Gln Val Glu Gln Arg
                85                  90                  95

Thr Cys Ser Leu Leu Leu Lys Asp Leu Gln Pro Gln Asp Ser Gly Ser
            100                 105                 110

Tyr Asn Phe Arg Phe Glu Ile Ser Glu Gly Asn Arg Trp Ser Asp Val
        115                 120                 125

Lys Gly Thr Val Val Thr Val Thr Glu Val Pro Ser Val Pro Thr Ile
```

-continued

```
            130                 135                 140
Ala Leu Pro Ala Lys Leu His Glu Gly Met Glu Val Asp Phe Asn Cys
145                 150                 155                 160

Ser Thr Pro Tyr Val Cys Pro Thr Glu Pro Val Asn Leu Gln Trp Gln
                165                 170                 175

Gly Gln Asp Pro Thr Arg Ser Val Thr Ser His Leu Gln Lys Leu Glu
            180                 185                 190

Pro Ser Gly Thr Ser His Met Glu Thr Leu His Met Ala Leu Ser Trp
            195                 200                 205

Gln Asp His Gly Arg Ile Leu Ser Cys Gln Val Ser Ala Ala Glu Arg
210                 215                 220

Arg Met Gln Lys Glu Ile His Leu Gln Val Gln Tyr Ala Pro Lys Gly
225                 230                 235                 240

Val Glu Ile Leu Phe Ser His Ser Gly Arg Asn Val Leu Pro Gly Asp
                245                 250                 255

Leu Val Thr Leu Ser Cys Gln Val Asn Ser Ser Asn Pro Gln Ile Ser
            260                 265                 270

Ser Val Gln Trp Val Lys Asp Gly Thr Lys Leu Lys Asp Gln Lys Arg
            275                 280                 285

Val Leu Gln Leu Arg Arg Ala Ala Trp Ala Asp Ala Gly Val Tyr Thr
            290                 295                 300

Cys Gln Ala Gly Asn Ala Val Gly Ser Ser Val Ser Pro Pro Val Ser
305                 310                 315                 320

Leu His Val Phe Met Ala Glu Val Gln Val Ser Pro Val Gly Ser Ile
                325                 330                 335

Leu Glu Asn Gln Thr Val Thr Leu Ala Cys Asn Thr Pro Lys Glu Ala
            340                 345                 350

Pro Ser Glu Leu Arg Tyr Ser Trp Tyr Lys Asn His Ala Leu Leu Glu
            355                 360                 365

Gly Ser His Ser Arg Thr Leu Arg Leu His Ser Val Thr Arg Ala Asp
            370                 375                 380

Ser Gly Phe Tyr Phe Cys Glu Val Gln Asn Ala Arg Gly Arg Glu Arg
385                 390                 395                 400

Ser Pro Pro Val Ser Val Val Ser His Pro Pro Leu Thr Pro Asp
                405                 410                 415

Leu Thr Ala Phe Leu Glu Thr Gln Ala Gly Leu Val Gly Ile Leu Gln
            420                 425                 430

Cys Ser Val Val Ser Glu Pro Pro Ala Thr Leu Val Leu Ser His Gly
            435                 440                 445

Gly Leu Ile Leu Thr Ser Thr Ser Glu Glu Gly Asp His Ser Pro Arg
450                 455                 460

Phe Ser Val Thr Ser Ala Pro Asn Ser Leu Arg Leu Glu Ile Gln Asp
465                 470                 475                 480

Leu Gly Pro Thr Asp Ser Gly Glu Tyr Met Cys Ser Ala Ser Ser Ser
                485                 490                 495

Leu Gly Asn Ala Ser Ser Thr Leu Asp Phe His Ala Asn Ala Ala Arg
            500                 505                 510

Leu Leu Ile Ser Pro Ala Ala Glu Val Val Glu Gly Gln Ala Val Thr
            515                 520                 525

Leu Ser Cys Arg Ser Ser Leu Ser Leu Met Pro Asp Thr Arg Phe Ser
            530                 535                 540

Trp Tyr Leu Asn Gly Ala Leu Ile Leu Glu Gly Pro Ser Ser Ser Leu
545                 550                 555                 560
```

```
Leu Leu Pro Ala Ala Ser Ser Thr Asp Ala Gly Ser Tyr His Cys Arg
            565                 570                 575

Ala Gln Asn Ser His Ser Thr Ser Gly Pro Ser Ser Pro Ala Val Leu
            580                 585                 590

Thr Val Leu Tyr Ala Pro Arg Gln Pro Val Phe Thr Ala Gln Leu Asp
            595                 600                 605

Pro Asp Thr Ala Gly Ala Gly Ala Gly Arg Gln Gly Leu Leu Leu Cys
            610                 615                 620

Arg Val Asp Ser Asp Pro Pro Ala Gln Leu Gln Leu Leu His Arg Gly
625                 630                 635                 640

Arg Val Val Ala Ser Ser Leu Ser Trp Gly Gly Cys Cys Thr Cys
            645                 650                 655

Gly Gly Cys Phe His Arg Met Lys Val Thr Lys Ala Pro Asn Leu Leu
            660                 665                 670

Arg Val Glu Ile Arg Asp Pro Val Leu Glu Asp Glu Gly Val Tyr Leu
            675                 680                 685

Cys Glu Ala Ser Ser Thr Leu Gly Asn Ala Ser Ala Ser Ala Thr Leu
            690                 695                 700

Asp Ala Gln Ala Thr Val Leu Val Ile Thr Pro Ser His Thr Leu Gln
705                 710                 715                 720

Glu Gly Ile Glu Ala Asn Leu Ile Cys Asn Val Ser Arg Glu Ala Ser
            725                 730                 735

Gly Pro Ala Asn Phe Ser Trp Phe Arg Asp Gly Ala Leu Trp Ala Gln
            740                 745                 750

Gly Pro Leu Asp Thr Val Thr Leu Leu Pro Val Ala Arg Thr Asp Ala
            755                 760                 765

Ala Leu Tyr Ala Cys Arg Ile Val Thr Glu Ala Gly Ala Gly Leu Ser
            770                 775                 780

Thr Pro Val Ala Leu Asn Val Leu Tyr Pro Pro Asp Pro Pro Lys Leu
785                 790                 795                 800

Ser Ala Leu Leu Asp Val Asp Gln Gly His Thr Ala Val Phe Val Cys
            805                 810                 815

Thr Val Asp Ser Arg Pro Leu Ala Gln Leu Ala Leu Phe Arg Gly Glu
            820                 825                 830

His Leu Leu Ala Ala Ser Ala Leu Arg Leu Pro Pro Arg Gly Arg
            835                 840                 845

Leu Gln Ala Lys Ala Ser Ala Asn Ser Leu Gln Leu Glu Val Arg Asp
            850                 855                 860

Leu Ser Leu Gly Asp Ser Gly Ser Tyr His Cys Glu Ala Thr Asn Ile
865                 870                 875                 880

Leu Gly Ser Ala Asn Thr Ser Leu Thr Phe Gln Val Arg Gly Ala Trp
            885                 890                 895

Val Arg Val Ser Pro Ser Pro Glu Leu Gln Glu Gly Gln Ala Val Val
            900                 905                 910

Leu Ser Cys Gln Val Pro Ile Gly Val Leu Glu Gly Thr Ser Tyr Arg
            915                 920                 925

Trp Tyr Arg Asp Gly Gln Pro Leu Gln Glu Ser Thr Ser Ala Thr Leu
            930                 935                 940

Arg Phe Ala Ala Ile Thr Leu Ser Gln Ala Gly Ala Tyr His Cys Gln
945                 950                 955                 960

Ala Gln Ala Pro Gly Ser Ala Thr Thr Asp Leu Ala Ala Pro Val Ser
            965                 970                 975
```

-continued

```
Leu His Val Thr Tyr Ala Pro Arg Gln Ala Thr Leu Thr Thr Leu Met
            980                 985                 990

Asp Ser Gly Leu Gly Arg Leu Gly Leu Leu Leu Cys Arg Val Asn Ser
            995                 1000                1005

Asp Pro Pro Ala Gln Leu Arg Leu Leu His Gly Ser Arg Leu Val
    1010                1015                1020

Ala Ser Thr Leu Gln Gly Val Glu Glu Leu Ala Gly Ser Ser Pro
    1025                1030                1035

Arg Leu Gln Val Ala Thr Ala Pro Asn Thr Leu Arg Leu Glu Ile
    1040                1045                1050

His Asn Ala Val Leu Glu Asp Glu Gly Val Tyr Thr Cys Glu Ala
    1055                1060                1065

Thr Asn Thr Leu Gly Gln Thr Leu Ala Ser Ala Ala Phe Asp Ala
    1070                1075                1080

Gln Ala Met Arg Val Gln Val Trp Pro Asn Ala Thr Val Gln Glu
    1085                1090                1095

Gly Gln Leu Val Asn Leu Thr Cys Leu Val Trp Thr Thr His Leu
    1100                1105                1110

Ala Gln Leu Thr Tyr Thr Trp Tyr Arg Asp Gln Gln Gln Leu Pro
    1115                1120                1125

Gly Ala Ala His Ser Ile Leu Leu Pro Asn Val Thr Val Thr Asp
    1130                1135                1140

Ala Ala Ser Tyr Arg Cys Gly Ile Leu Ile Pro Gly Gln Ala Leu
    1145                1150                1155

Arg Leu Ser Arg Pro Val Ala Leu Asp Val Leu Tyr Ala Pro Arg
    1160                1165                1170

Arg Leu Arg Leu Thr His Leu Leu Glu Ser Arg Gly Gly Gln Leu
    1175                1180                1185

Ala Val Val Leu Cys Thr Val Asp Ser Arg Pro Ala Ala Gln Leu
    1190                1195                1200

Thr Leu Ser His Ala Gly Arg Leu Leu Ala Ser Ser Thr Ala Ala
    1205                1210                1215

Ser Val Pro Asn Thr Leu Arg Leu Glu Leu Trp Glu Pro Arg Pro
    1220                1225                1230

Ser Asp Glu Gly Leu Tyr Ser Cys Ser Ala Arg Ser Pro Leu Gly
    1235                1240                1245

Gln Ala Asn Thr Ser Leu Glu Leu Arg Leu Glu Gly Val Gln Val
    1250                1255                1260

Thr Leu Ala Pro Ser Thr Thr Val Pro Glu Gly Ala Pro Val Thr
    1265                1270                1275

Val Thr Cys Glu Asp Pro Ala Ala Arg Pro Pro Thr Leu Tyr Val
    1280                1285                1290

Trp Tyr His Asn Ser Arg Trp Leu Gln Glu Gly Ser Ala Ala Ser
    1295                1300                1305

Leu Ser Phe Pro Ala Ala Thr Arg Ala His Ala Gly Ala Tyr Thr
    1310                1315                1320

Cys Gln Val Gln Asp Ala Gln Gly Thr Arg Ile Ser Gln Pro Ala
    1325                1330                1335

Ala Leu His Ile Leu Tyr Ala Pro Arg Asp Ala Val Leu Ser Ser
    1340                1345                1350

Phe Trp Asp Ser Arg Ala Ser Pro Met Ala Val Val Gln Cys Thr
    1355                1360                1365

Val Asp Ser Glu Pro Pro Ala Glu Met Thr Leu Ser Arg Asp Gly
```

```
                    1370                1375                1380
Lys Val Leu Ala Thr Ser His Gly Ala His Gly Leu Ala Val Gly
    1385                1390                1395

Thr Gly His Val Gln Val Ala Arg Asn Ala Leu Gln Leu Arg Val
    1400                1405                1410

Gln Asn Val Pro Ser Arg Asp Lys Asp Thr Tyr Val Cys Met Ala
    1415                1420                1425

Arg Asn Ser Leu Gly Ser Val Ser Thr Met Gly Gln Leu Gln Pro
    1430                1435                1440

Glu Gly Val His Val Val Ala Glu Pro Gly Leu Asp Val Pro Glu
    1445                1450                1455

Gly Thr Ala Leu Asn Leu Ser Cys Arg Leu Pro Ser Gly Pro Gly
    1460                1465                1470

His Met Gly Asn Ser Thr Phe Ala Trp Phe Arg Asn Gly Arg Gln
    1475                1480                1485

Leu His Thr Glu Ser Val Pro Thr Leu Thr Phe Thr His Val Ala
    1490                1495                1500

Arg Ala Gln Ala Gly Leu Tyr His Cys Gln Ala Glu Leu Pro Ala
    1505                1510                1515

Gly Ala Ala Thr Ser Ala Pro Val Leu Leu Arg Val Leu Tyr Pro
    1520                1525                1530

Pro Lys Thr Pro Thr Met Thr Val Phe Val Glu Pro Glu Gly Gly
    1535                1540                1545

Ile Gln Gly Ile Leu Asp Cys Arg Val Asp Ser Glu Pro Leu Ala
    1550                1555                1560

Ser Leu Thr Leu His Leu Gly Ser Arg Leu Val Ala Ser Ser Gln
    1565                1570                1575

Pro Gln Ala Ala Pro Ala Lys Pro His Ile Arg Val Ser Ala Ser
    1580                1585                1590

Pro Asn Ala Leu Arg Val Asp Met Glu Glu Leu Lys Pro Ser Asp
    1595                1600                1605

Gln Gly Glu Tyr Val Cys Ser Ala Ser Asn Ala Leu Gly Ser Ala
    1610                1615                1620

Ser Ala Ala Thr Tyr Phe Gly Thr Arg Ala Leu His Arg Leu His
    1625                1630                1635

Leu Phe Arg His Leu Leu Trp Phe Leu Gly Leu Leu Ala Ser Leu
    1640                1645                1650

Leu Phe Leu Leu Leu Gly Leu Gly Val Trp Tyr Ala Trp Arg Arg
    1655                1660                1665

Gly Asn Phe His Lys Leu Arg Met Gly Glu Tyr Ser Val Glu Met
    1670                1675                1680

Val Ser Arg Lys Glu Thr Thr Gln Met Ser Thr Asp Gln Glu Glu
    1685                1690                1695

Val Thr Gly Ile Gly Asp Asp Ala Gly Ser Val Asn Gln Ala Ala
    1700                1705                1710

Phe Asp Pro Ala His Leu Cys Glu Asn Thr Gln Ser Val Lys Ser
    1715                1720                1725

Thr Val
    1730

<210> SEQ ID NO 5
<211> LENGTH: 5
<212> TYPE: PRT
<213> ORGANISM: porcine
```

```
<400> SEQUENCE: 5

Phe Ser Trp Tyr Arg
1               5

<210> SEQ ID NO 6
<211> LENGTH: 10
<212> TYPE: PRT
<213> ORGANISM: porcine

<400> SEQUENCE: 6

Pro Pro Ala Gln Leu Gln Leu Ile His Arg
1               5                   10

<210> SEQ ID NO 7
<211> LENGTH: 9
<212> TYPE: PRT
<213> ORGANISM: porcine

<400> SEQUENCE: 7

Ala Ser Ser Thr Ala Ala Ser Val Pro
1               5

<210> SEQ ID NO 8
<211> LENGTH: 12
<212> TYPE: PRT
<213> ORGANISM: porcine

<400> SEQUENCE: 8

Trp Leu Gln Glu Gly Ser Ala Ala Ser Leu Ser Phe
1               5                   10

<210> SEQ ID NO 9
<211> LENGTH: 11
<212> TYPE: PRT
<213> ORGANISM: porcine

<400> SEQUENCE: 9

Asp Ala Val Leu Ser Ser Phe Trp Asp Ser Arg
1               5                   10

<210> SEQ ID NO 10
<211> LENGTH: 10
<212> TYPE: PRT
<213> ORGANISM: porcine

<400> SEQUENCE: 10

Ala Leu Leu Leu Gly Gln Val Glu Gln Arg
1               5                   10

<210> SEQ ID NO 11
<211> LENGTH: 14
<212> TYPE: PRT
<213> ORGANISM: porcine

<400> SEQUENCE: 11

Gln Ala Thr Leu Thr Thr Ile Met Asp Ser Gly Leu Gly Arg
1               5                   10

<210> SEQ ID NO 12
<211> LENGTH: 5
<212> TYPE: PRT
<213> ORGANISM: porcine

<400> SEQUENCE: 12
```

```
Phe Ser Trp Tyr Leu
1               5

<210> SEQ ID NO 13
<211> LENGTH: 10
<212> TYPE: PRT
<213> ORGANISM: porcine

<400> SEQUENCE: 13

Pro Pro Ala Gln Leu Arg Leu Leu His Gly
1               5                   10

<210> SEQ ID NO 14
<211> LENGTH: 9
<212> TYPE: PRT
<213> ORGANISM: porcine

<400> SEQUENCE: 14

Ala Ser Ser Thr Ala Ala Ser Val Pro
1               5

<210> SEQ ID NO 15
<211> LENGTH: 12
<212> TYPE: PRT
<213> ORGANISM: porcine

<400> SEQUENCE: 15

Trp Leu Gln Glu Gly Ser Ala Ala Ser Leu Ser Phe
1               5                   10

<210> SEQ ID NO 16
<211> LENGTH: 11
<212> TYPE: PRT
<213> ORGANISM: porcine

<400> SEQUENCE: 16

Asp Ala Val Leu Ser Ser Phe Trp Asp Ser Arg
1               5                   10

<210> SEQ ID NO 17
<211> LENGTH: 10
<212> TYPE: PRT
<213> ORGANISM: porcine

<400> SEQUENCE: 17

Ala Leu Leu Leu Gly Gln Val Glu Gln Arg
1               5                   10

<210> SEQ ID NO 18
<211> LENGTH: 14
<212> TYPE: PRT
<213> ORGANISM: porcine

<400> SEQUENCE: 18

Gln Ala Thr Leu Thr Thr Leu Met Asp Ser Gly Leu Gly Arg
1               5                   10

<210> SEQ ID NO 19
<211> LENGTH: 5
<212> TYPE: PRT
<213> ORGANISM: mouse

<400> SEQUENCE: 19

Phe Ser Trp Tyr Leu
```

```
<210> SEQ ID NO 20
<211> LENGTH: 10
<212> TYPE: PRT
<213> ORGANISM: mouse

<400> SEQUENCE: 20

Pro Pro Ala Gln Leu Gln Leu Phe His Arg
1               5                   10

<210> SEQ ID NO 21
<211> LENGTH: 9
<212> TYPE: PRT
<213> ORGANISM: mouse

<400> SEQUENCE: 21

Ala Ser Ser Thr Glu Ala Ser Val Pro
1               5

<210> SEQ ID NO 22
<211> LENGTH: 12
<212> TYPE: PRT
<213> ORGANISM: mouse

<400> SEQUENCE: 22

Trp Leu Gln Glu Gly Pro Ala Ser Ser Leu Gln Phe
1               5                   10

<210> SEQ ID NO 23
<211> LENGTH: 11
<212> TYPE: PRT
<213> ORGANISM: mouse

<400> SEQUENCE: 23

Asp Ala Val Leu Ser Ser Phe Arg Asp Ser Arg
1               5                   10

<210> SEQ ID NO 24
<211> LENGTH: 20
<212> TYPE: DNA
<213> ORGANISM: mouse

<400> SEQUENCE: 24
tcctcaactg cagcctctgt                                              20

<210> SEQ ID NO 25
<211> LENGTH: 20
<212> TYPE: DNA
<213> ORGANISM: mouse

<400> SEQUENCE: 25
agtgaggcag ccgttccctc                                              20

<210> SEQ ID NO 26
<211> LENGTH: 20
<212> TYPE: DNA
<213> ORGANISM: porcine

<400> SEQUENCE: 26
tctggtcttt gagcttcgtc                                              20

<210> SEQ ID NO 27
<211> LENGTH: 20
```

<212> TYPE: DNA
<213> ORGANISM: porcine

<400> SEQUENCE: 27
acctgagggt tgctgctatt                                                   20

<210> SEQ ID NO 28
<211> LENGTH: 23
<212> TYPE: DNA
<213> ORGANISM: porcine

<400> SEQUENCE: 28
gacgcccacc atgactgttt ttg                                               23

<210> SEQ ID NO 29
<211> LENGTH: 28
<212> TYPE: DNA
<213> ORGANISM: porcine

<400> SEQUENCE: 29
caccatggac ttcctgctcc tgctcctc                                          28

<210> SEQ ID NO 30
<211> LENGTH: 25
<212> TYPE: DNA
<213> ORGANISM: porcine

<400> SEQUENCE: 30
cttggggttt gaagctaggt cataa                                             25

<210> SEQ ID NO 31
<211> LENGTH: 27
<212> TYPE: DNA
<213> ORGANISM: porcine

<400> SEQUENCE: 31
cacctggcag ctgagggtga ccagatc                                           27

<210> SEQ ID NO 32
<211> LENGTH: 5193
<212> TYPE: DNA
<213> ORGANISM: porcine

<400> SEQUENCE: 32
atggacttcc tgctcctgct cctcctcctg gcttcatctg ctctagcagg cctggcctcg      60
tggacggttt ccagccccga gaccgtgcag ggcatcaagg gctcctgcct catcatcccc     120
tgcaccttcg gcttcccggc caacgtggag gtgccccatg gcatcacagc catctggtac     180
tatgactact caggcaagcg cctggtagtg agccactcca ggaacccaaa ggtggtggag     240
aaccacttcc aaggccgggc cctgctgttg gggcaggttg aacagaggac gtgcagcctg     300
ctgctgaagg acctgcagcc ccaggactcg ggctcctata acttccgctt tgagatcagc     360
gagggcaacc gctggtcaga tgtcaaaggc acagttgtca ccgtgacaga ggtgcccagc     420
gtgcccacca ttgccttgcc agccaagctg catgagggca tggaggtgga cttcaactgc     480
tccactccct atgtgtgccc gacggagccg gtcaacctac agtggcaagg ccaggatccc     540
acccgctccg tcacctccca cctccagaag cttgagccct cgggcaccag ccacatggag     600
accctgcaca tggccctgtc ctggcaggac catggccgga tcctgagctg ccaggtctca     660
gcagccgaac gcaggatgca gaaggagatt caccctccaag tgcagtatgc ccccaagggt     720

```
gtggagatcc ttttcagcca ctccggacgg aacgtccttc caggtgatct ggtcaccctc    780
agctgccagg tgaatagcag caaccctcag gtcagttccg tgcagtgggt caaggatggg    840
acgaagctca aagaccagaa acgtgtactg cagttgcgcc gggcagcctg ggctgatgct    900
ggcgtctaca cctgccaagc cgggaatgcc gtgggctctt cagtctcacc cccggtcagc    960
ctccacgtct tcatggctga ggtccaggta agccctgtgg gctccatcct ggagaaccag   1020
acggtgacgc tggcctgcaa tacacctaag gaagcgccca gcgagctgcg ctacagctgg   1080
tacaagaacc acgccctgct ggagggctct cacagccgca ccctccggct gcactcagtt   1140
accagggcgg attcgggctt ctacttctgc gaggtgcaga acgcccgggg cagagagcgc   1200 tctcccctg tcagcgtggt ggtcagccac ccacccctca ccccggacct aactgccttc   1260
ctggagacac aggcggggct ggtgggcatc ctccaatgct ctgtggtcag cgagccccca   1320
gctactctgg tgttgtcaca cggggggcctc atcttggcct ctacctccgg ggagggtgac   1380
cacagcccac gcttcagtgt cgcctctgcc cccaactccc tgcgcctgga gattcaagac   1440
ctggggccaa cagacagtgg ggaatacatg tgctcagcca gcagttctct tgggaatgcg   1500
tcctccaccc tggacttcca tgccaatgca gcccgcctcc tcatcagccc agcagcagag   1560
gtggtggaag gcaggcggt gacactgagc tgcaggagca gcctgagcct gatgcctgac   1620
acccgttttt cctggtacct gaacgggccc tgattctcg aggggcccag cagcagcctc   1680
ctgctcccag cagcctccag cacagatgcc ggctcatacc actgccgggc ccagaacagc   1740
cacagcacca gcgggccctc ctcacctgct gttctcaccg tgctctacgc cccacgccag   1800
cccgtgttca ctgcccagct ggaccctgat actgcaggag ctggggccgg acgccaaggc   1860
ctcctcttgt gccgtgtgga cagcgacccc ccagcccagc tgcagctgct ccacagggc    1920 cgtgttgtgg cctcttctct gtcatggggg gcggctgct gcacctgcgg aggctgtttc   1980
caccgcatga aggtcaccaa agcacccaac ctactgcgtg tagagatccg agacccggtg   2040
ctggaggatg agggtgtgta cctgtgcgag gccagcagcg ccctgggcaa cgcctccgcc   2100
tctgcaacct tggatgccca ggccactgtc ctggtcatca caccgtcaca cacgctgcag   2160
gaaggcattg aagccaacct gacttgcaac gtgagccgtg aagccagcgg ccctgccaac   2220
ttctcctggt tccagatggg ggcgctatgg gcccagggcc ctctggacac cgtgacgctg   2280
ctacctgtgg ccagaactga tgctgccctc tatgcttgcc gcatcgtcac cgaggctggt   2340
gctggcctct ccacccctgt ggccctgaat gtgctctatc ccccgatcc tccaaagttg   2400 tcagccctcc tggacgtgga ccagggccac acggctgtgt cgtctgtac tgtggacagt   2460 cgccctcttg cccagttggc cctgttccgt ggggaacacc tcctggccgc cagctcggca   2520
ctccggctcc cccctcgtgg ccgcctccag gccaaagcct cggccaactc cttgcagcta   2580
gaggtccgag acttgagcct tggggactct ggcagctacc actgtgaggc caccaacatc   2640
cttggatcag ccaacacttc tcttaccttc caggtccgag gagcctgggt ccgggtgtca   2700
ccgtcgcctg agctccagga gggccaggct gtggtcctga gctgccaggt acccataggg   2760
gtcctggagg ggacctcata tcgttggtat cgggatggcc agccctcca ggagtccact   2820 tcggccacgc tccgttttgc agccataact ctgagccagg ctggagccta ccattgccaa   2880
gcccaagctc caggctcagc caccacggac ctggctgccc ctgtcagcct ccacgtgacc   2940
tacgcacctc gccaggccac actcaccacc ctgatggact caggcctcgg gcgactgggc   3000
ctccttctgt gccgtgtgaa cagtgaccct cctgcccagc ccgactgct ccatgggagc   3060 cgcctcgtgg cctctactct acaaggtgtg gaggagcttg caggcagctc tccccgccta   3120
```

```
caggtggcca cagcccccaa cacgctgcgc ctggagatcc acaacgcagt gctggaggat    3180
gaaggcgtct acacctgcga ggccaccaac accctgggtc agaccttggc ctccgccgcc    3240
ttcgatgccc aggctatgag agtgcaggtg tggcccaatg ccaccgtgca agaggggcag    3300
ctggtgaacc tgacctgcct tgtatggacc acgcacctgg cccagctcac ctacacgtgg    3360
taccgagacc agcagcagct cccaggtgct gccactcca tcctcctgcc caatgtcact    3420
gtcacagatg ccgcctccta ccgctgtggc atattgatcc ctggccaggc actccgcctc    3480
tccagacctg tcgccctgga tgtcctctac gcaccccgca gactgcgcct gacccatctc    3540
ttggagagcc gtggtgggca gctggccgtg gtgctgtgca ctgtggacag tcgcccagct    3600
gcccagctga ccctcagcca tgctggccgc ctcctggcct cctcaaccgc agcctctgtc    3660
cccaacaccc tgcgcctgga gctgtgggag ccccggccca gtgatgaggg tctctacagc    3720
tgctcggccc gcagtcctct gggccaggcc aacacatccc tggagctgcg gctagagggc    3780
gtgcaggtgg cactggctcc atcggccact gtgccggagg gggcccctgt cacagtgacc    3840
tgtgaagacc ctgctgcccg cccacccact ctctatgtct ggtaccacaa cagccgttgg    3900
ctgcaggagg ggtcggctgc ctccctctcg tttccagcgg ctacacgggc tcacgcgggc    3960
gcctatacct gccaggtcca ggatgcccag ggcacgcgca tctcccagcc cgcagcactg    4020
cacatcctct atgcccctcg ggatgctgtc ctttcctcct tctgggactc aagggccagc    4080
cctatgccg tggtacagtg cactgtggac agcgagccac ctgccgagat gaccctgtcc    4140
catgatggca aggtgctggc caccagccat ggggtccacg gcttagcagt ggggacaggc    4200
catgtccagg tggcccgcaa cgccctgcag ctgcgggtgc agaatgtgcc ctcacgtgac    4260
aaggacacct acgtctgcat ggaccgcaac tccttgggct cagtcagcac catggggcag    4320
ctgcagccag aaggtgtgca cgtggtagct gagccagggc tggatgtgcc tgaaggcaca    4380
gcgctgaacc tgagctgtcg cctccctagt ggccctgggc acataggcaa ctccaccttt    4440
gcttggttcc ggaacggtcg gcagctacac acagagtctg tgcccaccct taccttcacc    4500
catgtggccc gcgcccaagc tggcttgtac cactgccagg ctgagctccc cgccggggct    4560
gccacctctg ctccagtctt gctccgggtg ctctaccctc ccaagacgcc caccatgact    4620
gttttttgtgg agcccgaggg tggcatccag ggcattctgg actgccgagt ggacagtgag    4680
cccctagcca gcctgaccct ccacctgggc agtcggctgg tggcctccag ccagcctcag    4740
gctgccctg ccaagccgca catccgcgtc tcagccagtc ccaatgcctt gcgagtggac    4800
atggaggagc tgaagcccag tgaccagggg gagtatgtgt gctcggcctc caatgccctg    4860
ggctctgcct ctgctgccac ctacttcgga accagagccc tgcatcgcct gcatctgttc    4920
cagcaccttc tctggttcct ggggctgctg gcgagcctcc tcttcctact gttgggcctg    4980
ggggtctggt acgcctggag acggggaaat ttttacaagc tgagaatggg cgaatattca    5040
gtagagatgg tatctcggaa ggaaaccacg cagatgtcca ctgaccagga agaagttact    5100
ggaatcggtg atgatgcggg ctctgtgaac caggcggcat ttgatcctgc ccacctctgt    5160
gaaaacacac agtctgtgaa aagcacagtc tga                                5193
```

<210> SEQ ID NO 33
<211> LENGTH: 5193
<212> TYPE: DNA
<213> ORGANISM: Porcine

<400> SEQUENCE: 33

```
tacctgaagg acgaggacga ggaggaggac cgaagtaggc gagatcgtcc ggaccggagc      60
acctgccaaa ggttggggct ctggcacgtc ccgtagttcc cgaggacgga gtagtagggg     120
acgtggaagc cgaagggccg gttgcacctc cacggggtac cgtagtgtcg gtagaccatg     180
atactgatga gtccgttcgc ggaccatcac tcggtgaggt ccttgggttt ccaccacctc     240
ttggtgaagg ttctgccccg ggacgacaac cccgtccaac tcgtctcctg cacgtcggac     300
gacgacttcc tggacgtcgg ggtcctgagc ccgaggatat tgaaggcgaa actctagtcg     360
ctcccgttgg cgaccagtct acagtttccg tgtcaacagt ggcactgtct ccacgggtcg     420
cacgggtggt aacggaacgg tcggttcgac gtactcccgt acctccacct gaagttgacg     480
aggtgaggga tacacacggg ctgcctcggc cagttggatg tcaccgttcc ggtcctaggg     540
tgggcgaggc agtggagggt ggaggtcttc gaactcggga gcccgtggtc ggtgtacctc     600
tgggacgtgt accgggacag gaccgtcctg gtaccggcct aggactcgac ggtccagagt     660
cgtcggcttg cgtcctacgt cttcctctaa gtggaggttc acgtcatacg ggggttccca     720
cacctctagg aaaagtcggt gaggcctgcc ttgcaggaag gtccactaga ccagtgggag     780
tcgacggtcc acttatcgtc gttgggagtc tagtcaaggc acgtcaccca gttcctaccc     840
tgcttcgagt ttctggtctt tgcacatgac gtcaacgcgg cccgtcggac ccgactacga     900
ccgcagatgt ggacggttcg gcccttacgg caccccgagaa gtcagagtgg gggccagtcg     960
gaggtgcaga agtaccgact ccaggtccat tcgggacacc cgaggtagga cctcttggtc    1020
tgccactgcg accggacgtt atgtggattc cttcgcgggt cgctcgacgc gatgtcgacc    1080
atgttcttgg tgcgggagga cctcccgaga gtgtcggcgt gggaggccga cgtgagtcag    1140
tggtcccgcc taagcccgaa gatgaagacg ctccacgtct tgcgggcccc gtctctcgcg    1200 agaggggggac agtcgcacca ccagtcggtg ggtggggagt ggggcctgga ttgacggaag    1260
gacctctgtg tccgccccga ccacccgtag gaggttacga gacaccagtc gctcgggggt    1320
cgatgagacc acaacagtgt gccccggag tagaactgga gatggaggct cctcccactg    1380
gtgtcgggtg cgaagtcaca gtggagacgg gggttgaggg acgcggacct ctaagttctg    1440
gaccccggtt gtctgtcacc ccttatgtac acgagtcggt cgtcaagaga acccttacgc    1500
aggaggtggg acctgaaggt acggttacgt cgggcgagg agtagtcggg tcgtcgtctc    1560
caccaccttc ccgtccgcca ctgtgactcg acgtcctcgt cggactcgga ctacggactg    1620
tgggcaaaaa ggaccatgga cttgccccgg gactaagagc tccccgggtc gtcgtcggag    1680
gacgagggtc gtcggaggtc gtgtctacgg ccgagtatgg tgacggcccg ggtcttgtcg    1740
gtgtcgtggt cgcccgggag gagtggacga caagagtggc acgagatgcg gggtgcggtc    1800
gggcacaagt gacgggtcga cctgggacta tgacgtcctc gaccccggcc tgcggttccg    1860
gaggagaaca cggcacacct gtcgctgggg ggtcgggtcg acgtcgacga ggtgtccccg    1920
gcacaacacc ggagaagaga cagtaccccc ccgccgacga cgtggacgcc tccgacaaag    1980
gtggcgtact tccagtggtt tcgtgggttg gatgacgcac atctctaggc tctgggccac    2040
gacctcctac tcccacacat ggacacgctc cggtcgtcgt gggacccgtt gcggaggcgg    2100
agacgttgga acctacgggt ccggtgacag gaccagtagt gtggcagtgt gtgcgacgtc    2160
cttccgtaac ttcggttgga ctaaacgttg cactcggcac ttcggtcgcc gggacggttg    2220
aagaggacca aggctctacc ccgcgatacc cgggtcccgg gagacctgtg gcactgtgac    2280
gatggacacc ggtcttgact acgacgggag atacgaacgg cgtagcagtg gctccgacca    2340
cgaccggaga ggtgggggaca ccgggactta cacgagatag gggggctagg aggtttcaac    2400
```

```
agtcgggagg acctgcacct ggtcccggtg tgccgacaca agcagacatg acacctgtca   2460
gcgggagaac gggtcaaccg ggacaaggca ccccttgtgg aggaccggcg gtcgagccgt   2520
gaggccgagg ggggagcacc ggcggaggtc cggtttcgga gccggttgag aacgtcgat    2580 ctccaggctc tgaactcgga acccctgaga ccgtcgatgg tgacactccg gtggttgtag   2640
gaacctagtc ggttgtgaag agaatggaag gtccaggctc ctcggaccca ggcccacagt   2700
ggcagcggac tcgaggtcct cccggtccga caccaggact cgacggtcca tgggtatccc   2760
caggacctcc cctggagtat agcaaccata gccctaccgg tcggggaggt cctcaggtga   2820
agccggtgcg aggcaaaacg tcggtattga gactcggtcc gacctcggat ggtaacggtt   2880
cgggttcgag gtccgagtcg gtggtgcctg gaccgacggg gacagtcgga ggtgcactgg   2940
atgcgtggag cggtccggtg tgagtggtgg gactacctga gtccggagcc cgctgacccg   3000
gaggaagaca cggcacactt gtcactggga ggacgggtcg aggctgacga ggtaccctcg   3060
gcggagcacc ggagatgaga tgttccacac ctcctcgaac gtccgtcgag aggggcggat   3120
gtccaccggt gtcggggggtt gtgcgacgcg gacctctagg tgttgcgtca cgacctccta   3180
cttccgcaga tgtggacgct ccggtggttg tgggacccag tctggaaccg gaggcggcgg   3240
aagctacggg tccgatactc tcacgtccac accgggttac ggtggcacgt tctcccgtc    3300 gaccacttgg actggacgga acatacctgg tgcgtggacc gggtcgagtg gatgtgtacc   3360
atggctctgg tcgtcgtcga gggtccacga cgggtgaggt aggaggacgg gttacagtga   3420
cagtgtctac ggcggaggat ggcgacaccg tataactagg gaccggtccg tgaggcggag   3480
aggtctggac agcgggacct acaggagatg cgtgggggcgt ctgacgcgga ctgggtagag   3540
aacctctcgg caccacccgt cgaccggcac cacgacacgt gacacctgtc agcgggtcga   3600
cgggtcgact gggagtcggt acgaccggcg gaggaccgga ggagttggcg tcggagacag   3660
gggttgtggg acgcgacct cgacaccctc ggggccgggt cactactccc agagatgtcg    3720
acgagccggg cgtcaggaga cccggtccgg ttgtgtaggg acctcgacgc cgatctcccg   3780
cacgtccact gtgaccgagg tagctggtga cacggcctcc cccggggaca gtgtcactgg   3840
acacttctgg gacgacgggc gggtgggtgg gagatacaga ccatggtgtt gtcggcaacc   3900
gacgtcctcc ccagccgacg gagggagagc aaaggtcgcc gatgtgcccg agtgcgcccg   3960
cggatatgga cggtccaggt cctacgggtc ccgtgtgcgt agagggtcgg gcgtcgtgac   4020
gtgtaggaga tacggggagc cctacgacag gaaaggagga agaccctgag ttcccggtcg   4080
ggataccggc accatgtcac gtgacacctg tcgctcggtg gacggctcta ctgggacagg   4140
gcactaccgt tccacgaccg gtggtcggta ccccgggtgc cgaatcgtca ccctgtccg    4200 gtacaggtcc accgggcgtt gcgggacgtc gacgcccacg tcttacacgg gagtgcactg   4260
ttcctgtgga tgcagacgta ccgggcgttg aggaacccga gtcagtcgtg gtaccccgtc   4320
gacgtcggtc ttccacacgt gcaccatcgg ctcggtcccg acctacacgg gcttccgtgt   4380
cgcgacttgg actcgacagc ggagggatca ccgggacccg tgtacccgtt gaggtggaaa   4440
cgaaccaagg ccttgccagc cgtcgatgtg tgtctcagac acgggtggga atggaagtgg   4500
gtacaccggg cgcgggttcg accgaacatg gtgacggtcc gactcgaggg gcggccccga   4560
cggtggagac gaggtcagaa cgaggcccac gagatgggag ggttctgcgg gtggtactga   4620
caaaaacacc tcgggctccc accgtaggtc ccgtaagacc tgacggctca cctgtcactc   4680
ggggatcggt cggactggga ggtggacccg tcagccgacc accggaggtc ggtcggggtc   4740
```

```
cgacggggac ggttcggcgt gtaggcgcag agtcggtcag ggttacggaa cgctcacctg    4800
tacctcctcg acttcgggtc actggtcccc ctcatacaca cgagccggag gttacgggac    4860
ccgagacgga gacgacggtg gatgaagcct tggtctcggg acgtagcgga cgtagacaag    4920
gccgtggaag agaccaagga ccccgacgac cgctcggagg agaaggatga caacccggac    4980
ccccagacca tgcggacctc tgccccttta aaagtgttcg actcttaccc gcttataagt    5040
catctctacc atagagcctt cctttggtgc gtctacaggt gactggtcct tcttcaatga    5100
ccttagccac tactacgccc gagacacttg gtccgccgta aactaggacg ggtggagaca    5160
cttttgtgtg tcagacactt ttcgtgtcag act                                 5193

<210> SEQ ID NO 34
<211> LENGTH: 27
<212> TYPE: DNA
<213> ORGANISM: porcine

<400> SEQUENCE: 34
cacctggcag ctgagggtga ccagatc                                           27
```